US012686758B2

(12) United States Patent
Bernards et al.

(10) Patent No.: US 12,686,758 B2
(45) Date of Patent: Jul. 21, 2026

(54) ZWITTERIONIC CROSSLINKERS, HYDROGELS COMPRISING ZWITTERIONIC CROSSLINKERS, AND METHODS FOR MAKING AND USING

(71) Applicant: University of Idaho, Moscow, ID (US)

(72) Inventors: Matthew Bernards, Moscow, ID (US); Kristopher Waynant, Moscow, ID (US); Moubani Chakraborty, Moscow, ID (US)

(73) Assignee: University of Idaho, Moscow, ID (US)

( * ) Notice: Subject to any disclaimer, the term of this patent is extended or adjusted under 35 U.S.C. 154(b) by 1142 days.

(21) Appl. No.: 17/714,519

(22) Filed: Apr. 6, 2022

(65) Prior Publication Data

US 2022/0325072 A1 Oct. 13, 2022

Related U.S. Application Data

(60) Provisional application No. 63/171,458, filed on Apr. 6, 2021.

(51) Int. Cl.
*C08K 5/21* (2006.01)
*C07C 227/16* (2006.01)
(Continued)

(52) U.S. Cl.
CPC .............. *C08K 5/21* (2013.01); *C07C 227/16* (2013.01); *C07C 227/20* (2013.01); (Continued)

(58) Field of Classification Search
CPC ....... C08K 5/21; C07C 227/16; C07C 227/20; C07C 231/02; C07C 237/12; C08F 220/283; C08F 220/34; C08J 3/075
See application file for complete search history.

(56) References Cited

U.S. PATENT DOCUMENTS

2024/0132771 A1* 4/2024 Song ...................... C09K 8/508

FOREIGN PATENT DOCUMENTS

CN 103435746 A * 12/2013

OTHER PUBLICATIONS

Machine translation of Li et al. (CN 1034358746A). (Year: 2013).*

* cited by examiner

*Primary Examiner* — Catherine S Branch
(74) *Attorney, Agent, or Firm* — Klarquist Sparkman, LLP

(57) ABSTRACT

Certain disclosed embodiments concern a crosslinker having a Formula I (Polymerizing Group 1)$_s$-(Amino Acid)$_u$-(Polymerizing Group 2)$_y$ Formula I, where polymerizing group 1 and polymerizing group 2 independently are selected from an acrylate, alkyl acrylate, acrylamide, alkyl acrylamide, acrylonitrile, alkyl acrylonitrile or a (hydroxyalkyl) acrylate; s and y are from 1 to 10, with s and y each typically being 1; the amino acid is any naturally occurring amino acid, any non-naturally occurring amino acid, and any and all combinations thereof; and u is 2 to 100. Crosslinkers may include a naturally occurring amino acid or acids that are selected to provide amino-acid defining functional groups that are zwitterionic at a pH of from 2.5 to 10. Disclosed crosslinkers can also include "internal spacers", "external spacers," or both. Crosslinkers according to the present invention are used to make zwitterionic hydrogels that address fouling and bacteria adhesion issues associated with previously known hydrogels. Accordingly, such products are particularly suitable for biomedical applications, such as contact lenses, drug delivery vehicles, tissue engineering platforms, tissue regeneration platforms, catheters, implants and sensors.

27 Claims, 4 Drawing Sheets

(51) Int. Cl.

| | |
|---|---|
| ***C07C 227/20*** | (2006.01) |
| ***C07C 231/02*** | (2006.01) |
| ***C07C 237/12*** | (2006.01) |
| ***C08F 220/28*** | (2006.01) |
| ***C08F 220/34*** | (2006.01) |
| ***C08J 3/075*** | (2006.01) |
| ***G01N 1/30*** | (2006.01) |

(52) U.S. Cl.

CPC .......... *C07C 231/02* (2013.01); *C07C 237/12* (2013.01); *C08F 220/283* (2020.02); *C08F 220/34* (2013.01); *C08J 3/075* (2013.01); *G01N 1/30* (2013.01); *C08F 2810/20* (2013.01); *C08J 2333/14* (2013.01); *G01N 2001/305* (2013.01)

ZWITTERIONIC CROSSLINKERS, HYDROGELS COMPRISING ZWITTERIONIC CROSSLINKERS, AND METHODS FOR MAKING AND USING

CROSS REFERENCE TO RELATED APPLICATION

This application claims the benefit of the earlier filing date of U.S. provisional patent application No. 63/171,458, filed on Apr. 6, 2021, which is incorporated herein by reference in its entirety.

FIELD

The present invention concerns zwitterionic crosslinkers comprising amino acids or peptides and pendent polymerizable groups that are particularly useful for forming biomedically useful hydrogels.

BACKGROUND

A significant challenge for biomedical applications is the naturally occurring foreign body response. Nonspecific protein adsorption to the surface of implanted materials, injected drug delivery vehicles, and other polymer materials leads to a naturally occurring immune response. Upon activation, the immune response clears circulating materials, breaks down implanted materials, and encapsulates materials that are not degradable. These responses lead to reduced circulation times for drug delivery vehicles, the loss of functionality for implantable sensors, and poor tissue regeneration through tissue engineering scaffolds.

Polymer hydrogels are widely utilized in the biomedical field for applications including contact lenses, drug delivery vehicles, and tissue regeneration platforms. When hydrogels are formed, they require using a crosslinker species to bind parallel polymer chains to each other to provide three-dimensional structure. Despite the range of biomedical applications, known polymer hydrogel materials fail as a result of nonspecific protein adsorption and/or bacteria adhesion. Nonspecific protein adsorption leads to the foreign body response, whereas bacteria adhesion leads to infection. Non-fouling materials have been suggested to counteract this natural immune response and bacteria adhesion. The best performing non-fouling materials to date are based on zwitterionic or polyampholyte chemistries that are prepared using ethylene glycol-based crosslinkers (di-, tri-, and tetra-ethylene glycol dimethacrylate as an example) because this family of crosslinkers is FDA approved. The ethylene glycol-based materials reduce, but do not eliminate, the foreign body response. And there is also increasing evidence that some humans produce antibodies to polyethylene glycol (PEG), suggesting that it cannot be universally used. Further, hydrogels based entirely on PEG functional groups produce a foreign body capsule upon implantation.

As a result, a need still exists for new non-fouling polymeric materials and hydrogels made therefrom that are non-fouling and that reduce or eliminate nonspecific protein adsorption, and the foreign body response and/or bacteria adhesion that leads to infection.

SUMMARY

Disclosed embodiments of the present invention address the deficiencies discussed in the Background using zwitterionic crosslinkers comprising amino acids or peptides that are used to form hydrogels. One advantage of the presently disclosed crosslinkers and hydrogels comprising such crosslinkers is the presence of charged regions with overall charge neutrality provided by a zwitterion at a pH from about 2.5 to 10, and even more particularly at physiological pH.

Certain disclosed embodiments concern a crosslinker having a Formula I $$\text{(Polymerizing Group 1)}_s\text{-(Amino Acid)}_u\text{-(Polymerizing Group 2)}_y \qquad \text{Formula I.}$$

With reference to Formula I: polymerizing group 1 and polymerizing group 2 independently are selected from acrylate, alkyl acrylate, acrylamide, alkyl acrylamide, acrylonitrile, alkyl acrylonitrile or a (hydroxyalkyl) acrylate; s and y are from 1 to 10, with s and y each typically being 1; the amino acid is any naturally occurring or non-naturally occurring amino acid, often a naturally occurring amino acid simply due to availability; and u is 2 to 100, more typically 2 to 10. Polymerizing group 1 and polymerizing group 2 often are an alkyl acrylate, alkyl acrylamide or alkyl acrylonitrile, such as methacrylate, ethylacrylate, propylacrylate, methacrylamide, ethylacrylamide, propylacrylamide, methacrylonitrile, ethylacrylonitrile, or propylacrolynitrile. Substituted version of these crosslinkers also can be used, including (hydroxyalkyl) acrylates, such as (hydroxyethyl) methacrylate. Crosslinkers may include a naturally occurring amino acid or acids that are selected to provide amino-acid defining functional groups that are zwitterionic at a pH from 2.5 to 10, such as serine, lysine, aspartic acid, glutamic acid, arginine, histidine, cysteine, threonine, and tyrosine. Alternatively, the naturally occurring amino acid may be modified to include a functional group that is charged at a pH of from 2.5 to 10.

Crosslinkers according to the present invention also may have a Formula II $$\text{[(Polymerizing Group 1)}_s\text{-(Amino Acid 1)}_u\text{-(Internal Spacer)}_v\text{-(Amino Acid 2)}_w\text{-(Polymerizing Group 2)}_y\text{]} \qquad \text{Formula II,}$$

where components of Formula II that are common with Formula I are as stated for Formula I. With reference to Formula II, u and w must sum to at least 2, and are independently 0 to 100, and v is 0 to 20. Particular crosslinkers according to Formula II have s and y=1; u and w=1 to 10; and v=0 to 5. Each internal spacer is independently selected from an amino acid, a peptide, an aliphatic spacer, a heteroaliphatic spacer, a cyclic spacer, a heterocyclic spacer, an aryl spacer, a heteroaryl spacer, and any and all combinations thereof, where each spacer has from 1 to 20 atoms. Amino acids suitable as internal spacers typically include amino acids that do not have a defining functional group that is ionized at a pH of 2.5 to 10, such as glycine. More particularly, each internal spacer independently may be selected from amino acids, peptides, $C_1$-$C_{20}$ alkyl, more typically $C_1$-$C_6$ alkyl, $C_1$-$C_{20}$ heteroalkyl, more typically $C_2$-$C_6$ heteroalkyl, $C_2$-$C_{20}$ ether, $C_2$-$C_{20}$ glycol, $C_2$-$C_{20}$ diol, $C_2$-$C_{20}$ dithiol or $C_2$-$C_{20}$ diamine. Exemplary specific spacers include 2,3-diaminopropanoic acid, 2,4-diaminobutanoic acid, ornithine, 2-aminohexanedioic acid, methylene ($-CH_2-$), ethylene ($-CH_2CH_2)-$), propylene ($-CH_2CH_2CH_2-$), butylene ($-CH_2CH_2CH_2CH_2-$), pentylene ($-CH_2CH_2CH_2CH_2CH_2-$), hexylene ($-CH_2CH_2CH_2CH_2CH_2CH_2-$),

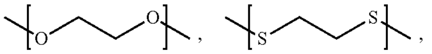

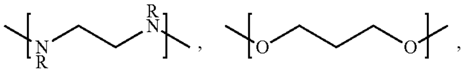

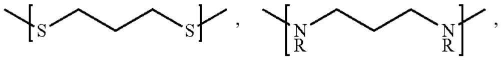

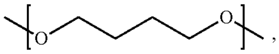

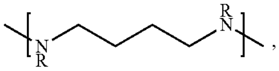

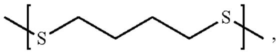

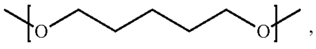

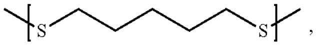

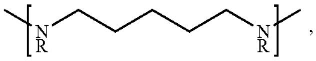

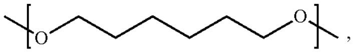

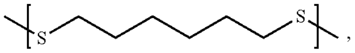

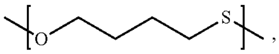

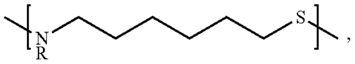

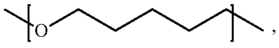

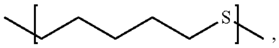

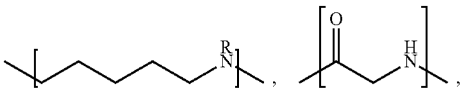

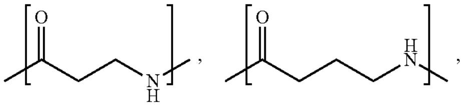

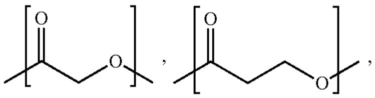

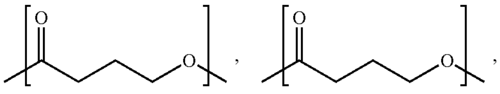

-continued

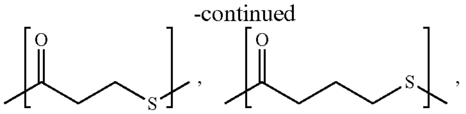

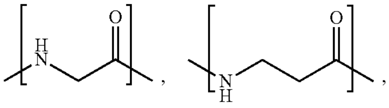

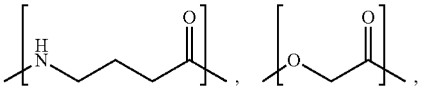

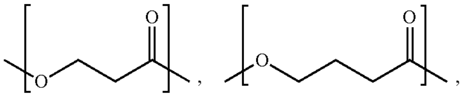

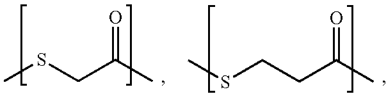 and

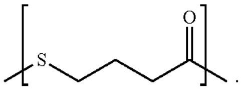

Disclosed crosslinker also may have a Formula III

[(Polymerizing Group $1)_s$-[(External Spacer $1)_t$-(Amino $Acid)_u$-(External Spacer $2)_x$]-(Polymerizing Group $2)_y$] Formula III, where components of Formula III that are common with Formulas I and/or II are as stated for Formulas I and/or II. With particular reference to Formula III, u is at least 2 to 100, external spacer 1 and external spacer 2 are independently selected from any of the spacers discussed for Formula II, and t and x are independently 0-20, more typically 0 to 5.

Disclosed crosslinker also may have a Formula IV

[(Polymerizing Group $1)_s$-(Spacer $1)_t$-(Amino Acid $1)_u$-(Spacer $2)_v$-(Amino Acid $2)_w$-(Spacer $3)_x$-(Polymerizing Group $2)_y$] Formula IV, where components of Formula IV that are common with Formulas I, II and/or III are as stated for Formulas I, II and/or III. With particular reference to Formula IV, u and w must sum to at least 2, and are independently 0 to 100; spacer 1, spacer 2 and spacer 3 are independently selected from any of the spacers discussed with reference to Formula II; and t, v and x are independently 0-20, more typically 0 to 5.

Disclosed crosslinkers also may have a Formula V or VI

Formula V

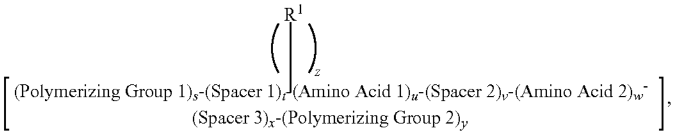

Formula VI

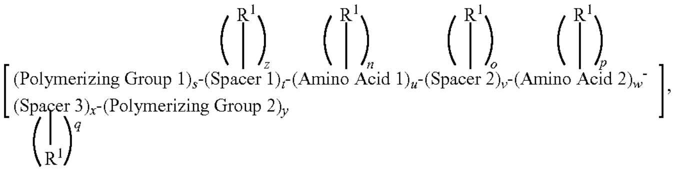

where components of Formulas V and VI that are common with Formulas I, II, III and/or IV are as stated for Formulas I, II, III and/or IV. With particular reference to Formulas V and VI, $R^1$ is independently a $C_1$-$C_{10}$ amine, $C_1$-$C_{10}$ carboxylic acid, $C_2$-$C_{10}$ alkene, $C_2$-$C_{10}$ alkyne, $C_1$-$C_{10}$ nitrile, $C_1$-$C_{10}$ alcohol, $C_1$-$C_{10}$ thiol, $C_6$-$C_{10}$ phenol, $C_4$-$C_{10}$ aryl, or $C_5$-$C_{10}$ heteroaryl; and z, n, o, p and q independently are 0 to 10, and more typically at least one of z, n, o, p and q is 1. An example of a crosslinker satisfying Formulas V and VI is provided below

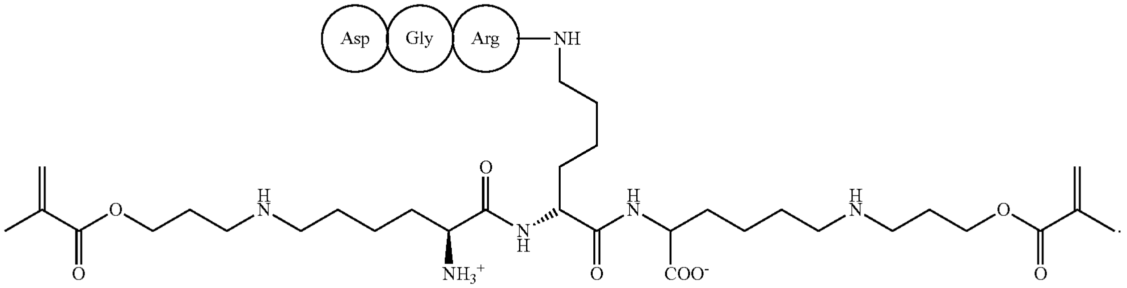

Crosslinkers according to the present invention are used to make hydrogels, such as a hydrogel having a Formula VII (Monomer 1)$_k$-(Crosslinker 1)$_l$-(Monomer 2)$_m$ Formula VII.

With reference to Formula VII, monomer 1 and monomer 2 are independently provided by an acrylate, alkyl acrylate, acrylamide, alkyl acrylamide, acrylonitrile, alkyl acrylonitrile or a (hydroxyalkyl) acrylate; k and m are independently 0-1000; each crosslinker 1 is independently a crosslinker according to any of Formulas I-VI; and l is 1-100, more typically 1-10. Hydrogels are often made with monomer: crosslinker ratios of 100:1 to 0:1, with particular hydrogels having a ratio of at least as high as 52:1 and at least as low as 6:1. Exemplary specific monomers include 2-carboxyethyl acrylate, [2-(acryloyloxy) ethyl] trimethyl ammonium chloride, 3-sulfopropyl methacrylate, [2-(methacryloyloxy) ethyl] trimethyl ammonium chloride, N-(methacryloxyethyl)-N,N-dimethyl-N-(2-methylcarboxyl)ammonium betaine, N-(methacryloxyethyl)-N,N-dimethyl-N-3-sulfopropyl)ammonium betaine, and 2-methacryloyloxyethyl phosphorylcholine. Examples of hydrogels according to the present invention include:

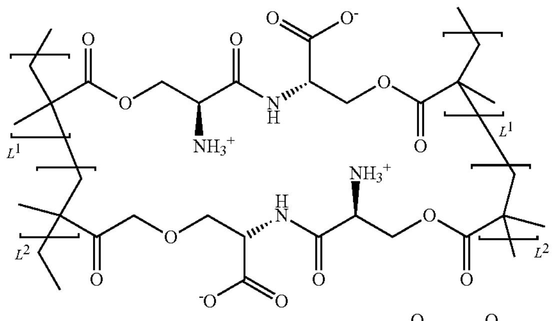

,

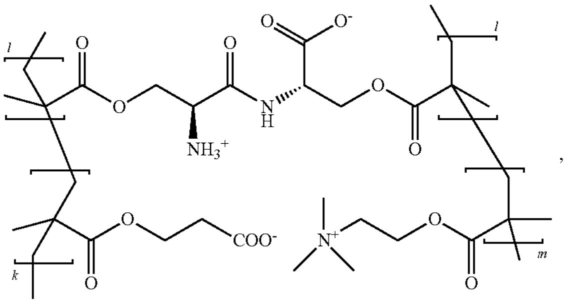

,

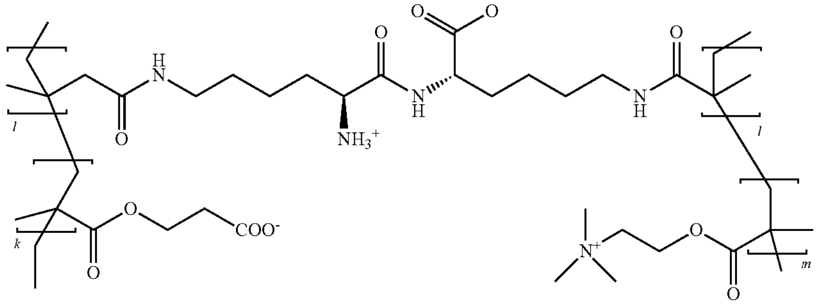

,

-continued
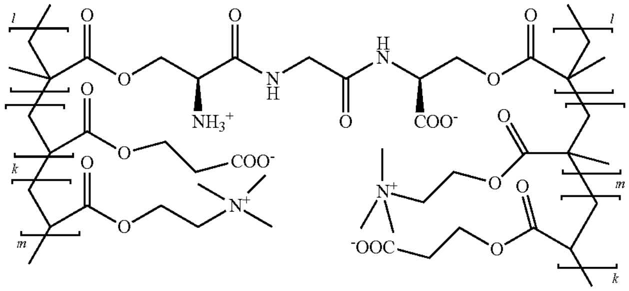
,
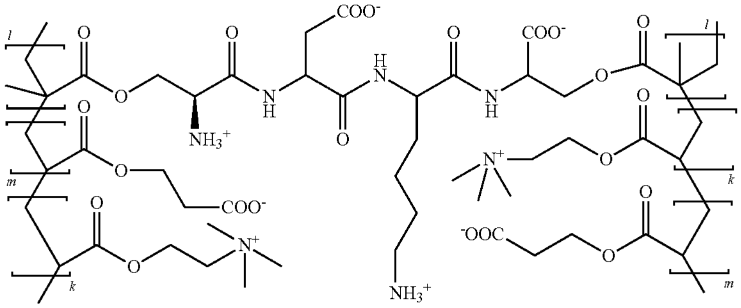
,
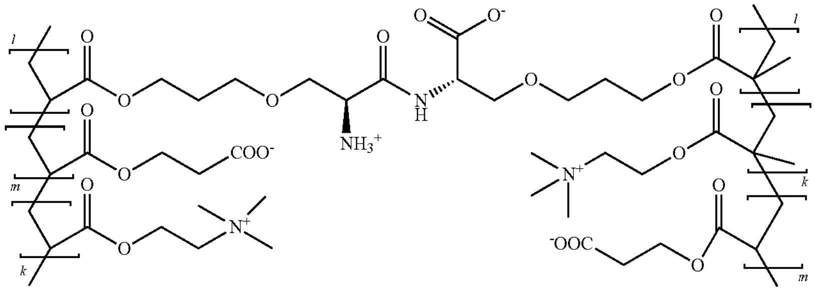
,
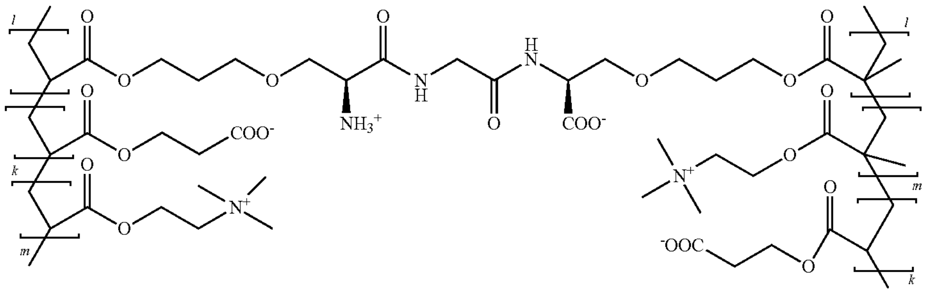
,
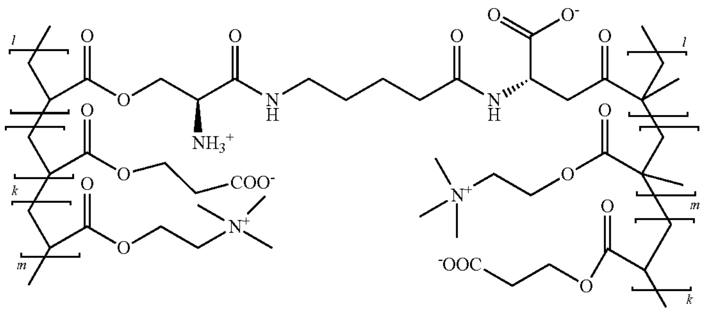
,

-continued

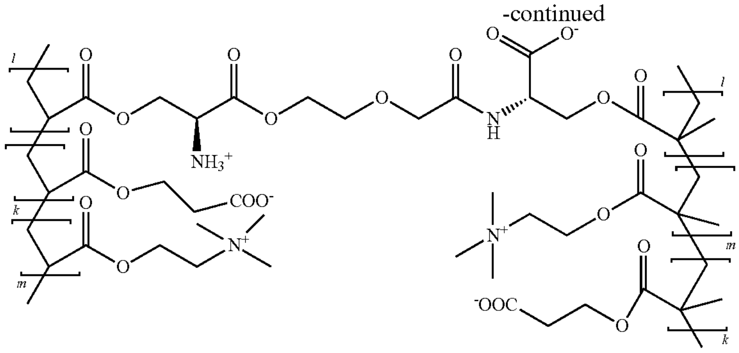

,

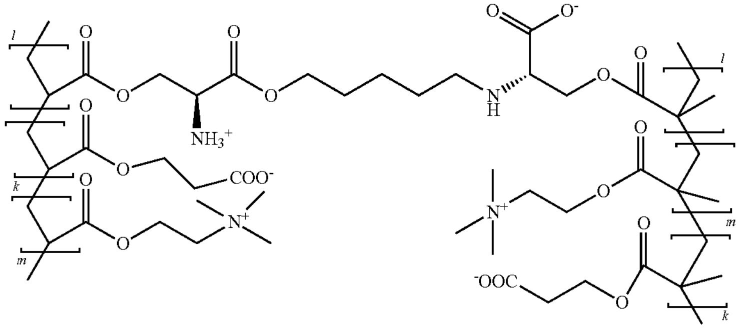

,

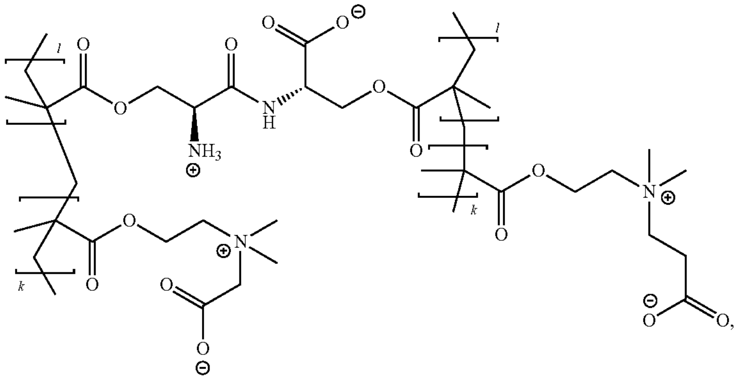

, and

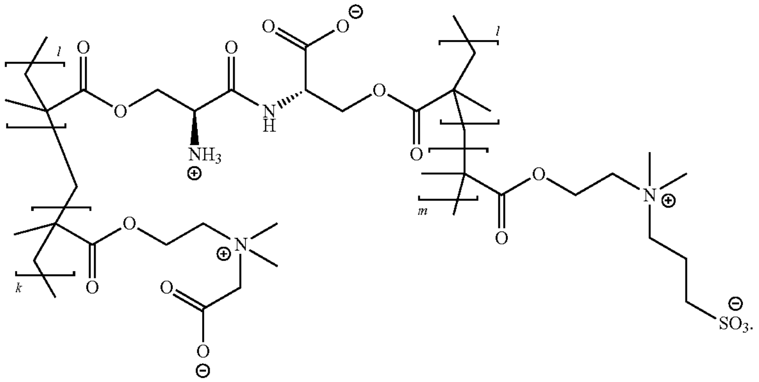

The present invention also concerns a method for making disclosed crosslinkers. One embodiment of a method for making a crosslinker according to the present invention comprises providing a first protected amino acid comprising a tert-butoxycarbonyl (Boc) protected amine functional group, a t-butyl ester protected carboxylic acid functional group, and a reactive functional group capable of reacting with a first polymerizing group. The first protected amino acid is reacted with a first polymerizing group selected from acrylate, alkyl acrylate, acrylamide, alkyl acrylamide, acrylonitrile, alkyl acrylonitrile or a (hydroxyalkyl) acrylate to provide a protected amino acid coupled through the reactive functional group to the first polymerizing group. The amine protecting group is selectively removed from the first protected amino acid, such as by using trifluoracetic acid. A second protected amino acid is provided that comprises a Boc-protected amine functional group, an unprotected carboxylic acid functional group, and a reactive functional group capable of reacting with a second polymerizing group. The second protected amino acid is reacted with a second polymerizing group selected from acrylate, alkyl acrylate, acrylamide, alkyl acrylamide, acrylonitrile, alkyl acrylonitrile or a (hydroxyalkyl) acrylate to provide a second protected amino acid coupled through the reactive functional group to the second polymerizing group. A peptide bond is then formed between the first and the second amino acids, and remaining protecting groups are removed to form a crosslinker that is zwitterionic between a pH of from 2.5 to 10. The method can also involve forming a crosslinker comprising at least one spacer group.

A second embodiment of a method for making a crosslinker according to the present invention comprises providing a first protected amino acid that comprises a Boc-protected amine functional group, an unprotected carboxylic acid functional group, and a reactive functional group capable of reacting with a first polymerizing group. The first protected amino acid is reacted with a first polymerizing group selected from acrylate, alkyl acrylate, acrylamide, alkyl acrylamide, acrylonitrile, alkyl acrylonitrile or a (hydroxyalkyl) acrylate to provide an amine protected amino acid coupled through its reactive functional group to the first polymerizing group. The carboxylic acid functional group is protected as a t-butyl ester. The amine protecting group is selectively removed from the first protected amino acid, such as by using trifluoracetic acid, to provide an unprotected amine functional group. A second protected amino acid is provided that comprises a Boc-protected amine functional group, an unprotected carboxylic acid functional group, and a reactive functional group that is capable of reacting with a second polymerizing group. The second protected amino acid is reacted with a second polymerizing group selected from acrylate, alkyl acrylate, acrylamide, alkyl acrylamide, acrylonitrile, alkyl acrylonitrile or a (hydroxyalkyl) acrylate to provide a second amine protected amino acid coupled through its reactive functional group to the second polymerizing group. A peptide bond is formed between the first and the second amino acids, and remaining protecting groups are removed to form a crosslinker that is zwitterionic between a pH from 2 to 10. The method can also further comprise forming a crosslinker comprising at least one spacer group.

A method for making a hydrogel also is disclosed comprising forming a hydrogel comprising disclosed crosslinker embodiments. The method may comprise providing a crosslinker according to any of Formulas I-VI, and reacting the crosslinker with a first monomer and a second monomer to form a crosslinked hydrogel. This process can be performed as a "one pot" reaction. The first monomer may be structurally identical to the second monomer, or the first monomer may have a first structure and the second monomer a second structure.

Zwitterionic hydrogels of the present invention can be used to form products comprising the hydrogel. The disclosed hydrogels, and hence products comprising such hydrogels, address fouling and bacteria adhesion issues associated with previously known hydrogels. Accordingly, such products are particularly suitable for biomedical applications, such as contact lenses, drug delivery vehicles, tissue engineering platforms, tissue regeneration platforms, catheters, implants and sensors.

The foregoing and other objects, features, and advantages of the invention will become more apparent from the following detailed description, which proceeds with reference to the accompanying figures.

DETAILED DESCRIPTION

I. Terms and Definitions

Figure 1:
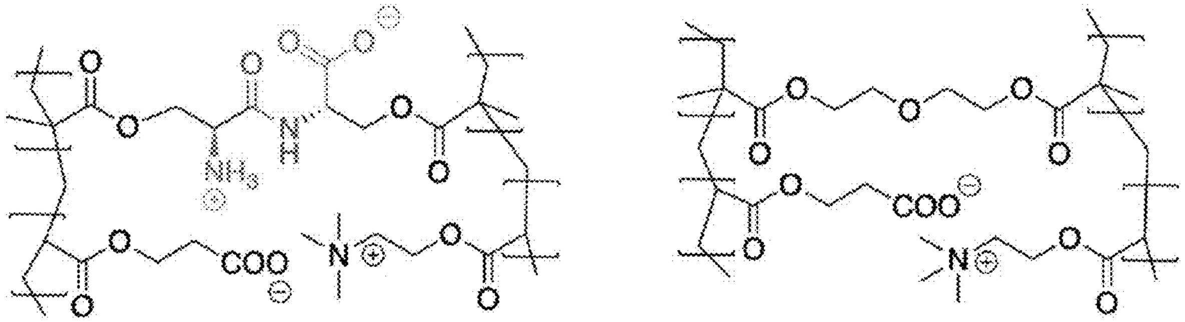
FIG. 1 illustrates an exemplary hydrogel according to the present invention comprising an N-Ser-Ser-C dimethacrylate (S—S) crosslinker and compares that structure to a hydrogel comprising a diethylene glycol dimethacrylate (DEG) crosslinker to highlight similarities in the overall crosslinker lengths (10 versus 9 backbone atoms, respectively).

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges refers to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word “about” is recited.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

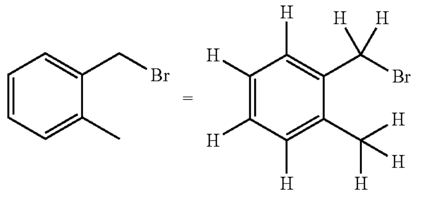

Sometimes a particular atom in a structure is described in textual formula as having a hydrogen or hydrogen atoms, for example $—CH_2CH_2—$. It will be understood by a person of ordinary skill in the art that the aforementioned descriptive techniques are common in the chemical arts to provide brevity and simplicity to description of organic structures.

If an R group is depicted as “floating” on a ring system and not directly bonded to the structure, as for example in the group:

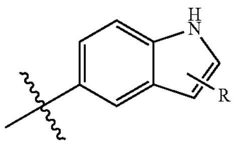

then, unless otherwise defined, a substituent R can reside on any atom so long as a stable structure is formed that conforms to standard valence conditions as understood by a person of ordinary skill in the art. In the example depicted, the R group can reside on an atom in either the 5-membered or the 6-membered ring of the indolyl ring system, including the heteroatom by replacing the explicitly recited hydrogen, but excluding the atom carrying the bond with the “∿” symbol and the bridging carbon atoms.

When there are more than one such depicted “floating” groups, as for example in the formulae:

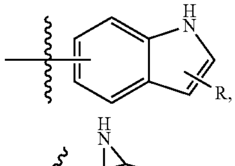

, or

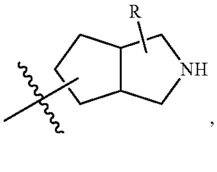

, or

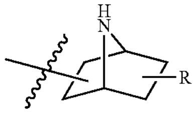

where there are two groups, namely, the R and the bond indicating attachment to a parent structure; then, unless otherwise defined, each “floating” group can reside on any atoms of the ring system, again assuming each replaces a depicted, implied, or expressly defined hydrogen on the ring system and a chemically stable compound would be formed by such an arrangement.

Alcohol: An organic compound including at least one hydroxyl group. Alcohols may be monohydric (including one —OH group), dihydric (including two —OH groups; diols, such as glycols), trihydric (including three —OH; triols, such as glycerol) groups, or polyhydric (including three or more —OH groups; polyols). The organic portion of the alcohol may be aliphatic, cycloaliphatic (alicyclic), heteroaliphatic, cycloheteroaliphatic (heterocyclic), polycyclic, aryl, or heteroaryl, and may be substituted or unsubstituted.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term “lower aliphatic” refers to an aliphatic group containing from one to ten carbon atoms. An aliphatic chain may be substituted or unsubstituted. Unless expressly referred to as an “unsubstituted aliphatic,” an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkoxy: A radical (or substituent) having the structure —OR, where R is a substituted or unsubstituted alkyl. Methoxy ($—OCH_3$) is an exemplary alkoxy group. In a substituted alkoxy, R is alkyl substituted with a non-interfering substituent. “Thioalkoxy” refers to —S—R, where R is substituted or unsubstituted alkyl. “Haloalkyloxy” means a radical —OR where R is a haloalkyl.

Alkyl: A saturated aliphatic hydrocarbyl group having any number of carbon atoms, but for purposes of the present disclosure typically includes from 1 to 25 ($C_{1-25}$) or more carbon atoms, more typically 1 to 10 ($C_{1-10}$) carbon atoms such as 1 to 6 ($C_{1-6}$) carbon atoms or 1 to 4 ($C_{1-4}$) carbon atoms. An alkyl moiety may be substituted or unsubstituted. Alkyl includes, by way of example, linear and branched hydrocarbyl groups such as methyl ($CH_3$), ethyl ($—CH_2CH_3$), n-propyl ($—CH_2CH_2CH_3$), isopropyl ($—CH(CH_3)_2$), n-butyl ($—CH_2CH_2CH_2CH_3$), isobutyl ($—CH_2CH_2(CH_3)_2$), sec-butyl ($—CH(CH_3)(CH_2CH_3)$), t-butyl ($—C(CH_3)_3$), n-pentyl ($—CH_2CH_2CH_2CH_2CH_3$), and neopentyl ($—CH_2C(CH_3)_3$). Lower alkyl means that the alkyl chain includes 1-10 carbon atoms. The terms alkenyl and alkynyl refer to hydrocarbon groups having carbon chains containing one or more double or triple bonds, respectively.

Alkylamino: A chemical functional group —N(H)R, where R is an alkyl group.

Alkylammonium: A cation having a formula $[N(H)(R')_3]^+$ where each R' independently is H or alkyl.

Amide: An organic compound characterized by a carbonyl group (C═O) linked to a nitrogen atom and having the following general formula, where R, R' and R" are the same or different, and typically are selected from hydrogen, aliphatic, and aryl.

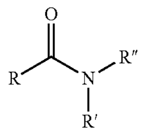

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is $—NH_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like.

Amino Acid: An organic acid containing both a basic amino group ($—NH_2$) and an acidic carboxyl group (—COOH). The 25 amino acids that are protein constituents are α-amino acids, i.e., the $—NH_2$ group is attached to the carbon atom next to the —COOH group.

Aminoalkyl: A chemical functional group $—RNH_2$ where R is an alkyl group.

Ammonium: A cation having a formula $[NR_4]^+$ where each R independently is H or aliphatic, more typically H or alkyl, such as $C_1$-$C_6$ alkyl.

Carboxyl: A —COOH radical. Substituted carboxyl refers to —COOR where R is aliphatic, heteroaliphatic, alkyl, heteroalkyl, or a carboxylic acid or ester.

Carboxylic Acid: A carbonyl-bearing functional group having a formula RCOOH where R is aliphatic, heteroaliphatic, alkyl, or heteroalkyl.

Counter ion(s): The ion, or ions, accompanying another ionic species to provide electric neutrality. For example, in NaOH, $Na^+$ is the counterion to $OH^-$.

Heteroalkyl: An alkyl or cycloalkyl radical having at least one carbon atom in the chain and containing at least one heteroatom, such as N, O, S, or $S(O)_n$ (where n is 1 or 2).

Heteroaliphatic: An aliphatic compound or group having at least one carbon atom in the chain and at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Hydrogel: A crosslinked, three-dimensional network of polymeric chains that are capable of absorbing and retaining molecules (e.g., water, polar solvents, non-polar solvents, drugs in liquid or solid form, or the like) in their three-dimensional networks. Hydrogel-forming polymeric chains comprise one or more hydrophilic functional groups in their polymeric structures, such as amino ($NH_2$), hydroxyl (OH), amide (—CONH—, $—CONH_2$), sulfate ($—SO_3H$), or any combination thereof, and can be natural-, or synthetic-polymeric-based networks. In some embodiments, the polymeric chains can comprise a plurality of the same monomeric units. In other embodiments, the polymeric chains can comprise a plurality of different monomeric units. Exemplary hydrogels may include, but are not limited to, proteins (e.g., collagen, gelatin, or the like), denatured proteins (e.g., methacrylated gelatin [GelMA], methacrylated collagen [Col-MA], or the like), polysaccharide (chitosan, starch, alginate, or the like), synthetic hydrogels (e.g., poly(ethylene glycol) diacrylate [PEGDA]).

Hydroxyalkyl: An alkyl group as defined above substituted with at least one hydroxyl group, provided that if two or more hydroxyl groups are present no two hydroxyl groups are on the same carbon atom.

Isomer: One of two or more molecules having the same number and kind of atoms, but differing in the arrangement or configuration of the atoms. Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture."

Lower: Refers to organic compounds having 10 or fewer carbon atoms in a chain, including all branched and stereochemical variations, particularly including methyl, ethyl, propyl, butyl, pentyl, hexyl, heptyl, octyl, nonyl, and decyl.

Polypeptide: A polymer in which the monomers are amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Protecting or Protective Group: To synthesize organic compounds, often some specific functional group cannot survive the required reagents or chemical environments. These groups must be protected. A protecting group, or protective group, is introduced into a molecule by chemical modification of a functional group in order to obtain chemoselectivity in a subsequent chemical reaction. Various exemplary protecting or protective groups are disclosed in Greene's Protective Groups in Organic Synthesis, by Peter G. M. Wuts and Theodora W. Greene (Oct. 30, 2006), which is incorporated herein by reference.

Stereochemistry: The three-dimensional spatial configuration of a molecule.

Stereoisomers: Isomers that have the same molecular formula and sequence of bonded atoms, but which differ only in the three-dimensional orientation of the atoms in space.

Substituted: A fundamental compound, such as an aryl or aliphatic compound, or a radical thereof, having coupled thereto one or more substituents, each substituent typically replacing a hydrogen atom on the fundamental compound. A person of ordinary skill in the art will recognize that compounds disclosed herein may be described with reference to particular structures and substituents coupled to such structures, and that such structures and/or substituents also can be further substituted, unless expressly stated otherwise or context dictates otherwise. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

II. Overview

Certain disclosed embodiments of the present invention concern an amino-acid or peptide-based based crosslinker molecule comprising polymerizable groups that are designed for producing hydrogels that have a broad range of applications, including biomedical applications. One advantage of the family of disclosed crosslinkers is the presence of charged regions, with overall charge neutrality at biological pH and more particularly charge neutrality between a pH of about 2.5 to 10, provided by zwitterionic species. As currently understood, no previously known crosslinkers comprise naturally occurring amino acids that incorporate charged functionalities into the backbone portion of the crosslinker.

A number of variables are afforded by the present crosslinkers and corresponding hydrogels that allow the properties of such compounds to be adjusted for particular end-use applications. A first variable that can be controlled is the counterion species used during the purification prior to application. For example, for certain embodiments disclosed by the present application, the final molecule underwent ion-exchange to provide an HCl counter ion. The counter ion may impact the solubility of crosslinkers in various solvents during its incorporation into hydrogels.

A second variable is the composition of the base amino acids or peptide sequences that are selected to make the crosslinkers. The selection of amino acids or peptide sequences influence the mechanical properties of the hydrogel they are incorporated into.

A third variable is the composition of the polymerizing group. Appropriate selection of polymerization groups broadens the potential end-use applications where disclosed crosslinkers and corresponding hydrogels can be utilized.

A fourth variable is the selection of protecting groups used during synthesis. Significant effort was used to identify the protection strategy for disclosed embodiments of the present invention.

III. Compounds

A. Zwitterionic Crosslinkers

1. General Crosslinker Formulas

Certain disclosed embodiments of the present invention concern zwitterionic compounds that are useful, amongst other things, as crosslinkers for forming hydrogels. A first Formula I describing crosslinkers according to the present disclosure is provided below.

(Polymerizing Group 1)$_s$-(Amino Acid)$_u$-(Polymerizing Group 2)$_y$ Formula I The primary components of compounds within the scope of Formula I are polymerizing groups, such as polymerizing groups 1 and 2, and amino acids.

Polymerizing group 1 and polymerizing group 2 can be selected independently such that polymerizing group 1 and polymerizing group 2 can be the same or different. Polymerizing group 1 and polymerizing group 2 can be any known compound or functional group that provides functionality suitable for further polymer extension or coupling to relevant components of a hydrogel, as discussed in more detail below. Examples of suitable polymerizing groups include acrylate, alkyl acrylate, acrylamide, alkyl acrylamide, acrylonitrile, alkyl acrylonitrile or a (hydroxyalkyl) acrylate. More particularly, examples of suitable polymerizing groups include methacrylate, ethylacrylate, propylacrylate, methacrylamide, ethylacrylamide, propylacrylamide, methacrylonitrile, ethylacrylonitrile, propylacrolynitrile or (hydroxyethyl)methacrylate. Certain exemplary embodiments of the present invention have been alkyl-acrylate and alkyl-acrylamide based compounds, as shown below in Table 1. The number of polymerizing groups is indicated by s and y, where s and y are from 1 to 10, more typically 1 to 5, and even more typically 1.

General Formula I indicates that suitable crosslinkers according to the present invention include amino acids, and the number of amino acids is designated by u, where u is at least 2, such as 2 to 100, more typically 2 to 50, even more typically 2-10, such as 2-6. As with the polymerizing groups, the amino acids can be selected independently, such that the amino acids can be the same, or two or more different amino acids can be used to form suitable crosslinkers. In general, amino acids suitable for the present invention can be any amino acid, including naturally occurring and non-naturally occurring amino acids. However, amino acids that include defining functional groups that are charged at a pH from 2.5 to 10 and/or that allow further conjugation without requiring additional intermediate functionalization are preferred, such as serine, lysine, aspartic acid, glutamic acid, arginine, histidine, cysteine, threonine, and tyrosine. Amino acids such as glycine, alanine, valine, leucine, isoleucine, etc., do not include an easily functionalizable group; however, these amino acids could be modified for use according to the present invention, such as by first undergoing halogenation followed by addition of a functionalizable group, such as —OH, —SH —$NH_2$, alkene, alkyne, etc.

Suitable amino acids can include achiral centers and exist as stereoisomers, or can be achiral. For amino acids that include stereoisomers, each amino acid can be used as substantially a pure single isomer, such as a D or L (R or S) isomer, or can be used as a mixture of isomers where the isomers are present in substantially equal proportions or one isomer can be present in excess of the other [an enantiomeric excess (ee)]. Moreover, the amino acid can be naturally occurring, non-naturally occurring, an α-amino acid, a β-amino acid, etc. One notable aspect of disclosed embodiments is that the crosslinker species are zwitterions, typically including positively charged ammonium ions and negatively charged carboxylate ions. Exemplary embodiments of crosslinker species according to the present invention are formed primarily using serine, lysine, aspartic acid, glutamic acid, arginine, histidine, cysteine, threonine, and tyrosine, and any and all combinations thereof. Amine and ammonium components of disclosed hydrogels can be primary, secondary, tertiary or quaternary.

Table 1 below provides examples of crosslinkers satisfying Formula I, and subsequently disclosed general formulas. An example of a crosslinker having two identical amino acids is provided by Ser-Ser-dimethacrylate, and Lys-Lys-dimethacrylate. Several of the exemplary crosslinker species provided by Table 1 below include more than 2 amino acids. An example of a crosslinker satisfying Formula I and having different amino acids, where u=3, is provided by Ser-Gly-Ser-dimethacrylate. Another example of a crosslinker having more than two amino acids is provided by Ser-Asp-Gly-Gly-Lys-Ser-dimethacrylate, where u=6.

Crosslinkers according to the present invention also may include a spacer or spacers. In general, there are two types of spacers: external spacers that are positioned outside the zwitterionic component, such as amino acids or peptides; and internal spacers that are positioned in between one or more zwitterionic components. General formulas describing crosslinker embodiments according to the present invention comprising spacers are provided below. Each of the following general formulas can include the amino acid and polymerizing groups and variables as discussed above for Formula 1. Components and number variables that are common between formulas disclosed herein are as stated above for Formula I.

Crosslinkers solely having an internal spacer may have a Formula II.

[(Polymerizing Group 1)$_s$-(Amino Acid 1)$_u$-(Internal Spacer)$_v$-(Amino Acid 2)$_w$-(Polymerizing Group 2)$_y$] Formula II Crosslinkers solely comprising one or more external spacers may have a Formula III.

[(Polymerizing Group 1)$_s$-[(External Spacer 1)$_t$-(Amino Acid)$_u$-(External Spacer 2)$_x$]-(Polymerizing Group 2)$_y$] Formula III With reference to Formulas II and III, as with the polymerizing groups and amino acids discussed previously, for crosslinkers having multiple spacers, each such spacer can be selected independently. Accordingly, the spacer moieties can all be structurally identical, they can all be structurally different, or some spacers can be structurally identical and some spacers can be structurally different. Suitable spacers, particularly internal spacers, also may be amino acids or peptides since they can be conveniently created using common peptide chemistries. Internal spacers can also be amino-acid like but with changed functionality, such as esters versus amides or C—C bonds. Amino-acid based spacers can also be used and can comprise non-natural amino acids, such as DL, D, or L-2,3-diaminopropanoic acid, 2,4-diaminobutanoic acid, ornithine, 2-aminohexanedioic acid, similar structures, and combinations thereof.

The spacers need not be amino acids or peptides. Suitable non-amino acid spacers typically are aliphatic or heteroaliphatic, including alkanes, heteroalkenes, alkenes, heteroalkenes, alkynes, heteroalkynes, cyclic, heterocyclic, aryl, and heteroaryl spacers. Certain disclosed embodiments of compounds within the scope of Formulas were formed using alkyl and heteroalkyl spacer groups, including spacers having one or more oxygen atoms, sulfur atoms, nitrogen atoms, and/or phosphorous atoms, and combinations thereof. Each spacer can include a variable number of atoms, but typically has from 1 to 20 atoms, more typically 2 to 10 atoms, and even more particularly 4-8 atoms. Particular examples of spacers include alkyl groups and heteroalkyl groups, including glycols, such as $C_1$-$C_{20}$ alkyl and heteroalkyl groups, more typically $C_1$-$C_{10}$ alkyl and heteroalkyl groups, such as $C_2$-$C_6$ alkyl and heteroalkyl groups, with particular spacer examples including alkyl hydrocarbons, such as methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), and hexylene (—$CH_2CH_2CH_2CH_2CH_2CH_2$—); and glycols, or compounds similar to glycols, such as

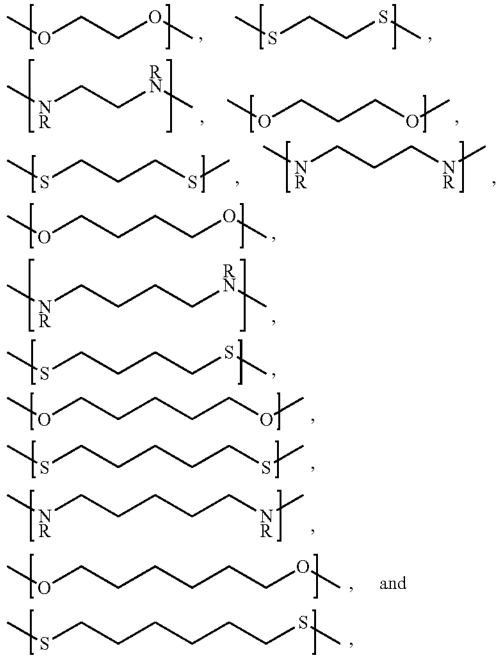

and where R is independently selected from H and lower alkyl, typically $C_1$-$C_{10}$ alkyl, more typically $C_1$-$C_6$ alkyl, such as methyl or ethyl. Any of these exemplary spacers can include combinations of heteroatoms too, for example,

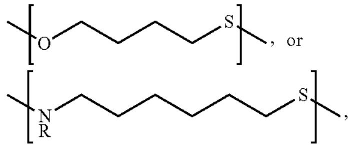

or or a single heteroatom, such as with

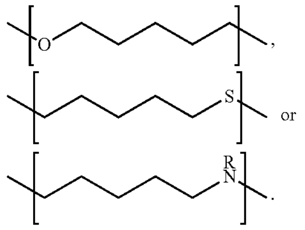

or

Amides, esters and thioesters also can be suitable spacers. Examples of such spacers include

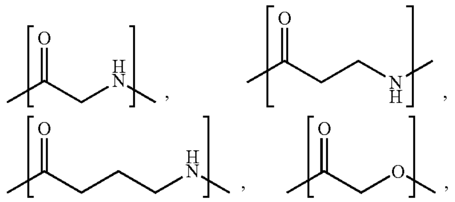

-continued

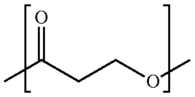,
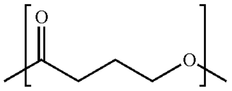,
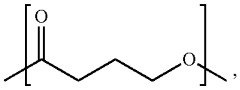,
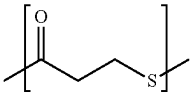,
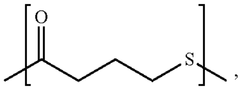,
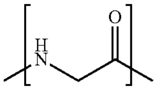,
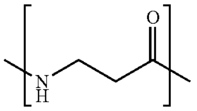,
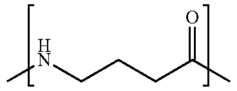,
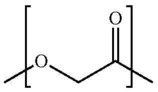,
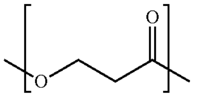,
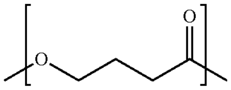,
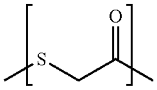,
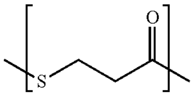, and
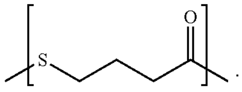.

Formulas II and III include the variables s and y to designate the number of polymerizing groups, where s and y are from 1 to 10, more typically 1 to 5, and even more typically 1. The number of amino acids is designated by the variables u and w, where u and w sum to at least 2, and are independently 0 to 100, such as 2 to 100, more typically 2 to 50, even more typically 2-10, such as 2-6. The number of internal spacers is designated by the variable v, and the number of external spacers 1 and 2 is designated by the variables t and x. For crosslinkers having no spacers, then t, v and x are 0. For crosslinkers having at least one internal spacer but no external linkers, then t and x are 0, and v is at least 1, typically 1 to 20, more typically 1 to 10, and even more typically 1 to 5. Where v is 2 or more, then each of the internal spacers can be selected independently. For crosslinkers having only external spacers, and no internal spacers, then at least one oft and x is 1 or more, typically 1 to 20, more typically 1 to 10, and even more typically 1 to 5, and v is 0. As with the internal spacer, if t and/or x is 2 or more, then each of the spacers can be selected independently. Finally, crosslinkers according to the present invention can include both internal and external spacers. In these situations, each such spacer can be selected independently and v is at least one and at least one oft and x is at least one, typically 1 to 20, more typically 1 to 10, and even more typically 1 to 5.

Yet another general formula describing crosslinkers according to the present invention is Formula IV.

[(Polymerizing Group 1)$_s$-(Spacer 1)$_t$-(Amino Acid 1)$_u$-(Spacer 2)$_v$-(Amino Acid 2)$_w$-(Spacer 3)$_x$-(Polymerizing Group 2)$_y$] Formula IV Again, as stated above, the primary components of compounds within the scope of Formula IV are polymerizable groups, such as the polymerizing group 1 and polymerizing group 2, amino acids, such as amino acid 1 and amino acid 2, and a spacer or spacers, if present, indicated as spacer 1, spacer 2 and spacer 3. Furthermore, and again as stated above, polymerizing group 1 and polymerizing group 2 can be selected independently such that polymerizing group 1 and polymerizing group 2 can be the same or different. These polymerizing groups are typically an acrylate, alkyl acrylate, acrylamide, alkyl acrylamide, acrylonitrile, alkyl acrylonitrile or a (hydroxyalkyl) acrylate. S and y typically=1. However, the number of polymerizing groups can vary, as indicated by the variables s and y in Formula IV. Accordingly branched-end crosslinkers, where at least one of s and y is two or more, and potentially both of s and y are two or more, also are within the scope of Formula IV.

General Formula IV indicates that crosslinkers according to the present invention comprise amino acid 1 and amino acid 2. This is to indicate that disclosed crosslinkers typically include at least 2 amino acids. The designations “amino acid 1” and “amino acid 2” should not be interpreted to mean that amino acid 1 and amino acid 2 are required to be structurally distinct from each other. Instead, amino acid 1 and amino acid 2 can be selected independently, such that amino acid 1 can be the same as amino acid 2, or two different amino acids can be used to form suitable crosslinkers.

General Formula IV also includes subscripts u and w, indicating that suitable crosslinkers can include more than one amino acid 1 by the subscript u, and/or can include more than one amino acid 2, by the subscript w. u and w sum to at least 2. Each of the plural amino acid 1 and/or plural amino acid 2 likewise can be independently selected to be either the same amino acid or different amino acids. Several of the exemplary crosslinker species provided by Table 1 below include more than 2 amino acids. See, for example, the crosslinker Ser-Asp-Lys-Ser. As stated above with reference to Formulas I-III, Amino Acid 1 and Amino Acid 2 can be any amino acid, including naturally occurring and non-naturally occurring amino acids. However, amino acids that include defining functional groups that are charged at a pH from 2.5 to 10, and more particularly at physiological pH, and/or that allow further conjugation without requiring additional intermediate functionalization are preferred, such as serine, lysine, aspartic acid, glutamic acid, arginine, histidine, cysteine, threonine, and tyrosine. Amino acids such as glycine, alanine, valine, leucine, isoleucine, etc., do not include an easily functionalizable group; however, these amino acids could be modified for use according to the present invention, such as by first undergoing halogenation followed by addition of a functionalizable group, such as —OH, —SH —$NH_2$, alkene, alkyne, etc. The amino acids can include achiral centers and exist as stereoisomers, or can be achiral. For amino acids that include stereoisomers, crosslinkers according to the present invention can be formed using substantially a pure single isomer, such as a D or L (R or S) isomer, or enantiomeric or diastereomeric mixtures of isomers can be used to form suitable crosslinkers. Moreover, the amino acid can be, but is not necessarily, an $\alpha$-amino acid. One notable aspect of disclosed embodiments is that the crosslinker species are zwitterions, typically including positively charged ammonium ions and negatively charged carboxylate ions.

Formula IV includes a spacer or spacers, for example external spacers 1 and 3, and internal spacer 2. Suitable spacers are described above with reference to Formulas II-III. As with polymerizing groups 1 and 2 and amino acids 1 and 2, spacer 1, spacer 2, and spacer 3 can be selected independently, and therefore the spacer moieties can all be structurally identical, they can all be structurally distinct, or some spacers can be structurally identical and some spacers can be structurally different.

Formula IV includes the subscripts t, v and x. For crosslinkers having no spacers, then t, v and x are each=0. For crosslinkers having at least one internal spacer but no external linkers, then t and x are 0, and v is at least 1, typically 1 to 20, more typically 1 to 10, and even more typically 1 to 5. Where v is 2 or more, then each of the internal spacers can be selected independently. For crosslinkers having only external spacers, and no internal spacers, then at least one of t and x is 1 or more, typically 1 to 20, more typically 1 to 10, and even more typically 1 to 5, and v is 0. As with the internal spacer, if t and/or x is 2 or more, then each of the spacers can be selected independently. Finally, crosslinkers according to the present invention can include both internal and external spacers. In these situations, each such spacer can be selected independently and at least one oft and x is at least 1, and v is at least 1, typically 1 to 20, more typically 1 to 10, and even more typically 1 to 5.

Crosslinkers according to the present invention can also include pendant side chains as illustrated by general Formula V below.

Formula V

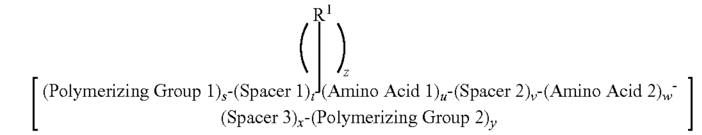

$R^1$ in Formula V is not coupled to a particular group; instead $R^1$ is "floating" above the formula to indicate that $R^1$ can be joined to any suitable moiety defined by the remaining structure. The $R^1$ side chain can be any of a variety of structural components comprising various different functional groups including, but not limited to, amines, carboxylic acids, alkynes, nitriles, alkenes, alcohols, thiols, phenols, aryl or substituted aryl, or any other functionalizable unit. The side chain length is typically a $C_1$-$C_{10}$ chain, for example a $C_1$-$C_{10}$ alkyl amine or $C_1$-$C_{10}$ carboxylic acid. Particular exemplary $R^1$ groups include $C_1$-$C_{10}NR^2R^3$ and $C_1$-$C_{10}CO_2R^4$, more typically a $C_1$-$C_6$ chain, such as a $C_1$-$C_6$-alkyl amine or $C_1$-$C_6$—COOH. Prior to any further conjugation, $R^2$-$R^4$ are independently selected from hydrogen and lower alkyl, typically hydrogen, with at least one of $R^2$ and $R^3$ being hydrogen to allow further conjugation. Subsequent to conjugation, if desired, $R^4$ may comprise an amino acid or peptide, such that at least one of $R^2$ and $R^3$ is an amino acid or peptide, and the remaining $R^2$ and $R^3$ is independently selected from hydrogen, alkyl, amino acids and peptides. One example of a crosslinker according to the present invention comprising an arginine-glycine-aspartic acid (RGD) and a $C_4$ alkyl amine pendant $R^1$ is provided below.

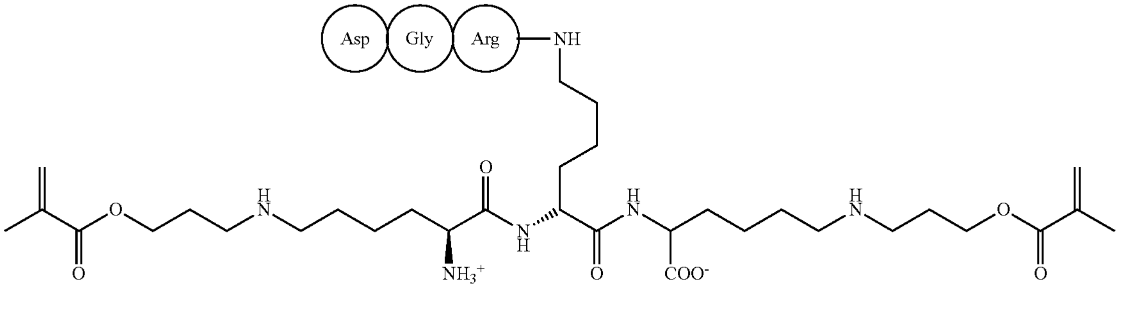

A person of ordinary skill in the art will appreciate that a number of additional pendant side chains can be included, such as a GROGER, GFOGER, GRGDSP (where the single letters correspond to amino acids) or similar side chain designed to promote cellular adhesion. This side-chain coupling strategy allows any peptide sequence to be incorporated into the crosslinker to accommodate significant biomedical applications.

Still with reference to Formula v, z can be 0 to 10, more typically 0 to 5, with certain disclosed embodiments having z=1. See, for example, Ser-Lys-Ser-dimethacrylate and Ser-Asp-Lys-Ser-dimethacrylate below in Table 1, where $R^1$ is $—CH_2CH_2CH_2CH_2NH_3^+$.

For certain disclosed crosslinker embodiments, crosslinkers can include 1 or more $R^1$ groups that can be independently selected, and therefore can be the same group or different combinations of groups. $R^1$ can be coupled to and extend from any one or more of amino acid 1, amino acid 2, spacer 1, spacer 2, and/or spacer 3, as shown below by general Formula VI, where the bond to $R^1$ is directly coupled to each of the indicated moieties, and $R^1$ is not "floating" as a general representation as indicated above for Formula V.

Formula VI

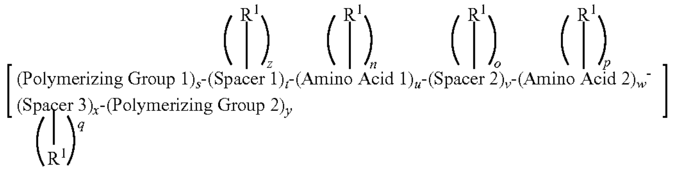

With reference to Formula VI, z, n, o, p and q independently are 0 to 10, more typically 0 to 5, with certain disclosed embodiments having at least one of z, n, o, p and q=1. The pendant moiety can be quite large. By including —COOH or $—NH_2$ termini, the crosslinker is available for further conjugation, such as with another peptide (e.g., RGD) or other biocompatible molecules.

Formulas V-VI also indicate the number of individual components included in the crosslinker assembly using variables. The s and y variables indicate the number of polymerizing groups, with z and y typically being 1, although compounds could be made with 2 or more polymerizing groups on each end of crosslinkers within the scope of the present invention. The number of spacer molecules are indicated by variables t, v and x, where t, v and x are from 0 to 20, more typically 0 to 10, and even more typically 0 to 5 or less. Suitable compounds within the scope of Formula VI can include no spacers, and in these situations t, v and x are 0. Compounds within Formula VI can include at least one internal spacer, i.e., a spacer that is positioned between amino acid 1 and amino acid 2, but no external spacers between amino acid 1 and amino acid 2 and polymerizing Groups 1 and 2, respectively. In these situations, t and x are 0, and v is 1 to 20, more typically 1 to 10, and even more typically 1 to 5. Similarly, compounds within Formula VI can include at least one external spacer and no internal spacers, and in these situations v=0, and at least one oft and x is at least 1, more typically t and x are both at least 1. Finally, compounds within Formula I can include both internal and external spacers, and in these situations, v is at least 1, and can be 1 to at least 20, more typically 1 to 10, and even more typically 1 to 5, and at least one oft and x is 1, and the remaining t and x are independently 0 to at least 20, more typically 1 to 10, and even more typically 1 to 5. For certain disclosed embodiments, anti-fouling properties of compounds within Formula VI are enhanced by increasing charge density, which can be achieved by excluding internal spacers, or including internal spacers where the size of the spacer and/or size of the spacers are limited.

The number of amino acids used to form compounds within Formula V and VI is indicated by u and w. Again, amino acids 1 and 2 can be independently selected, and can be the same or different. Accordingly, u and w sum to at least 2, and are independently 0 to 100, such as 1 to at least 20, typically 1 to 10, and even more typically 1 to 6.

As stated above, crosslinkers according to the present invention include polymerizing groups 1 and 2. An example of a Ser-Ser-bismethacrylate (methacrylate-serine-serine-methacrylate), Compound 1, is shown below.

Compound 1

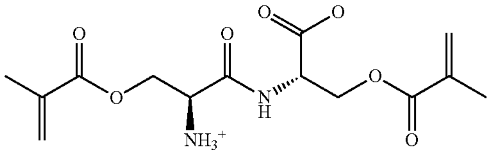

N-((S)-2-ammonio-3-(methacryloyloxy)propanoyl)-O-methacryloyl-L-serinate

Compound 1, fully synthesized and characterized, has been incorporated into an example hydrogel platform. Compound 1 provides several advantages over ethylene glycol crosslinkers, such as equal resistance to protein adsorption and cell adhesion and statistically better biodelivery performance.

The methacrylate components of Compound 1 could be varied, as will be understood by a person of ordinary skill in the art, to be within a homologous series, such as acrylate and ethacrylate, shown below as Compounds 2 and 3, respectively.

Compound 2

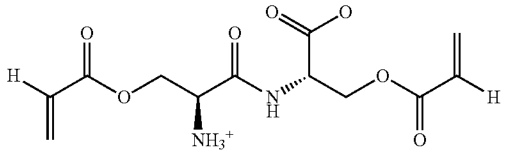

O-acryloyl-N-((S)-3-(acryloyloxy)-2-ammoniopropanoyl)-L-serinate

Compound 3

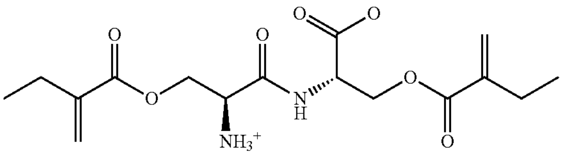

N-((S)-2-ammonio-3-((2-methylenebutanoyl)oxy)propanoyl)-O-(2-methylenebutanoyl)-L-serinate Instead of acrylates, Crosslinker compounds according to the present invention can be acrylamides within a homologous series, such as acrylamide, methacrylamide and ethacrylamide, shown below as Compounds, 4, 5, and 6, respectively.

Compound 4

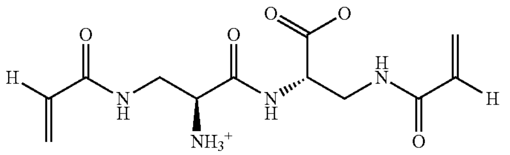

(S)-3-acrylamido-2-((S)-3-acrylamido-2-ammoniopropanamido)propanoate

-continued

Compound 5

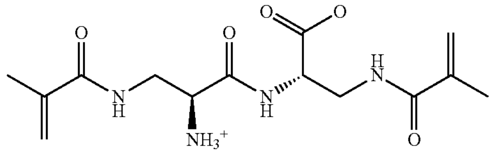

S)-2-((S)-2-ammonio-3-methacrylamidopropanamido)-3-methacrylamidopropanoate

Compound 6

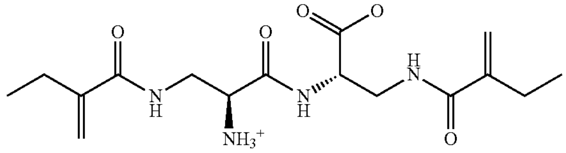

(S)-2-((S)-2-ammonio-3-(2-methylenebutanamido)propanamido)-3-(2-methylenebutanamido)propanoate Additional examples of bisacrylamides, and mixed acrylate/acrylamides, are provided below as Compounds 7-11.

Compound 7

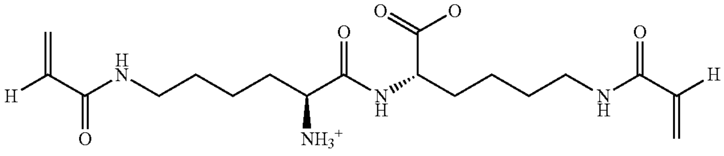

$N^2$-((S)-6-acrylamido-2-ammoniohexanoyl)-$N^6$-acryloyl-L-lysinate bis(Acrylamide)

-continued

Compound 8

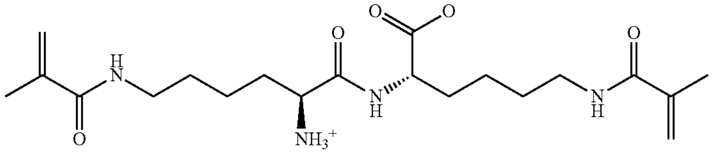

$N^2$-((S)-2-ammonio-6-methacrylamidohexanoyl)-$N^6$-methacryloyl-L-lysinate bis(Methacrylamide)

Compound 9

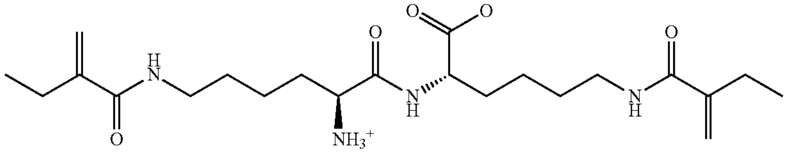

$N^2$-((S)-2-ammonio-6-(2-methylenebutanamido)hexanoyl)-$N^6$-(2-methylenebutanoyl)-L-lysinate bis(Ethacrylamide)

Compound 10

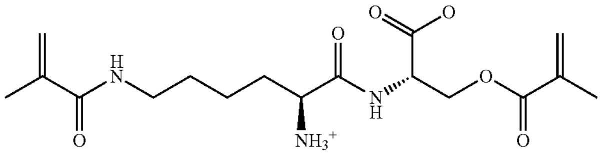

N-((S)-2-ammonio-6-methacrylamidohexanoyl)-O-methacryloyl-L-serinate

Mixed Methacrylamide and Methacrylate

Compound 11

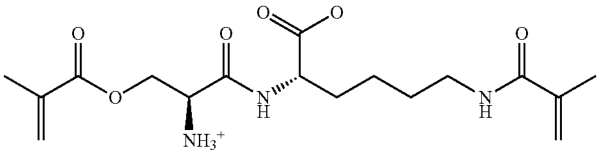

$N^2$-((S)-2-ammonio-3-(methacryloyloxy)propanoyl)-$N^6$-methacryloyl-L-lysinate Mixed Methacrylate and Methacrylamide Crosslinkers 12 and 13 illustrate varying the length of spacers with, for example, the addition of a propyl methacrylate group to both serine and lysine. A person of ordinary skill in the art will appreciate that any number of spacers, such as glycol spacers, may be added to alter the length and potentially the physical properties of hydrogels formed comprising such crosslinkers.

Compound 12

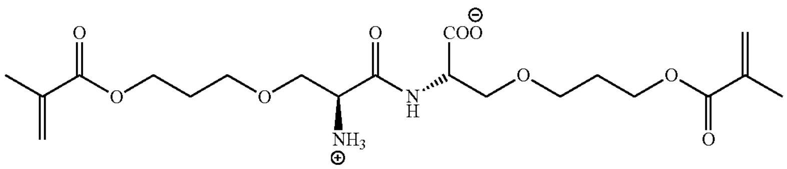

N-((S)-2-ammonio-3-(3-(methacryloyloxy)propoxy)propanoyl)-O-(3-(methacryloyloxy)propyl)-L-serinate -continued Compound 13

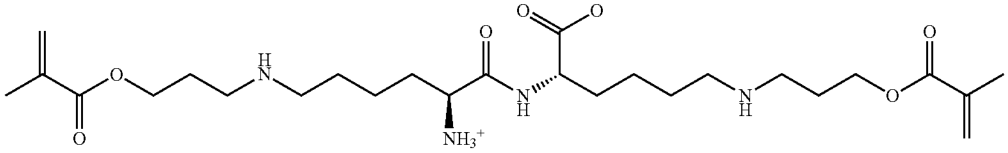

N2-((S)-2-ammonio-6-((3-(methacryloyloxy)propyl)amino)hexanoyl)-N6-(3-(methacryloyloxy)propyl)-L-lysinate B. Crosslinker Species Table 1 provides certain exemplary crosslinkers according to the present invention.

TABLE 1

| Structure/ChemDraw Name | Common Name and/or Comments |
|---|---|
| 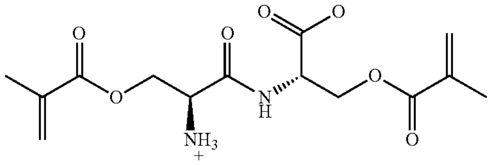 [SMILES: C=C(C)C(=O)OC[C@H](NC(=O)[C@@H](N)COC(=O)C(=C)C)C(=O)O] N-((S)-2-($\lambda^4$-azaneyl)-3-(methacryloyloxy)propanoyl)-O-methacryloyl-L-serinate | Ser-Ser-dimethacrylate or SS-dimethacrylate |
| 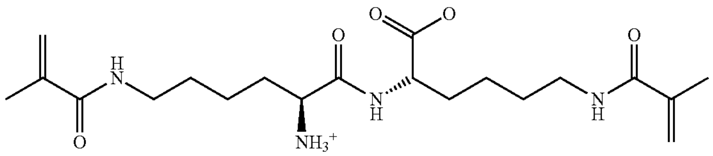 $N^2$-((S)-2-ammonio-6-methacrylamidohexanoyl)-$N^6$-methacryloyl-L-lysinate | Lys-Lys-dimethacrylate or KK-dimethacrylate |
| 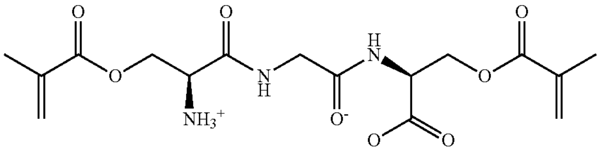 N-((S))-2-ammonio-3-(methacryloyloxy)propanoyl)glycyl)-O-methacryloyl-L-serinate | Ser-Gly-Ser-dimethacrylate (SGS) |
| 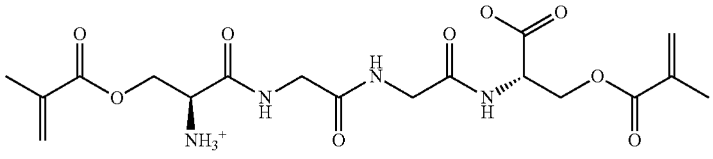 [SMILES: C=C(C)C(=O)OC[C@H](NC(=O)CNC(=O)CNC(=O)[C@@H]([NH3+])COC(=O)C(=C)C)C(=O)O] N-((S)-2-ammonio-3-(methacryloyloxy)propanoyl)glycylglycyl-O-methacryloyl-L-serinate | Ser-Gly-Gly-Ser-dimethacrylate (SGGS) |
| 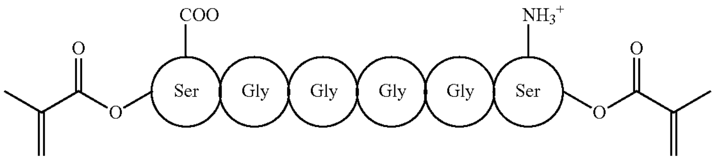 | Ser-Gly-Gly-Gly-Gly-Ser-dimethacrylate (SGGGS) |

TABLE 1-continued

| Structure/ChemDraw Name | Common Name and/or Comments |
|---|---|
| 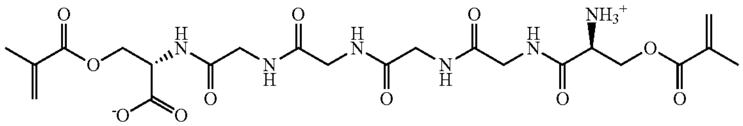<br>N-((S)-2-ammonio-3-(methacryloyloxy)propanoyl)glycylglycylglycylglycyl-O-methacryloyl-L-serinate | |
| 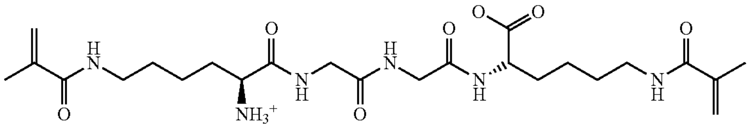<br>$N^2$-((S)-2-ammonio-6-methacrylamidohexanoyl)glycylglycyl-$N^6$-methacryloyl-L-lysinate | Lys-Gly-Gly-Lys dimethacrylate (KGGK) |
| 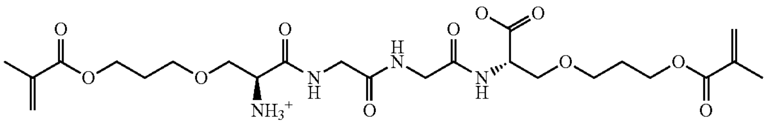 [SMILES: C=C(C)C(=O)OCCCOC[C@H](NC(=O)CNC(=O)CNC(=O)[C@@H]([NH3+])COCCCOC(=O)C(=C)C)C(=O)O]<br>N-((S)-2-ammonio-3-(3-(methacryloyloxy)propoxy)propanoyl)glycylglycyl-O-(3-(methacryloyloxy)propyl)-L-serinate | Ser-Gly-Gly-Ser-bis(propymethacrylate) (SGGS-ProGly) or SGGSPM |
| 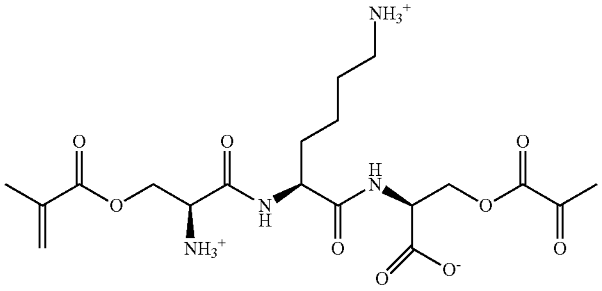 [SMILES: C=C(C)C(=O)OC[C@H]([NH3+])C(=O)N[C@@H](CCCC[NH3+])C(=O)N[C@@H](COC(=O)C(C)=O)C(=O)[O-]]<br>N-((S)-6-ammonio-2-((S)-2-ammonio-3-(methacryloyloxy)propanamido)hexanoyl)-O-methacryloyl-L-serinate | Ser-Lys-Ser-dimethacrylate (SKS) Provides an example of a crosslinker having a pendant side chain that can be used to couple additional amino acids or biomolecules, while keeping the backbone charge neutral |
| 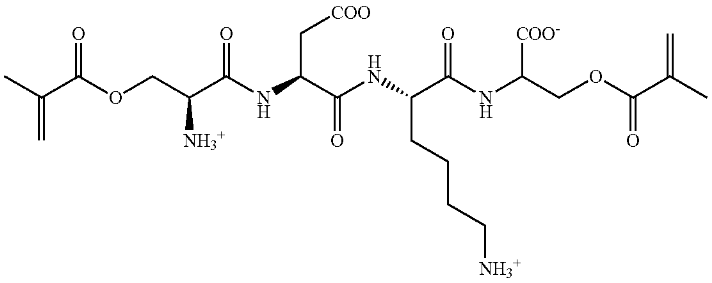<br>(2S,5S,8S,11S)-11-ammonio-5-(4-ammoniobutyl)-8-(carboxylatomethyl)-2-((methacryloyloxy)methyl)-15-methyl-4,7,10,14-tetraoxo-13-oxa-3,6,9-triazahexadec-15-enoate | Ser-Asp-Lys-Ser-dimethacrylate (SDKS) |

TABLE 1-continued

| Structure/ChemDraw Name | Common Name and/or Comments |
| --- | --- |
| 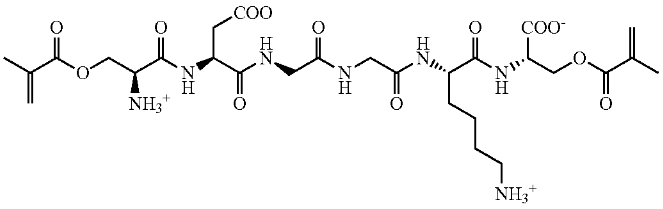<br>(2S,5S,14S)-14-((S)-2-ammonio-3-(methacryloyloxy)propanamido)-5-(4-ammoniobutyl)-2-((methacryloyloxy)methyl)-4,7,10,13-tetraoxo-3,6,9,12-tetraazahexadecanedioate | Ser-Asp-Gly-Gly-Lys-Ser-dimethacrylate (SDGGKS) |
| 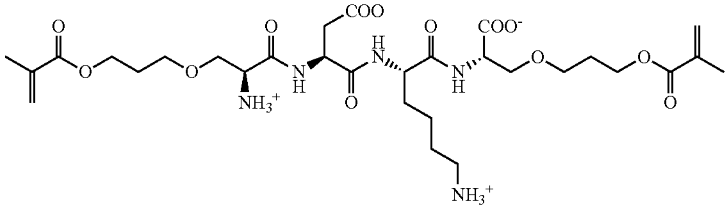<br>(2S,5S,8S,11S)-11-ammonio-5-(4-ammoniobutyl)-8-(carboxylatomethyl)-2-((3-(methacryloyloxy)propoxy)methyl)-19-methyl-4,7,10,18-tetraoxo-13,17-dioxa-3,6,9-triazaicos-19-enoate | ProGly-Ser-Asp-Lys-Ser-ProGly-dimethacrylate |
| 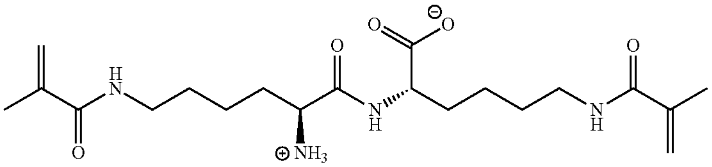 [SMILES: C=C(C)C(=O)NCCCC[C@H](NC(=O)[C@@H]([NH3+])CCCCNC(=O)C(=C)C)C(=O)[O-]]<br>$N^2$-((S)-2-ammonio-6-methacrylamidohexanoyl)-$N^6$-methacryloyl-L-lysinate | N-Lys-Lys-$C_5$ |
| 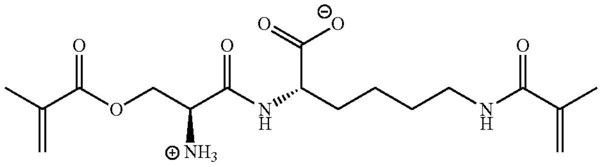 [SMILES: C=C(C)C(=O)NCCCC[C@H](NC(=O)[C@@H]([NH3+])COC(=O)C(=C)C)C(=O)[O-]]<br>$N^2$-((S)-2-ammonio-3-(methacryloyloxy)propanoyl)-$N^6$-methacryloyl-L-lysinate | N-Ser-Ser-Lys-$C_6$ |
| 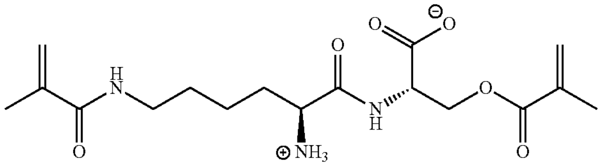 [SMILES: C=C(C)C(=O)NCCCC[C@H]([NH3+])C(=O)N[C@@H](COC(=O)C(=C)C)C(=O)[O-]]<br>N-((S)-2-ammonio-6-methacrylamidohexanoyl)-O-methacryloyl-L-serinate | N-Lys-Ser-$C_7$ |
| 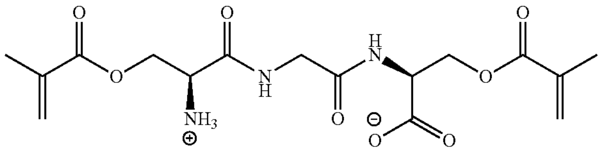 [SMILES: C=C(C)C(=O)OC[C@H](NC(=O)CNC(=O)[C@@H]([NH3+])COC(=O)C(=C)C)C(=O)[O-]]<br>N-(((S)-2-ammonio-3-(methacryloyloxy)propanoyl)glycyl)-O-methacryloyl-L-serinate | N-Ser-Gly-Ser-$C_8$ |

TABLE 1-continued

| Structure/ChemDraw Name | Common Name and/or Comments |
| --- | --- |
| 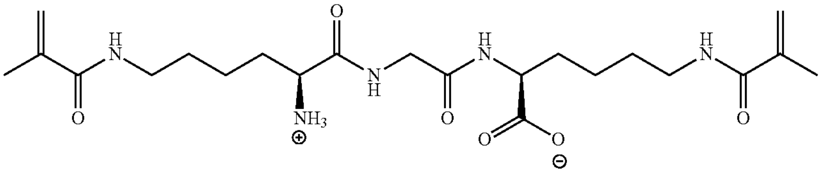 [SMILES: C=C(C)C(=O)NCCCC[C@H](NC(=O)CNC(=O)[C@@H]([NH3+])CCCCNC(=O)C(=C)C)C(=O)[O-]]<br>$N^2$-((S))-2-ammonio-6-methacrylamidohexanoyl)glycyl)-$N^6$-methacryloyl-L-lysinate | N-Lys-G1y-Lys-$C_9$ |
| 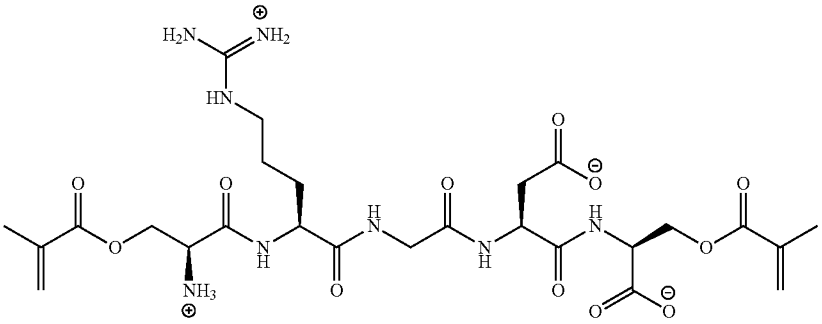 [SMILES: C=C(C)C(=O)OC[C@H](NC(=O)[C@H](CC(=O)[O-])NC(=O)CNC(=O)[C@H](CCCNC(N)=[NH2+])NC(=O)[C@@H]([NH3+])COC(=O)C(=C)C)C(=O)[O-]]<br>(2S,5S,11S,14S)-14-amino-5-(carboxymethyl)-11-(3-guanidinopropyl)-2-((methacryloyloxy)methyl)-18-methyl-4,7,10,13,17-pentaoxo-16-oxa-3,6,9,12-tetraazanonadec-18-enoic acid | Ser-Asp-Gly-Asp-Ser-dimethacrylate |
| 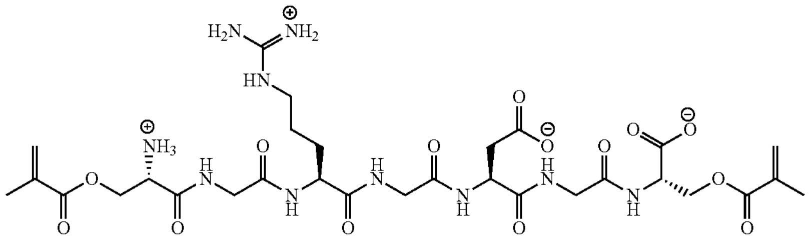 [SMILES: C=C(C)C(=O)OC[C@H](NC(=O)CNC(=O)[C@H](CC(=O)[O-])NC(=O)CNC(=O)[C@H](CCCNC(N)=[NH2+])NC(=O)CNC(=O)[C@@H]([NH3+])COC(=O)C(=C)C)C(=O)[O-]]<br>(2S,8S,14S,20S)-20-amino-8-(carboxymethyl)-14-(3-guanidinopropyl)-2-((methacryloyloxy)methyl)-24-methyl-4,7,10,13,16,19,23-heptaoxo-22-oxa-3,6,9,12,15,18-hexaazapentacos-24-enoic acid | Ser-Gly-Arg-Gly-Asp-Gly-Ser-dimethacrylate |
| 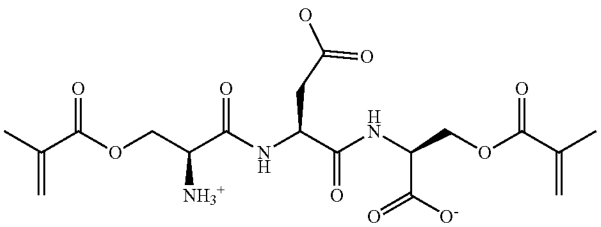 [SMILES: C=C(C)C(=O)OC[C@H](NC(=O)[C@H](CC(=O)O)NC(=O)[C@@H]([NH3+])COC(=O)C(=C)C)C(=O)[O-]]<br>(S)-3-((S)-2-amino-3-(methacryloyloxy)propanamido)-4-(((S)-1-carboxy-2-(methacryloyloxy)ethyl)amino)-4-oxobutanoic acid | Ser-Asp-Ser |
| 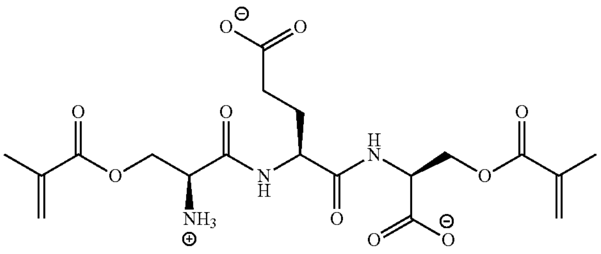 [SMILES: C=C(C)C(=O)OC[C@H](NC(=O)[C@H](CCC(=O)[O-])NC(=O)[C@@H]([NH3+])COC(=O)C(=C)C)C(=O)[O-]] | Ser-Glu-Ser<br>Example of a Crosslinker according to present invention comprising a functionalizable pendant side chain |

TABLE 1-continued

| Structure/ChemDraw Name | Common Name and/or Comments |
| --- | --- |
| (S)-4-((S)-2-amino-3-(methacryloyloxy)propanamido)-5-(((S)-1-carboxy-2-(methacryloyloxy)ethyl)amino)-5-oxopentanoic acid | |
| 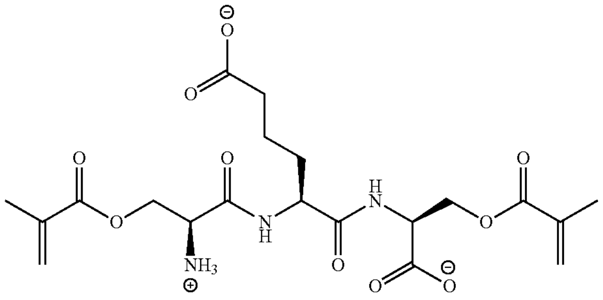 [SMILES: C=C(C)C(=O)OC[C@H](NC(=O)[C@H](CCCC(=O)[O-])NC(=O)[C@@H]([NH3+])COC(=O)C(=C)C)C(=O)[O-]] | Example of a Crosslinker according to present invention comprising a functionalizable pendant side chain |
| (S)-5-((S)-2-amino-3-(methacryloyloxy)propanamido)-6-(((S)-1-carboxy-2-(methacryloyloxy)ethyl)amino)-6-oxohexanoic acid | |
| 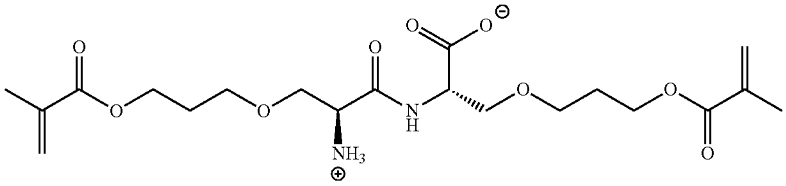 [SMILES: C=C(C)C(=O)OCCCOC[C@H](NC(=O)[C@@H]([NH3+])COCCCOC(=O)C(=C)C)C(=O)[O-]] | Ser-Ser-bis(propylmethacrylate) |
| N-((S)-2-ammonio-3-(3-(methacryloyloxy)propoxy)propanoyl)-O-(3-(methacryloyloxy)propyl)-L-serinate | |
| 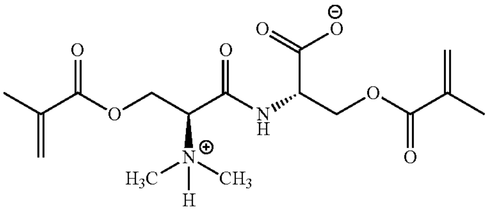 [SMILES: C=C(C)C(=O)OC[C@H](NC(=O)[C@H](COC(=O)C(=C)C)[NH+](C)C)C(=O)[O-]] | |
| N-((S)-2-(dimethylammonio)-3-(methacryloyloxy)propanoyl)-O-methacryloyl-L-serinate | |
| 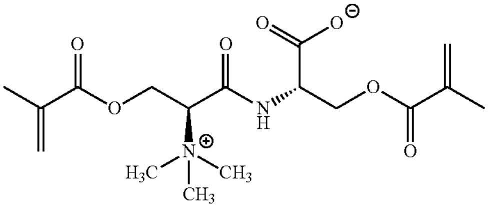 [SMILES: C=C(C)C(=O)OC[C@H](NC(=O)[C@H](COC(=O)C(=C)C)[N+](C)(C)C)C(=O)[O-]] | |
| O-methacryloyl-N-((S)-3-(methacryloyloxy)-2-(trimethylammonio)propanoyl)-L-serinate | |
| 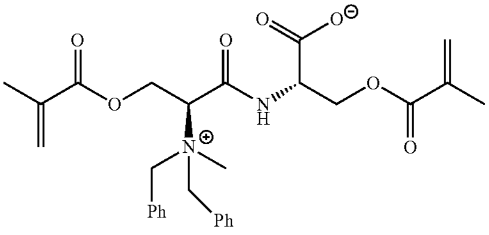 [SMILES: C=C(C)C(=O)OC[C@H](NC(=O)[C@H](COC(=O)C(=C)C)[N+](C)(Cc1ccccc1)Cc1ccccc1)C(=O)[O-]] | |
| N-((S)-2-(dibenzyl(methyl)ammonio)-3-(methacryloyloxy)propanoyl)-O-methacryloyl-L-serinate | |

TABLE 1-continued

| Structure/ChemDraw Name | Common Name and/or Comments |
|---|---|
| 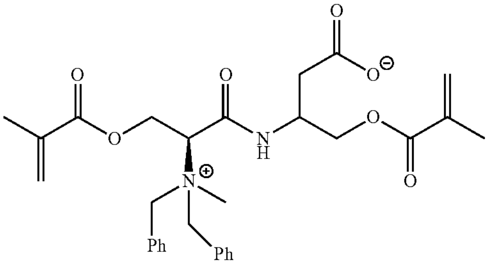 [SMILES: C=C(C)C(=O)OCC(CC(=O)[O-])NC(=O)[C@H](COC(=O)C(=C)C)[N+](C)(Cc1ccccc1)Cc1ccccc1] 3-((S)-2-(dibenzyl(methypammonio)-3-(methacryloyloxy)propanamido)-4-(methacryloyloxy)butanoate | |
| 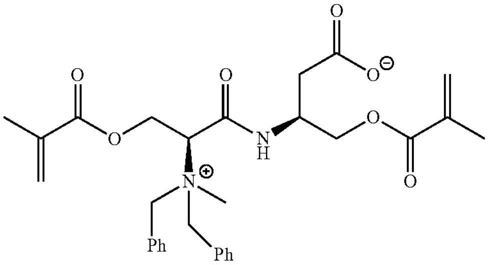 [SMILES: C=C(C)C(=O)OC[C@H](CC(=O)[O-])NC(=O)[C@H](COC(=O)C(=C)C)[N+](C)(Cc1ccccc1)Cc1ccccc1] 3-((S)-2-(dibenzylammonio)-3-(methacryloyloxy)propanamido)-4-(methacryloyloxy)butanoate (S)-3-((S)-2-(dibenzyl(methypammonio)-3-(methacryloyloxy)propanamido)-4-(methacryloyloxy)butanoate | |
| 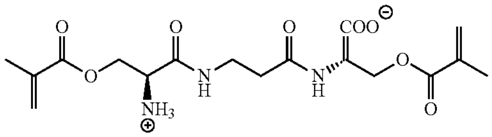 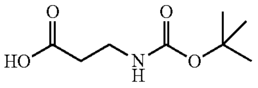 Ser-β-Ala-Ser N-(3-((S)-2-ammonio-3-(methacryloyloxy)propanamido)propanoyl)-O-methacryloyl-L-serinate | Ser-β-Ala-Ser Illustrating use of an internal spacer, with the protected spacer shown on the right. |
| 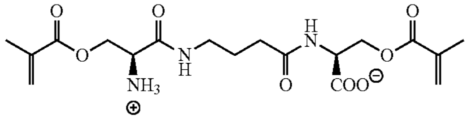 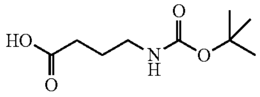 N-(4-((S)-2-ammonio-3-(methacryloyloxy)propanamido)butanoyl)-O-methacryloyl-L-serinate | Illustrating use of an internal spacer, with the particular spacer shown on the right. |
| 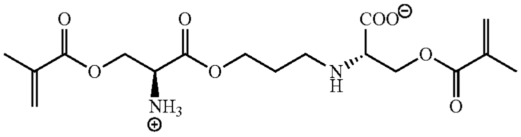 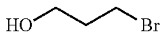 N-(3-(((S)-2-ammonio-3-(methacryloyloxy)propanoyl)oxy)propyl)-O-methacryloyl-L-serinate | Illustrating use of an internal spacer, with the protected spacer shown on the the right. |
| 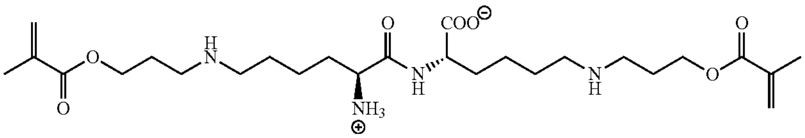 | Illustrating use of an external spacer. |

TABLE 1-continued

| Structure/ChemDraw Name | Common Name and/or Comments |
| --- | --- |
| $N^2$-((S)-2-ammonio-6-((3-(methacryloyloxy)propyl)amino)hexanoyl)-$N^6$-(3-(methacryloyloxy)propyl)-L-lysinate | |
| 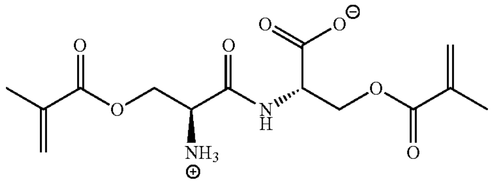 [SMILES: C=C(C)C(=O)OC[C@H](NC(=O)[C@@H]([NH3+])COC(=O)C(=C)C)C(=O)[O-]] | |
| N-((S)-2-ammonio-3-(methacryloyloxy)propanoyl)-O-methacryloyl-L-serinate | |
| 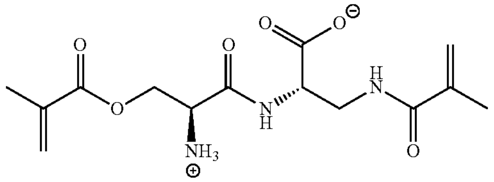 | |
| (S)-2-((S)-2-ammonio-3-(methacryloyloxy)propanamido)-3-methacrylamidopropanoate | |
| 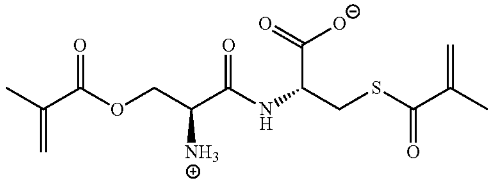 [SMILES: C=C(C)C(=O)OC[C@H]([NH3+])C(=O)N[C@@H](CSC(=O)C(=C)C)C(=O)[O-]] | |
| N-((S)-2-ammonio-3-(methacryloyloxy)propanoyl)-S-methacryloyl-L-cysteinate | |
| 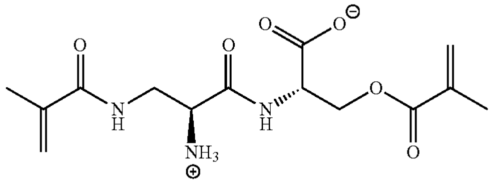 | |
| N-((S)-2-ammonio-3-methacrylamidopropanoyl)-O-methacryloyl-L-serinate | |
| 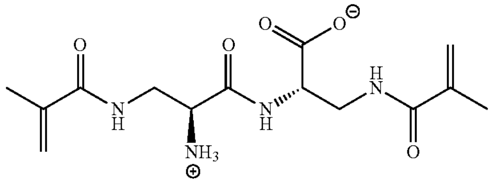 [SMILES: C=C(C)C(=O)NC[C@H](NC(=O)[C@@H]([NH3+])CNC(=O)C(=C)C)C(=O)[O-]] | |
| (S)-2-((S)-2-ammonio-3-methacrylamidopropanamido)-3-methacrylamidopropanoate | |
| 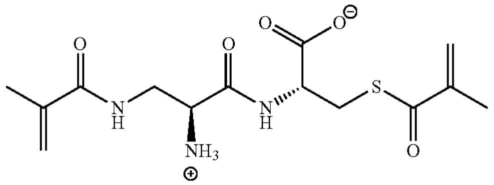 [SMILES: C=C(C)C(=O)NC[C@H]([NH3+])C(=O)N[C@@H](CSC(=O)C(=C)C)C(=O)[O-]] | |

TABLE 1-continued

| Structure/ChemDraw Name | Common Name and/or Comments |
|---|---|
| N-((S)-2-ammonio-3-methacrylamidopropanoyl)-S-methacryloyl-L-cysteinate | |
| 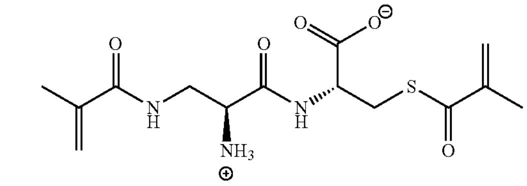 [SMILES: C=C(C)C(=O)NC[C@H]([NH3+])C(=O)N[C@@H](CSC(=O)C(=C)C)C(=O)[O-]] | |
| N-((S)-2-ammonio-3-methacrylamidopropanoyl)-S-methacryloyl-L-cysteinate | |
| 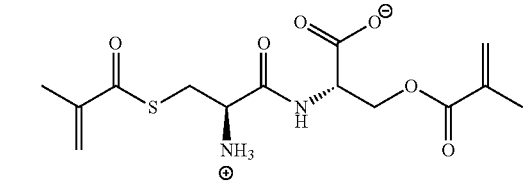 [SMILES: C=C(C)C(=O)OC[C@H](NC(=O)[C@@H]([NH3+])CSC(=O)C(=C)C)C(=O)[O-]] | |
| N-((R)-2-ammonio-3-(methacryloyithio)propanoyl)-O-methacryloyl-L-serinate | |
| 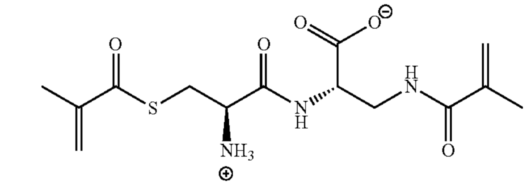 | |
| (S)-2-((R)-2-ammonio-3-(methacryloyithio)propanamido)-3-methacrylamidopropanoate | |
| 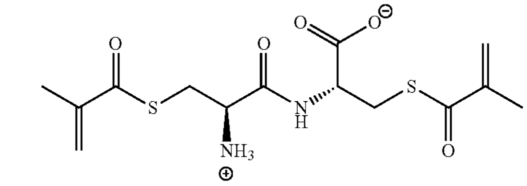 [SMILES: C=C(C)C(=O)SC[C@H](NC(=O)[C@@H]([NH3+])CSC(=O)C(=C)C)C(=O)[O-]] | |
| N-((R)-2-ammonio-3-(methacryloyithio)propanoyl)-S-methacryloyl-L-cysteinate | |
| 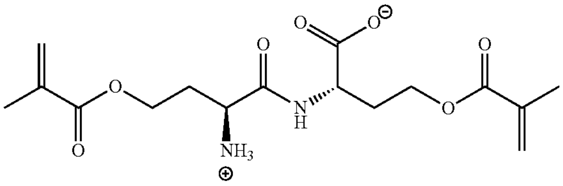 | |
| N-((S)-2-ammonio-4-(methacryloyloxy)butanoyl)-O-methacryloyl-L-homoserinate | |
| 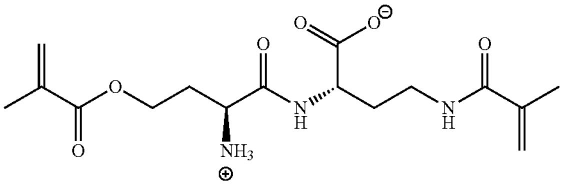 | |

TABLE 1-continued

| Structure/ChemDraw Name | Common Name and/or Comments |
|---|---|
| (S)-2-((S)-2-ammonio-4-(methacryloyloxy)butanamido)-4-methacrylamidobutanoate | |
| 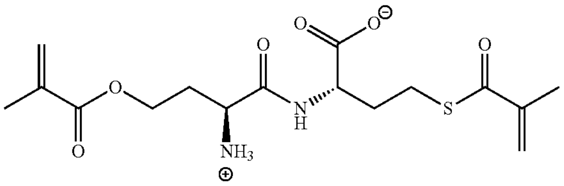 | |
| N-((S)-2-ammonio-4-(methacryloyloxy)butanoyl)-S-methacryloyl-L-homocysteinate | |
| 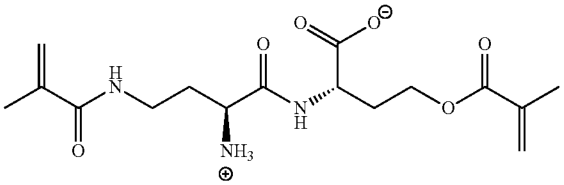 | |
| N-((S)-2-ammonio-4-methacrylamidobutanoyl)-O-methacryloyl-L-homoserinate | |
| 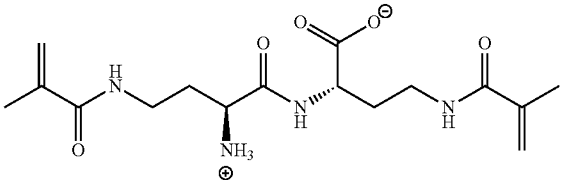 | |
| (S)-2-((S)-2-ammonio-4-methacrylamidobutanamido)-4-methacrylamidobutanoate | |
| 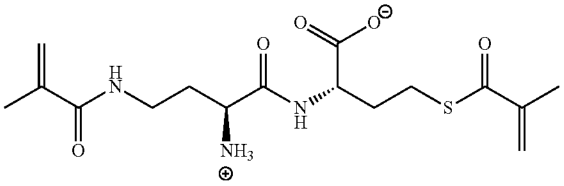 [SMILES: C=C(C)C(=O)NCC[C@H]([NH3+])C(=O)N[C@@H](CCOC(=O)C(=C)C)C(=O)[O-]] | |
| N-((S)-2-ammonio-4-methacrylamidobutanoyl)-S-methacryloyl-L-homocysteinate | |
| 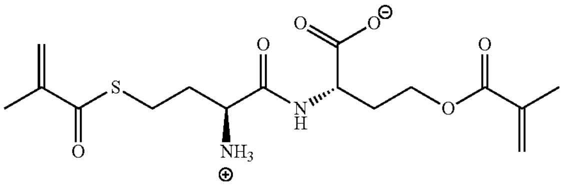 [SMILES: C=C(C)C(=O)OCC[C@H](NC(=O)[C@@H]([NH3+])CCSC(=O)C(=C)C)C(=O)[O-]] | |
| N-((S)-2-ammonio-4-(methacryloyithio)butanoyl)-O-methacryloyl-L-homoserinate | |
| 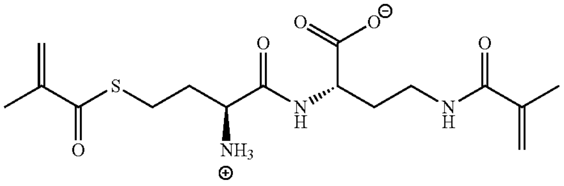 [SMILES: C=C(C)C(=O)NCC[C@H](NC(=O)[C@@H]([NH3+])CCSC(=O)C(=C)C)C(=O)[O-]] | |

TABLE 1-continued

| Structure/ChemDraw Name | Common Name and/or Comments |
| --- | --- |
| (S)-2-((S)-2-ammonio-4-(methacryloylthio)butanamido)-4-methacrylamidobutanoate | |
| 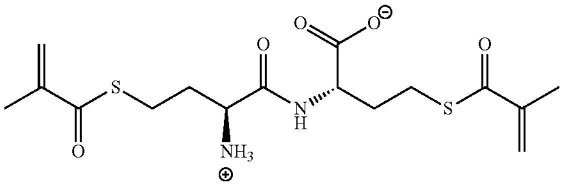 | |
| N-((S)-2-ammonio-4-(methacryloylthio)butanoyl)-S-methacryloyl-L-homocysteinate | |
| 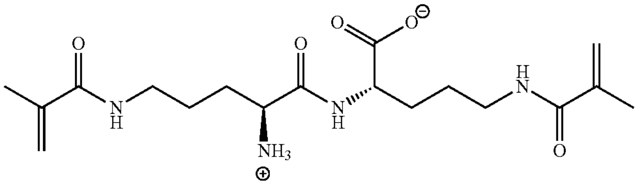 [SMILES: C=C(C)C(=O)NCCC[C@H](NC(=O)[C@@H]([NH3+])CCCNC(=O)C(=C)C)C(=O)[O-]] | |
| (S)-2-((S)-2-ammonio-5-methacrylamidopentanamido)-5-methacrylamidopentanoate | |
| 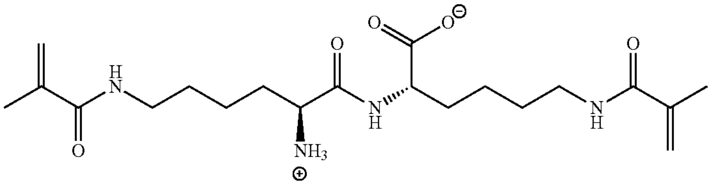 [SMILES: C=C(C)C(=O)NCCCC[C@H](NC(=O)[C@@H]([NH3+])CCCCNC(=O)C(=C)C)C(=O)[O-]] | |
| $N^2$-((S)-2-ammonio-6-methacrylamidohexanoyl)-$N^6$-methacryloyl-L-lysinate | |
| 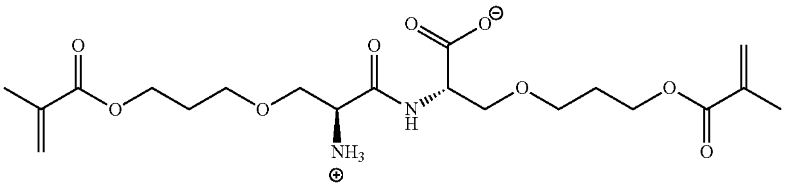 [SMILES: C=C(C)C(=O)OCCCOC[C@H](NC(=O)[C@@H]([NH3+])COCCCOC(=O)C(=C)C)C(=O)[O-]] | |
| 34 propylene glycol serine dipeptide 16 atom spacer N-((S)-2-ammonio-3-(3-(methacryloyloxy)propoxy)propanoyl)-O-(3-(methacryloyloxy)propyl)-L-serinate | |
| 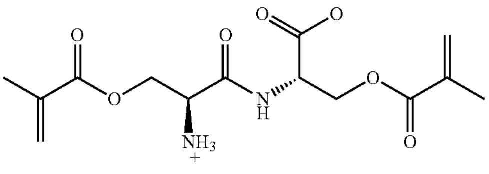 [SMILES: C=C(C)C(=O)OC[C@H](NC(=O)[C@@H](N)COC(=O)C(=C)C)C(=O)O] | Ser-Ser-dimethacrylate or SS-dimethacrylate |
| N-((S)-2-($\lambda^4$-azaneyl)-3-(methacryloyloxy)propanoyl)-O-methacryloyl-L-serinate | |
| 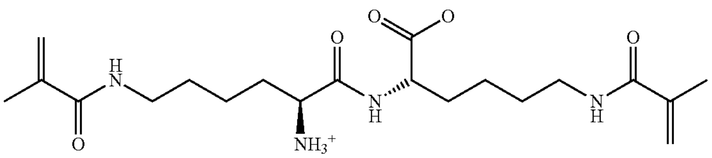 | Lys-Lys-dimethacrylate or LL-dimethacrylate |

TABLE 1-continued

| Structure/ChemDraw Name | Common Name and/or Comments |
|---|---|
| N$^2$-((S)-2-ammonio-6-methacrylamidohexanoyl)-N$^6$-methacryloyl-L-lysinate | |
| 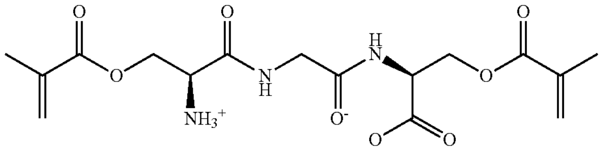 N-(((S)-2-ammonio-3-(methacryloyloxy)propanoyl)glycyl)-O-methacryloyl-L-serinate | Ser-Gly-Ser-dimethacrylate (SGS) |
| 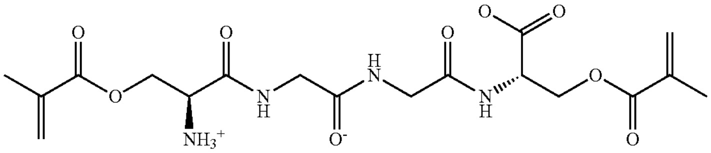 N-((S)-2-ammonio-3-(methacryloyloxy)propanoyl)glycylglycyl-O-methacryloyl-L-serinate | Ser-Gly-Gly-Ser-dimethacrylate (SGGS) |
| 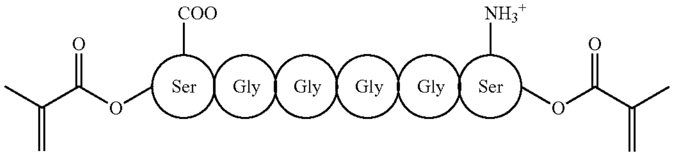 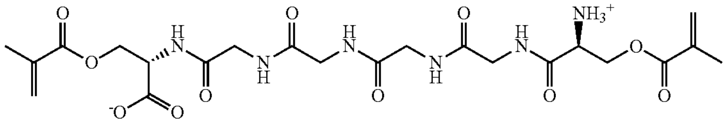 N-((S)-2-ammonio-3-(methacryloyloxy)propanoyl)glycylglycylglycylglycyl-O-methacryloyl-L-serinate | Ser-Gly-Gly-Gl-Gly-Ser-dimethacrylate (SGGGS) |
| 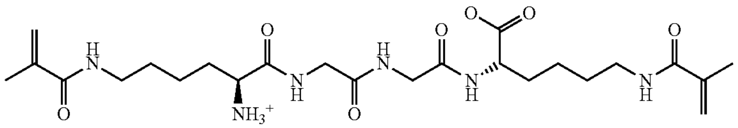 N$^2$-((S)-2-ammonio-6-methacrylamidohexanoyl)glycylglycyl-N$^6$-methacryloyl-L-lysinate | Lys-Gly-Gly-Lys dimethacrylate (LGGL) |
| 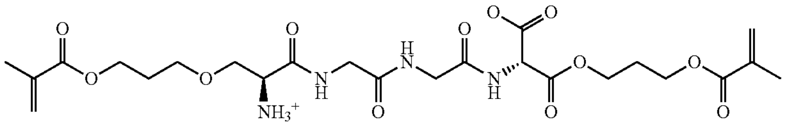 [SMILES: C=C(C)C(=O)OCCCOC[C@H]([NH3+])C(=O)NCC(=O)NCC(=O)N[C@H](C(=O)O)C(=O)OCCCOC(=O)C(=C)C] N-((S)-2-ammonio-3-(3-(methacryloyloxy)propoxy)propanoyl)glycylglycyl-O-(3-(methacryloyloxy)propyl)-L-serinate | Ser-Gly-Gly-Ser-propylene glycol dimethacrylate (SGGS-ProGly) |

TABLE 1-continued

| Structure/ChemDraw Name | Common Name and/or Comments |
|---|---|
| 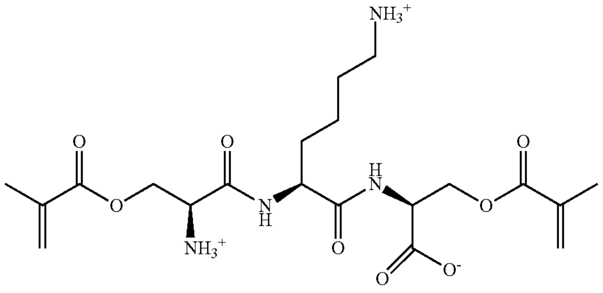<br>N-((S)-6-ammonio-2-((S)-2-ammonio-3-(methacryloyloxy)propanamido)hexanoyl)-O-methacryloyl-L-serinate | Ser-Lys-Ser-dimethacrylate (SLS) |
| 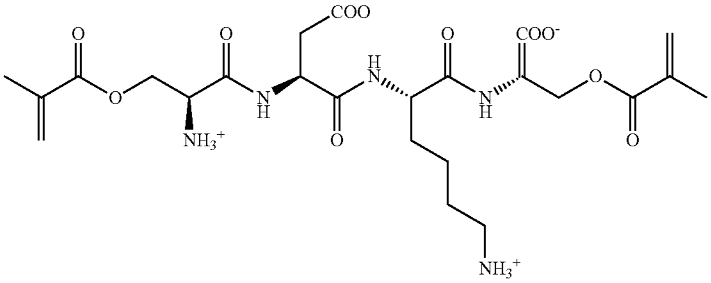<br>(2S,5S,8S,11S)-11-ammonio-5-(4-ammoniobutyl)-8-(carboxylatomethyl)-2-((methacryloyloxy)methyl)-15-methyl-4,7,10,14-tetraoxo-13-oxa-3,6,9-triazahexadec-15-enoate | Ser-Asp-Lys-Ser-dimethacrylate (SALS) |
| 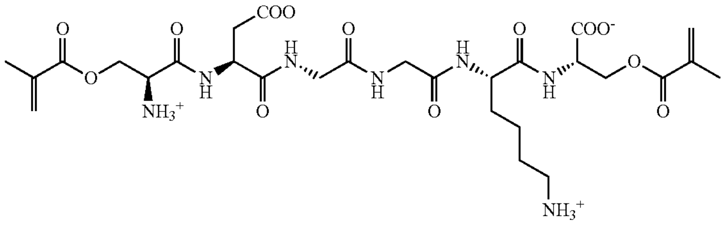<br>(2S,5S,14S)-14-((S)-2-ammonio-3-(methacryloyloxy)propanamido)-5-(4-ammoniobutyl)-2-((methacryloyloxy)methyl)-4,7,10,13-tetraoxo-3,6,9,12-tetraazahexadecanedioate | Ser-Asp-Gly-Gly-Lys-Ser-dimethacrylate (SAGGLS) |
| 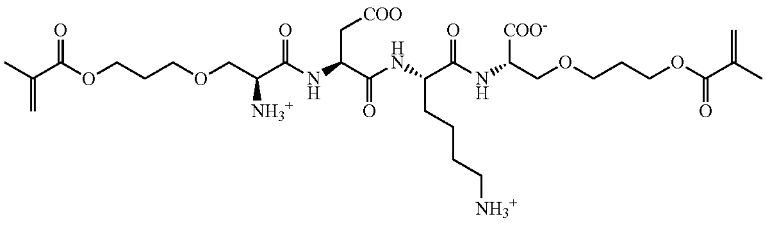<br>(2S,5S,8S,11S)-11-ammonio-5-(4-ammoniobutyl)-8-(carboxylatomethyl)-2-43-(methacryloyloxy)propoxy)methyl)-19-methyl-4,7,10,18-tetraoxo-13,17-dioxa-3,6,9-triazaicos-19-enoate | ProGly-sear-Asp-Lys-ser-ProGly-dimethacrylate |
| 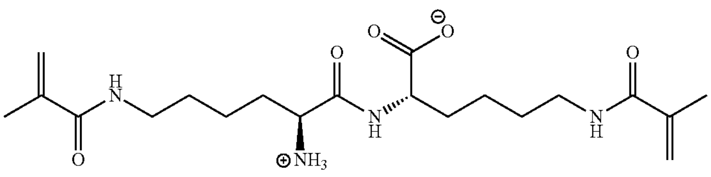 [SMILES: C=C(C)C(=O)NCCCC[C@H](NC(=O)[C@@H]([NH3+])CCCCNC(=O)C(=C)C)C(=O)[O-]] | N-Lys-Lys-$C_5$ |

TABLE 1-continued

| Structure/ChemDraw Name | Common Name and/or Comments |
|---|---|
| $N^2$-((S)-2-ammonio-6-methacrylamidohexanoyl)-$N^6$-methacryloyl-L-lysinate | |
| 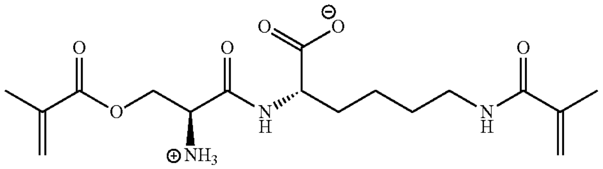 [SMILES: C=C(C)C(=O)NCCCC[C@H](NC(=O)[C@@H]([NH3+])COC(=O)C(=C)C)C(=O)[O-]]<br>$N^2$-((S)-2-ammonio-3-(methacryloyloxy)propanoyl)-$N^6$-methacryloyl-L-lysinate | N-Ser-Ser-Lys-$C_6$ |
| 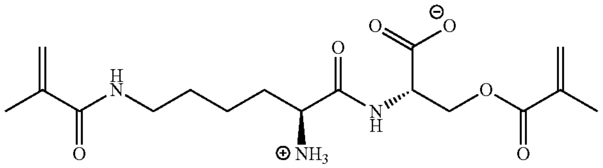 [SMILES: C=C(C)C(=O)NCCCC[C@H]([NH3+])C(=O)N[C@@H](COC(=O)C(=C)C)C(=O)[O-]]<br>N-((S)-2-ammonio-6-methacrylamidohexanoyl)-O-methacryloyl-L-serinate | N-Lys-Ser-$C_7$ |
| 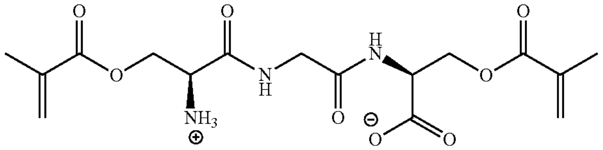 [SMILES: C=C(C)C(=O)OC[C@H](NC(=O)CNC(=O)[C@@H]([NH3+])COC(=O)C(=C)C)C(=O)[O-]]<br>N-(((S)-2-ammonio-3-(methacryloyloxy)propanoyl)glycyl)-O-methacryloyl-L-serinate | N-Ser-G1y-Ser-$C_8$ |
| 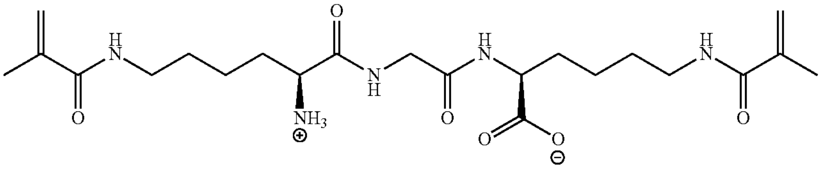 [SMILES: C=C(C)C(=O)NCCCC[C@H](NC(=O)CNC(=O)[C@@H]([NH3+])CCCCNC(=O)C(=C)C)C(=O)[O-]]<br>$N^2$-(((S)-2-ammonio-6-methacrylamidohexanoyl)glycyl)-$N^6$-methacryloyl-L-lysinate | N-Lys-G1y-Lys-$C_9$ |
| 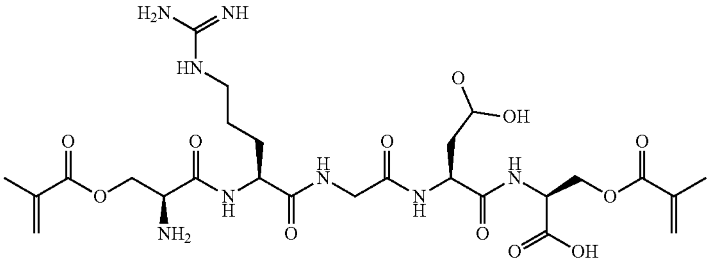 [SMILES: C=C(C)C(=O)OC[C@H](NC(=O)[C@H](CC(O)O)NC(=O)CNC(=O)[C@H](CCCNC(=N)N)NC(=O)[C@@H](N)COC(=O)C(=C)C)C(=O)O]<br>(2S,5S,11S,14S)-14-amino-5-(carboxymethyl)-11-(3-guanidinopropyl)-2-((methacryloyloxy)methyl)-18-methyl-4,7,10,13,17-pentaoxo-16-oxa-3,6,9,12-tetraazanonadec-18-enoic acid | Ser-Arg-Gly-Asp-Ser-dimethacrylate |

TABLE 1-continued

| Structure/ChemDraw Name | Common Name and/or Comments |
|---|---|
| 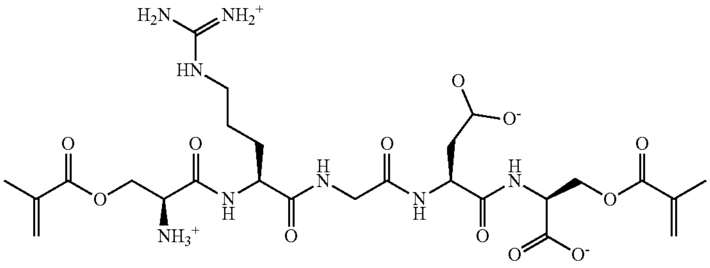 [SMILES: C=C(C)C(=O)OC[C@H](NC(=O)[C@H](CC([O-])O)NC(=O)CNC(=O)[C@H](CCCNC(N)=[NH2+])NC(=O)[C@@H]([NH3+])COC(=O)C(=C)C)C(=O)[O-]]<br>(2S,5S,11S,14S)-11-(3-((amino(iminio)methypamino)propyl)-14-ammonio-5-(carboxylatomethyl)-2-((methacryloyloxy)methyl)-18-methyl-4,7,10,13,17-pentaoxo-16-oxa-3,6,9,12-tetraazanonadec-18-enoate | |
| 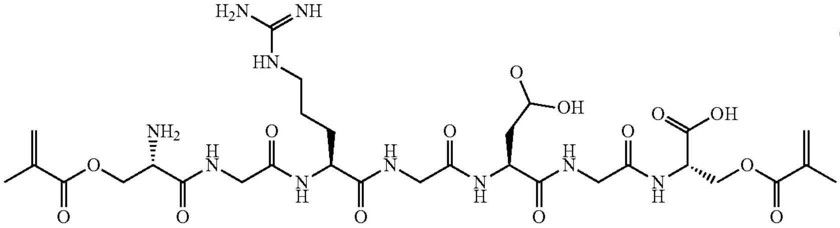 [SMILES: C=C(C)C(=O)OC[C@H](NC(=O)CNC(=O)[C@H](CC(O)O)NC(=O)CNC(=O)[C@H](CCCNC(=N)N)NC(=O)CNC(=O)[C@@H](N)COC(=O)C(=C)C)C(=O)O]<br>(2S,8S,14S,20S)-20-amino-8-(carboxymethyl)-14-(3-guanidinopropyl)-2-((methacryloyloxy)methyl)-24-methyl-4,7,10,13,16,19,23-heptaoxo-22-oxa-3,6,9,12,15,18-hexaazapentacos-24-enoic acid | Ser-Gly-Arg-Gly-Asp-Gly-Ser-dimethacrylate |
| 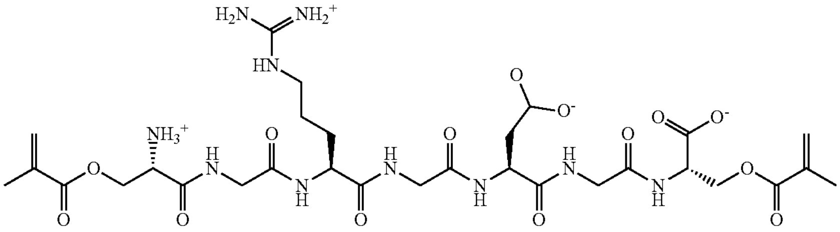 [SMILES: C=C(C)C(=O)OC[C@H](NC(=O)CNC(=O)[C@H](CC([O-])O)NC(=O)CNC(=O)[C@H](CCCNC(N)=[NH2+])NC(=O)CNC(=O)[C@@H]([NH3+])COC(=O)C(=C)C)C(=O)[O-]]<br>(2S,8S,14S,20S)-14-(3-((amino(iminio)methypamino)propyl)-20-ammonio-8-(carboxylatomethyl)-2-((methacryloyloxy)methyl)-24-methyl-4,7,10,13,16,19,23-heptaoxo-22-oxa-3,6,9,12,15,18-hexaazapentacos-24-enoate | |
| 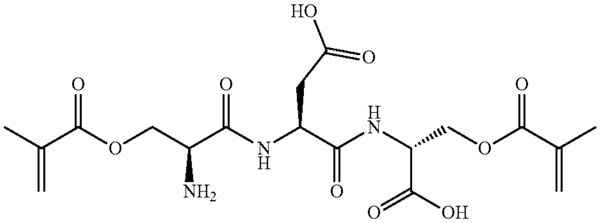 [SMILES: C=C(C)C(=O)OC[C@H](N)C(=O)N[C@@H](CC(=O)O)C(=O)N[C@H](COC(=O)C(=C)C)C(=O)O]<br>(S)-3-((S)-2-amino-3-(methacryloyloxy)propanamido)-4-(((R)-1-carboxy-2-(methacryloyloxy)ethyl)amino)-4-oxobutanoic acid | Ser-Asp-Ser |
| 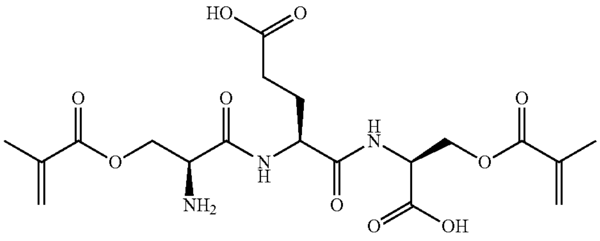 [SMILES: C=C(C)C(=O)OC[C@H](NC(=O)[C@H](CCC(=O)O)NC(=O)[C@@H](N)COC(=O)C(=C)C)C(=O)O] | Ser-Glu-Ser |

TABLE 1-continued

| Structure/ChemDraw Name | Common Name and/or Comments |
|---|---|
| (S)-4-((S)-2-amino-3-(methacryloyloxy)propanamido)-5-(((S)-1-carboxy-2-(methacryloyloxy)ethyl)amino)-5-oxopentanoic acid | |
| 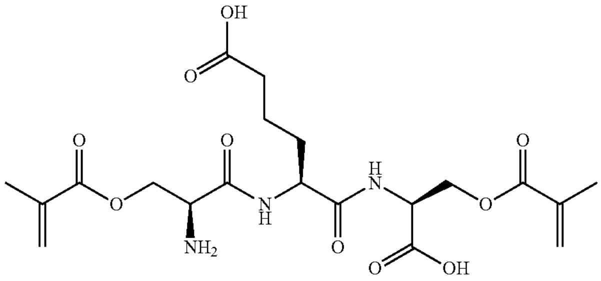 [SMILES: C=C(C)C(=O)OC[C@H](NC(=O)[C@H](CCCC(=O)O)NC(=O)[C@@H](N)COC(=O)C(=C)C)C(=O)O] | |
| (S)-5-((S)-2-amino-3-(methacryloyloxy)propanamido)-6-(((S)-1-carboxy-2-(methacryloyloxy)ethyl)amino)-6-oxohexanoic acid | |
| 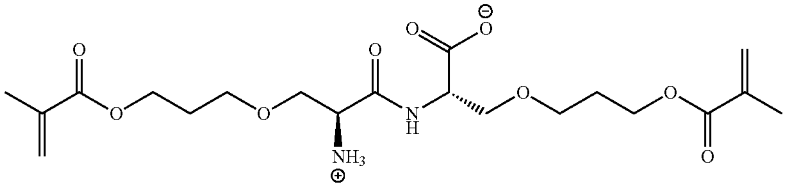 [SMILES: C=C(C)C(=O)OCCCOC[C@H](NC(=O)[C@@H]([NH3+])COCCCOC(=O)C(=C)C)C(=O)[O-]] | Ser-Ser-bis(propylmethacrylate) |
| N-((S)-2-ammonio-3-(3-(methacryloyloxy)propoxy)propanoyl)-O-(3-(methacryloyloxy)propyl)-L-serinate | |
| 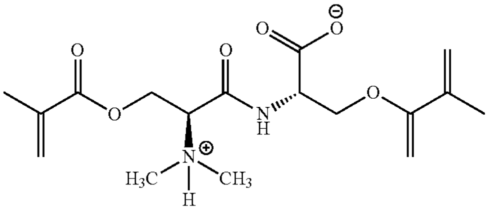 [SMILES: C=C(C)C(=C)OC[C@H](NC(=O)[C@H](COC(=O)C(=C)C)[NH+](C)C)C(=O)[O-]] | |
| N-((S)-2-(dimethylammonio)-3-(methacryloyloxy)propanoyl)-O-methacryloyl-L-serinate | |
| 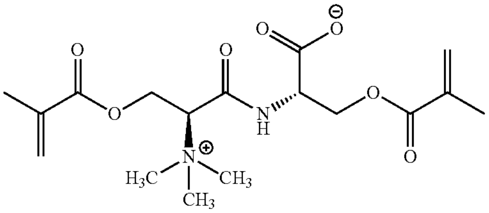 [SMILES: C=C(C)C(=O)OC[C@H](NC(=O)[C@H](COC(=O)C(=C)C)[N+](C)(C)C)C(=O)[O-]] | |
| O-methacryloyl-N-((S)-3-(methacryloyloxy)-2-(trimethylammonio)propanoyl)-L-serinate | |
| 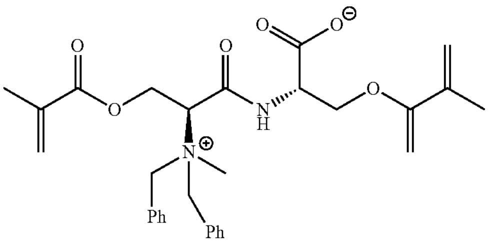 [SMILES: C=C(C)C(=C)OC[C@H](NC(=O)[C@H](COC(=O)C(=C)C)[N+](C)(Cc1ccccc1)Cc1ccccc1)C(=O)[O-]] | |
| N-((S)-2-(dibenzyl(methyl)ammonio)-3-(methacryloyloxy)propanoyl)-O-methacryloyl-L-serinate | |

TABLE 1-continued

| Structure/ChemDraw Name | Common Name and/or Comments |
|---|---|
| 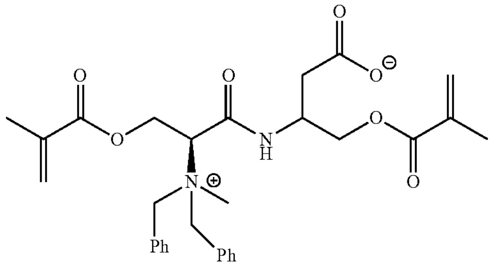 [SMILES: C=C(C)C(=O)OCC(CC(=O)[O-])NC(=O)[C@H](COC(=O)C(=C)C)[N+](C)(Cc1ccccc1)Cc1ccccc1] 3-((S)-2-(dibenzyl(methypammonio)-3-(methacryloyloxy)propanamido)-4-(methacryloyloxy)butanoate | |
| 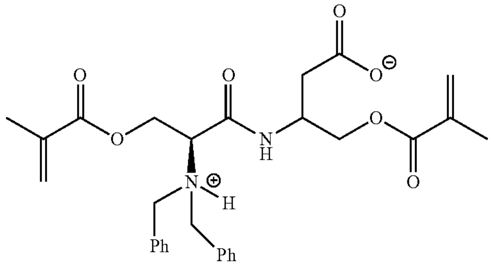 [SMILES: C=C(C)C(=O)OCC(CC(=O)[O-])NC(=O)[C@H](COC(=O)C(=C)C)[NH+](Cc1ccccc1)Cc1ccccc1] 3-((S)-2-(dibenzylammonio)-3-(methacryloyloxy)propanamido)-4-(methacryloyloxy)butanoate | |
| 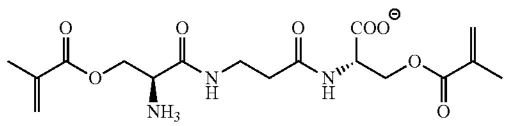 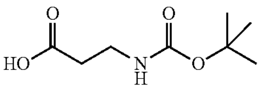 Ser-β-Ala-Ser N-(3-((S)-2-ammonio-3-(methacryloyloxy)propanamido)propanoyl)-O-methacryloyl-L-serinate | Ser-β-Ala-Ser Illustrating use of an internal spacer, with the protected spacer shown on the right. |
| 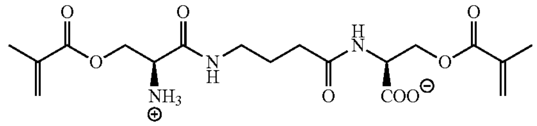 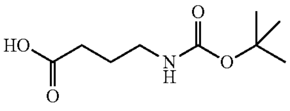 N-(4-((S)-2-ammonio-3-(methacryloyloxy)propanamido)butanoyl)-O-methacryloyl-L-serinate | Illustrating use of an internal spacer, with the particular spacer shown on the right. |
| 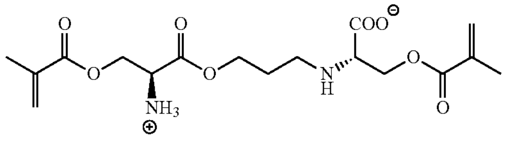 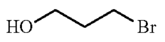 N-(3-((S))-2-ammonio-3-(methacryloyloxy)propanoyl)oxy)propyl)-O-methacryloyl-L-serinate | Illustrating use of an internal spacer, with the protected spacer shown on the right. |
| 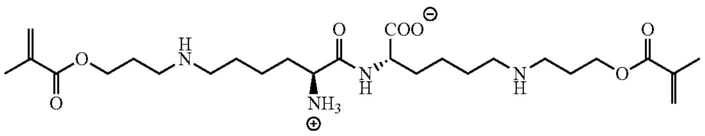 N$^{2}$-((S)-2-ammonio-6-((3-(methacryloyloxy)propyl)amino)hexanoyl)-N$^{6}$-(3-(methacryloyloxy)propyl)-L-lysinate | Illustrating use of an external spacer. |

TABLE 1-continued

| Structure/ChemDraw Name | Common Name and/or Comments |
| --- | --- |
| 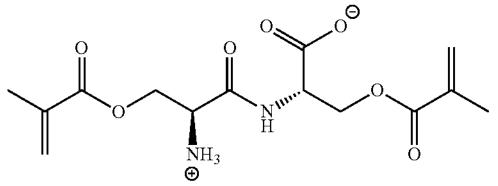 [SMILES: C=C(C)C(=O)OC[C@H](NC(=O)[C@@H]([NH3+])CSC(=O)C(=C)C)C(=O)[O-]] N-((S)-2-ammonio-3-(methacryloyloxy)propanoyl)-O-methacryloyl-L-serinate | |
| 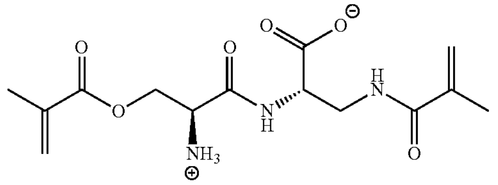 [SMILES: C=C(C)C(=O)NC[C@H](NC(=O)[C@@H]([NH3+])CSC(=O)C(=C)C)C(=O)[O-]] (S)-2-((S)-2-ammonio-3-(methacryloyloxy)propanamido)-3-methacrylamidopropanoate | |
| 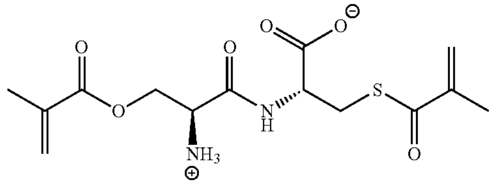 N-((S)-2-ammonio-3-(methacryloyloxy)propanoyl)-S-methacryloyl-L-cysteinate | |
| 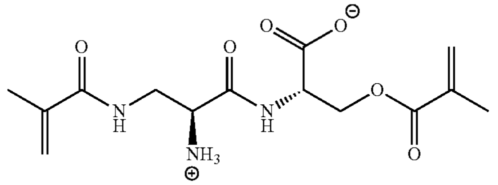 N-((S)-2-ammonio-3-methacrylamidopropanoyl)-O-methacryloyl-L-serinate | |
| 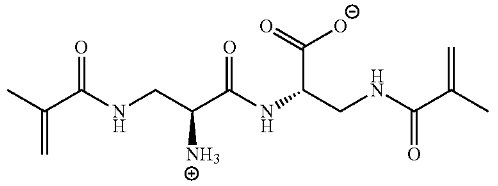 (S)-2-((S)-2-ammonio-3-methacrylamidopropanamido)-3-methacrylamidopropanoate | |
| 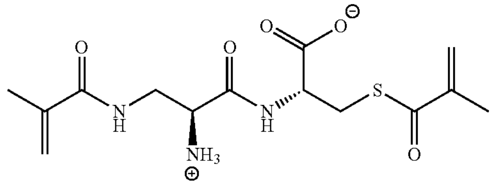 N-((S)-2-ammonio-3-methacrylamidopropanoyl)-S-methacryloyl-L-cysteinate | |

TABLE 1-continued

| Structure/ChemDraw Name | Common Name and/or Comments |
| --- | --- |
| 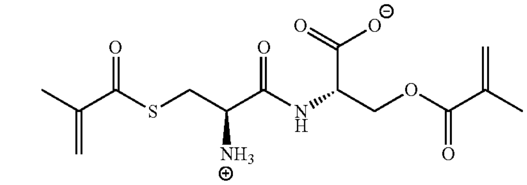 [SMILES: C=C(C)C(=O)SC[C@H](NC(=O)[C@@H]([NH3+])CSC(=O)C(=C)C)C(=O)[O-]]<br>N-((R)-2-ammonio-3-(methacryloylthio)propanoyl)-O-methacryloyl-L-serinate | |
| 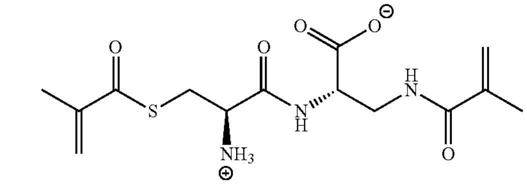<br>(S)-2-((R)-2-ammonio-3-(methacryloyithio)propanamido)-3-methacrylamidopropanoate | |
| 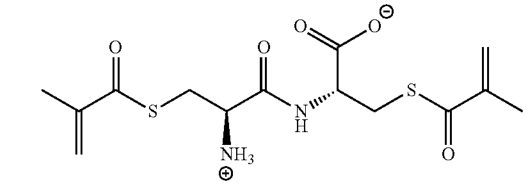<br>N-((R)-2-ammonio-3-(methacryloylthio)propanoyl)-S-methacryloyl-L-cysteinate | |
| 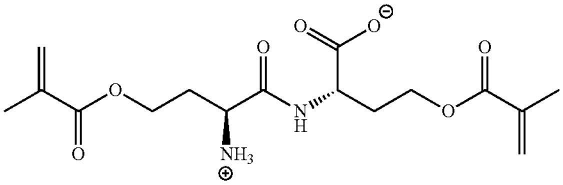<br>N-((S)-2-ammonio-4-(methacryloyloxy)butanoyl)-O-methacryloyl-L-homoserinate | |
| 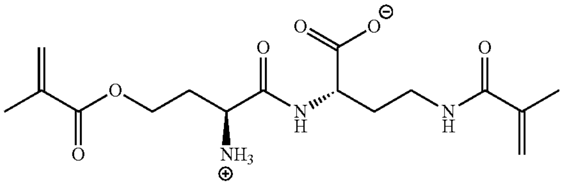 [SMILES: C=C(C)C(=O)NCC[C@H](NC(=O)[C@@H]([NH3+])CCOC(=O)C(=C)C)C(=O)[O-]]<br>(S)-2-((S)-2-ammonio-4-(methacryloyloxy)butanamido)-4-methacrylamidobutanoate | |
| 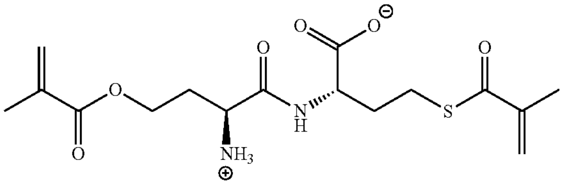 [SMILES: C=C(C)C(=O)OCC[C@H]([NH3+])C(=O)N[C@@H](CCSC(=O)C(=C)C)C(=O)[O-]]<br>N-((S)-2-ammonio-4-(methacryloyloxy)butanoyl)-S-methacryloyl-L-homocysteinate | |

TABLE 1-continued

| Structure/ChemDraw Name | Common Name and/or Comments |
| --- | --- |
| 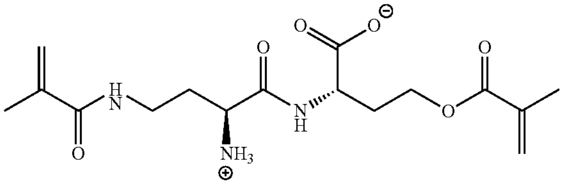 [SMILES: C=C(C)C(=O)NCC[C@H]([NH3+])C(=O)N[C@@H](CCOC(=O)C(=C)C)C(=O)[O-]]<br>N-((S)-2-ammonio-4-methacrylamidobutanoyl)-O-methacryloyl-L-homoserinate | |
| 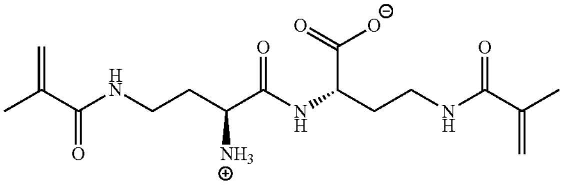 [SMILES: C=C(C)C(=O)NCC[C@H](NC(=O)[C@@H]([NH3+])CCNC(=O)C(=C)C)C(=O)[O-]]<br>(S)-2-((S)-2-ammonio-4-methacrylamidobutanamido)-4-methacrylamidobutanoate | . |
| 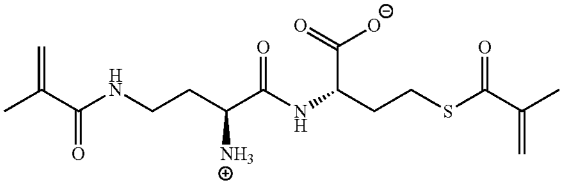 [SMILES: C=C(C)C(=O)NCC[C@H]([NH3+])C(=O)N[C@@H](CCSC(=O)C(=C)C)C(=O)[O-]]<br>N-((S)-2-ammonio-4-methacrylamidobutanoyl)-S-methacryloyl-L-homocysteinate | |
| 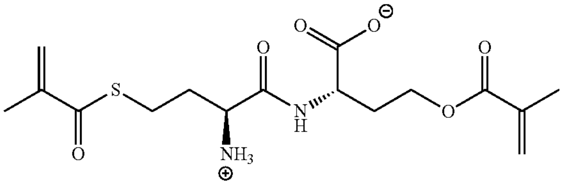 [SMILES: C=C(C)C(=O)SCC[C@H](NC(=O)[C@@H]([NH3+])CCSC(=O)C(=C)C)C(=O)[O-]]<br>N-((S)-2-ammonio-4-(methacryloyithio)butanoyl)-O-methacryloyl-L-homoserinate | |
| 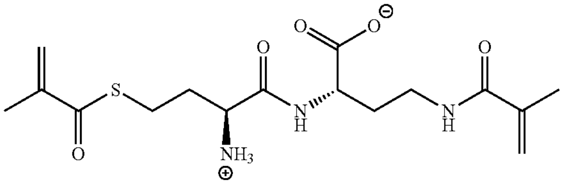<br>(S)-2-((S)-2-ammonio-4-(methacryloyithio)butanamido)-4-methacrylamidobutanoate | |
| 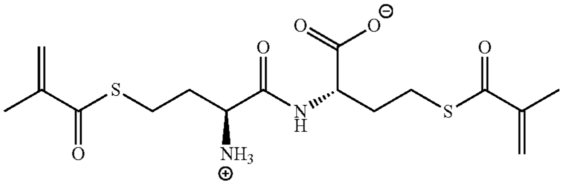<br>N-((S)-2-ammonio-4-(methacryloyithio)butanoyl)-S-methacryloyl-L-homocysteinate | |

TABLE 1-continued

| Structure/ChemDraw Name | Common Name and/or Comments |
| --- | --- |
| 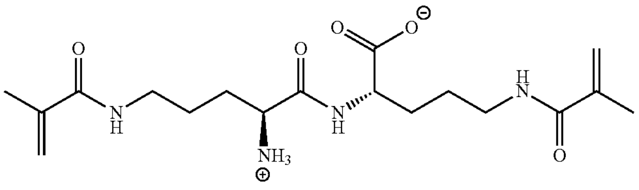 [SMILES: C=C(C)C(=O)NCCC[C@H](NC(=O)[C@@H]([NH3+])CCCNC(=O)C(=C)C)C(=O)[O-]]<br>(S)-2-((S)-2-ammonio-5-methacrylamidopentanamido)-5-methacrylamidopentanoate | |
| 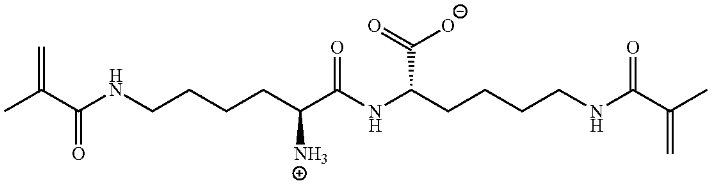 [SMILES: C=C(C)C(=O)NCCCC[C@H](NC(=O)[C@@H]([NH3+])CCCCNC(=O)C(=C)C)C(=O)[O-]]<br>Lysine Dipeptide ([8])<br>14 atom spacer<br>$N^2$-((S)-2-ammonio-6-methacrylamidohexanoyl)-$N^6$-methacryloyl-L-lysinate | |
| 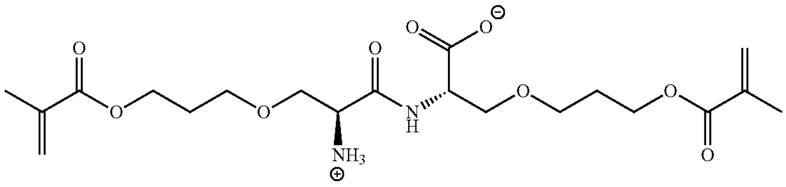 [SMILES: C=C(C)C(=O)OCCCOC[C@H](NC(=O)[C@@H]([NH3+])COCCCOC(=O)C(=C)C)C(=O)[O-]]<br>34 propylene glycol serine dipeptide<br>16 atom spacer<br>N-((S)-2-ammonio-3-(3-(methacryloyloxy)propoxy)propanoyl)-O-(3-(methacryloyloxy)propyl)-L-serinate | |

C. Hydrogels

Crosslinkers within Formulas I-VI may be used to form crosslinked hydrogels, such as polyampholyte hydrogels. A generic formula for certain disclosed hydrogel embodiments according to the present invention is provided below as Formula VII $$(\text{Monomer } 1)_k\text{-}(\text{Crosslinker } 1)_l\text{-}(\text{Monomer } 2)_m \qquad \text{Formula VII.}$$

The primary components of the hydrogel within the scope of Formula VII are monomer 1 and monomer 2, which can be selected independently such that they include a similar or identical polymerizing group 1 and polymerizing group 2 that match the polymerizing group 1 and/or polymerizing group 2 as discussed above concerning crosslinkers within the scope of Formulas I-VI. Monomer 1 and monomer 2 can be any known compound or monomer that provides functionality suitable for incorporation into an efficacious hydrogel, such as a biomedically relevant hydrogel. One notable aspect of disclosed embodiments is the incorporation of monomers that are either zwitterionic themselves or that are charged and mixed in a ratio to maintain the overall zwitterionic neutrality of the resulting hydrogel. Exemplary embodiments according to the present invention have been formed primarily using mixed charged monomer species including 2-carboxyethyl acrylate, [2-(acryloyloxy) ethyl] trimethyl ammonium chloride, 3-sulfopropyl methacrylate, and [2-(methacryloyloxy) ethyl] trimethyl ammonium chloride. Additional zwitterionic monomer species also can be used, such as N-(methacryloxyethyl)-N,N-dimethyl-N-(2-methylcarboxyl)ammonium betaine, N-(methacryloxyethyl)-N,N-dimethyl-N-3-sulfopropyl)ammonium betaine, and 2-methacryloyloxyethyl phosphorylcholine.

Formula VII includes k and m subscripts to describe the number of monomer groups used to form hydrogels. The k and m variables indicate that the number of monomer species range from 0-1000, typically 0-500, more typically 0-100 or less, such as 0-20, or 0-5. Where k and m are 0, the crosslinker itself can polymerize to form a hydrogel. Formula VII also includes the variable l indicating the number of crosslinkers. l is typically determined as a ratio relative to k and m. Moreover, "crosslinker" as used in Formula VII is not limited to a single species, but instead can comprise multiple combinations of crosslinkers within the scope of the present invention, which provides the ability to tune the hydrogel material properties, such as mechanical, degradation, and concentration of any signaling side chains. l may be from 1 to at least 100, more typically 0 to 20, and even more typically 0 to 5. Hydrogels are often made with monomer:crosslinker ratios of 100:1 to 0:1, with particular hydrogels having a ratio of at least as high as 52:1 and at least as low as 6:1.

Exemplary hydrogel structures according to the present disclosure are provided below.

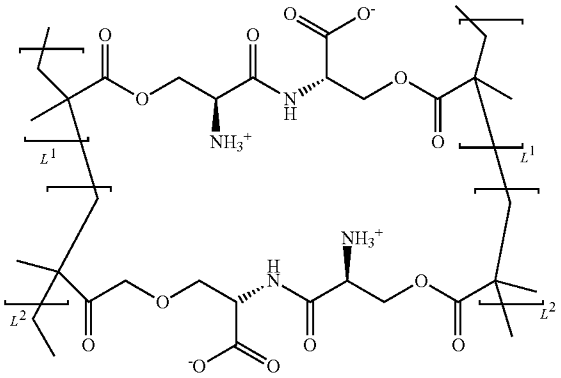

Hydrogel Example 1

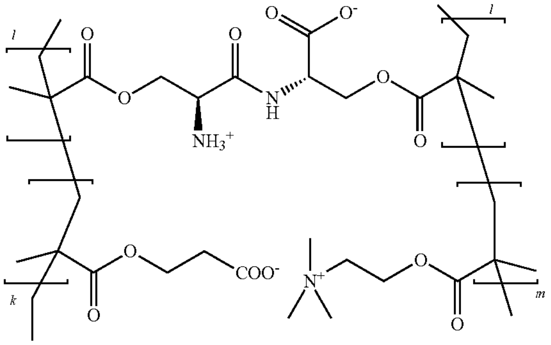

Hydrogel Example 2

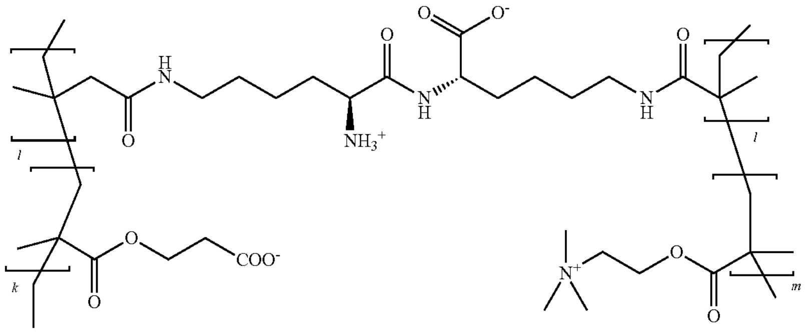

Hydrogel Example 3

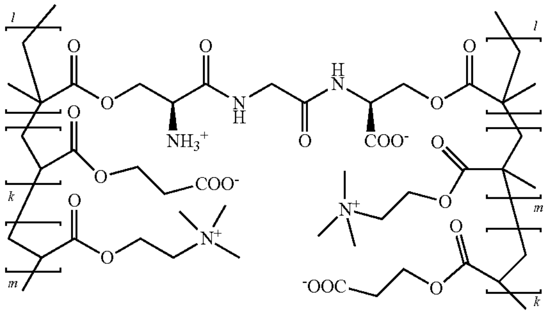

Hydrogel Example 4
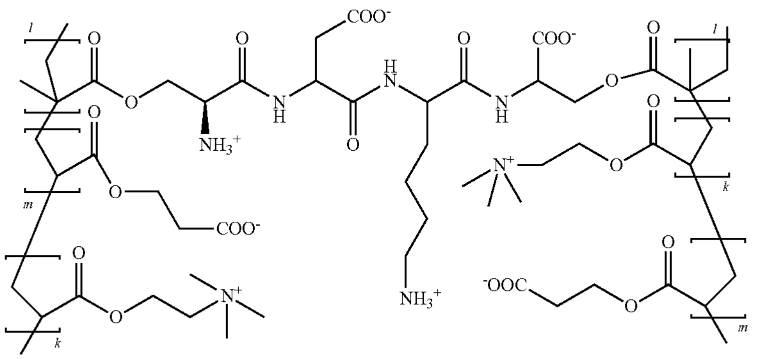
Hydrogel Example 5—Comprising Crosslinker with Pendant Side Chain
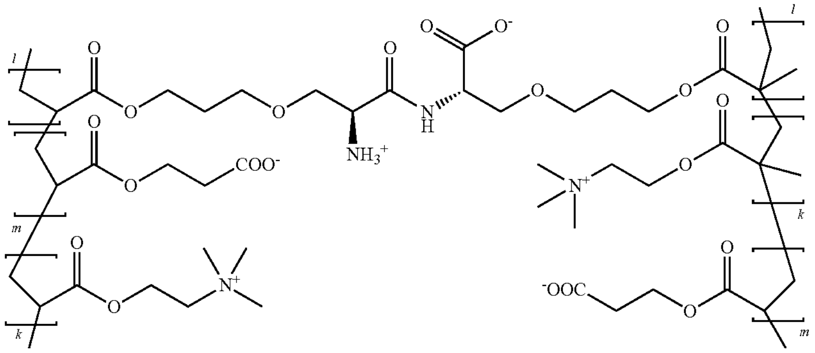
Hydrogel Example 6
Based on Ser-Ser-bis(propylene glycol methacrylate) with Propylene Glycol Forming two External Spacers
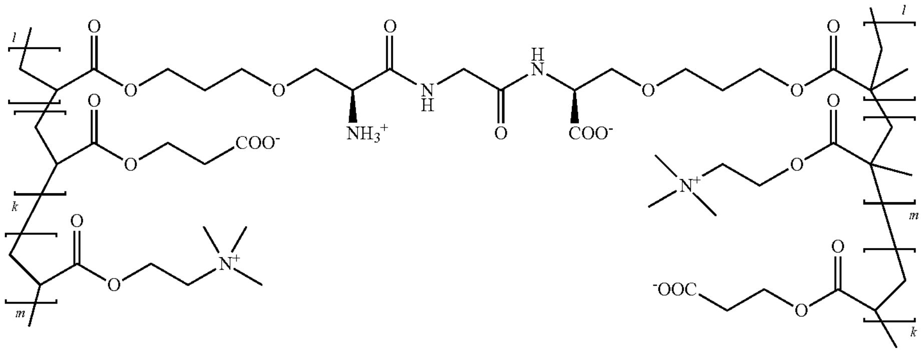

Hydrogel Example 7

Example of a Hydrogel Formed Using a Cross-linker Having Both an Internal Spacer (Methylene=—$CH_2$—) and an External Spacer (Propylene Glycol=—$OCH_2CH_2CH_2O$—)

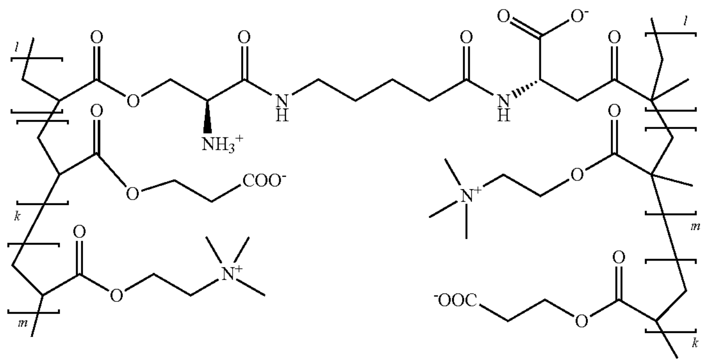

Hydrogel Example 8

Example of a Hydrogel Formed Using a Cross-linker Comprising a Non-Amino Acid Internal Alkyl Spacer (Butyl Spacer=—$CH_2CH_2CH_2CH_2$—)

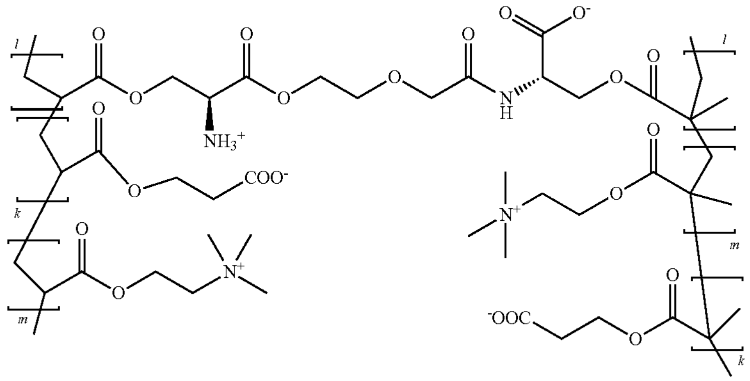

Hydrogel Example 9

Example of a Hydrogel Formed Using a Cross-linker Comprising a Non-Symmetric Internal Spacer (Butyl Spacer=—$OCH_2CH_2OCH_2$—)

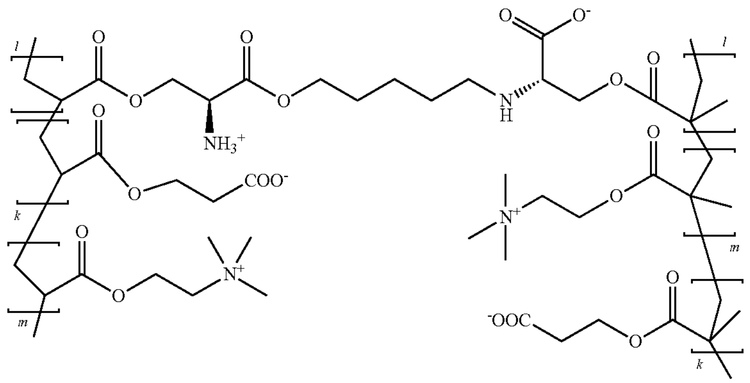

Hydrogel Example 10

Example of a Hydrogel Formed Using a Crosslinker Comprising a Hydrocarbon Spacer (Pentyl $-CH_2CH_2CH_2CH_2CH_2-$) Internal Spacer

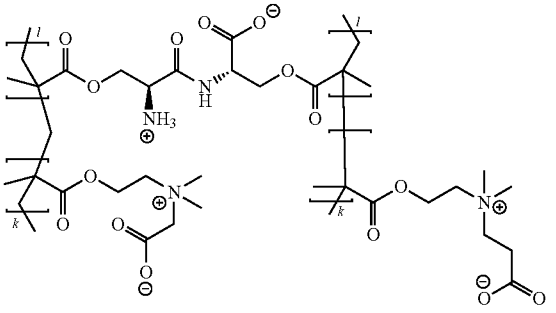

Hydrogel Example 11

Example of a Hydrogel Comprising an N-(Methacryloxyethyl)-N,N-Dimethyl-N-(2-Methylcarboxyl) Ammonium Betaine Zwitterionic Monomer in Combination with a Crosslinker According to the Present Invention

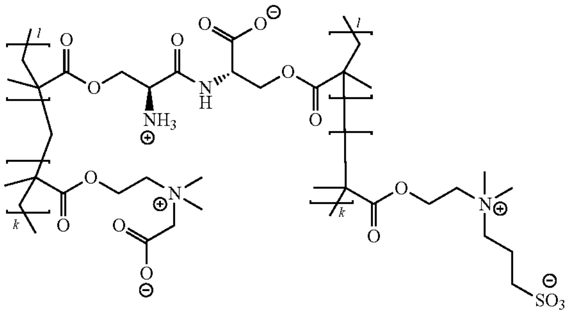

Hydrogel Example 12

Example of a Hydrogel Comprising a Mixture of Zwitterionic Monomers (N-(Methacryloxyethyl)-N,N-Dimethyl-N-(2-Methylcarboxyl)Ammonium Betaine and N-(Methacryloxyethyl)-N,N-Dimethyl-N-3-Sulfopropyl)Ammonium Betaine) in Combination with a Crosslinker According to the Present Invention D. Salts and Counterions The counterion species used during the purification process is a variable that can be controlled to affect the use of crosslinkers and hydrogels made according to the present invention. Crosslinkers and/or hydrogels according to the present can be used for a variety of purposes, some of which may require using a biologically compatible salt. A biologically compatible salt may be derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine.

For certain disclosed embodiments, crosslinkers were purified with an HCl counterion. The counter ion is expected to impact solubility in various solvents during its incorporation into hydrogels for various applications. Alternative particular examples of counterions that can be used include: sulfate, phosphate, citrate, ascorbate, gluconate, and succinate.

IV. Synthesis

A. Crosslinker

A person of ordinary skill in the art will appreciate that compounds according to the present invention can be synthesized by various different effective synthetic schemes. However, the present disclosure provides representative approaches for synthesizing crosslinkers and hydrogels.

Scheme 1, below, provides a retrosynthetic approach for the synthesis of a representative dipeptide based zwitterionic crosslinker, N-Ser-Ser-C dimethacrylate 1.

Scheme 1

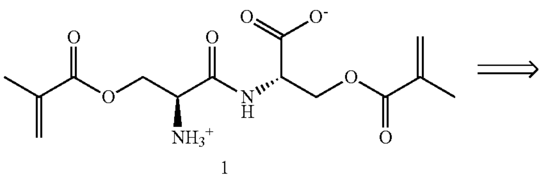

1

-continued

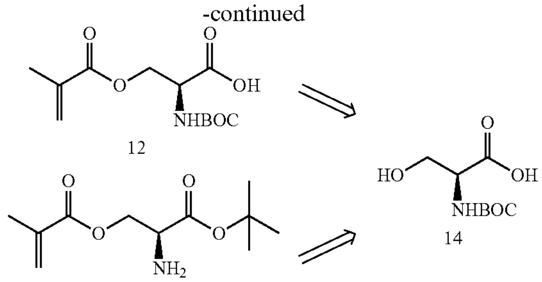

12

13

14

The synthesis of N-Ser-Ser-C dimethacrylate 1 can be accomplished starting with N-Boc-L-serine 14, utilizing a convergent "outside-in" coupling strategy of pre-methacrylated coupling partners 12 and 13, followed by global deprotection. The use of an N-termini tert-butyoxycarbonate (Boc) group was favorable because it was easily removed by trifluoroacetic acid (TFA) leaving the methacrylate functional groups intact. Therefore, the tert-butyl C-termini ester was evaluated to allow for a single overall deprotection step with TFA to create the S—S zwitterionic crosslinker.

Compound 1 was synthesized as indicated below by Scheme 2 starting from N-Boc-L-serine 4

Scheme 2

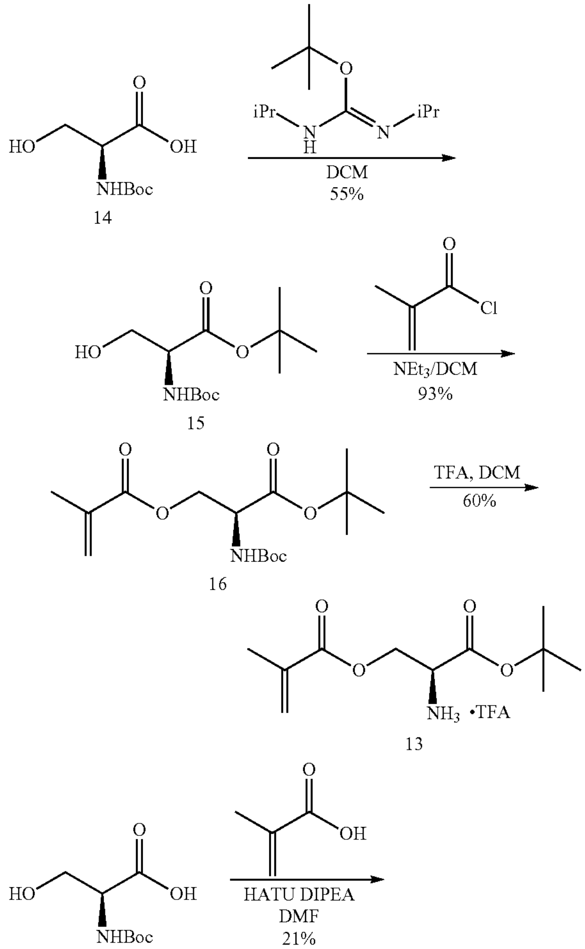

14

15

16

13

14

-continued

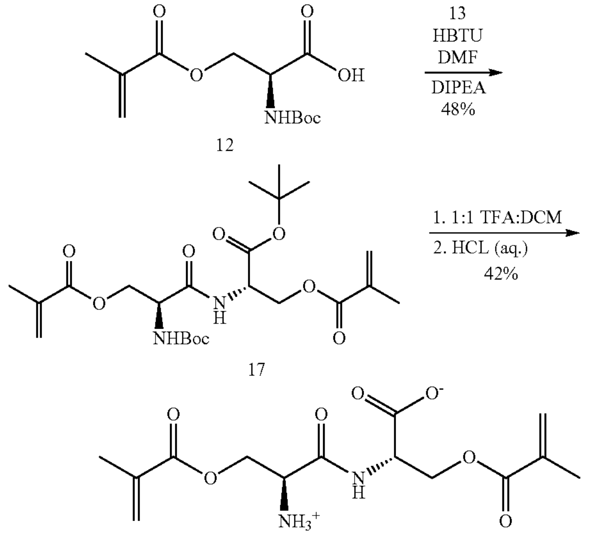

12

17

1

The addition of t-butyl-N,N'-diisopropylcarbamimidate to 14 in DCM afforded the t-butyl protected serine 15 with 55% yield. Next, 15 was treated with methacryloyl chloride in the presence of triethylamine in DCM to give 16 in an excellent 93% yield. While TFA can globally deprotect both Boc and the t-butyl ester, the reaction rate is much faster for the Boc removal, and this was utilized to selectively cleave the Boc group from doubly protected 16, to give the first coupling component 13 as a TFA salt. For the carboxylate coupling partner, N-Boc-L-serine 14 was methacrylated under Steglich-type esterification conditions to provide 12, which quickly supplies the N-protected termini for peptide coupling. HBTU coupling of 12 and 13 produced the protected zwitterionic crosslinker 17. Deprotection with TFA provides the desired crosslinker as a TFA salt. Initially, TFA deprotection was run in $CDCl_3$ in order to monitor the deprotections via 1H NMR, but it can also be run at scale in more conventional, non-deuterated solvents (i.e., DCM). While the Boc group was removed within minutes of TFA addition (as monitored by $^1$HNMR), the reaction took 24 hours in a 1:1 DCM:TFA solution to fully remove the t-butyl protecting group. The isolated TFA salt was then lyophilized in the presence of 25 mM HCl to afford the S—S crosslinker 1 as an HCl salt, ready for hydrogel incorporation. HCl was selected as the counter ion source for uniformity with the counter ions found with the TMA and CAA monomers.

As indicated above in Schemes 1 and 2, part of the crosslinker synthesis protocol involves peptide couplings. This approach can be further highlighted using the preparation of dipeptides, such as Ser-Lys, Lys-Ser, and Lys-Lys in zwitterionic bis(methacrylate/methacrylamide) crosslinkers. This method also can be used to increase the distance between zwitterionic components, which is illustrated by the syntheses of the tripeptide Lys-Gly-Lys dimethacrylamide and Ser-Gly-Ser dimethacrylate. Both methacrylation and peptide coupling were used to prepare crosslinkers within the scope of the present invention. The choice of protecting groups was an important consideration due to the sensitivity of the methacrylate/methacrylamide group. For an outside-in strategy, protected amino acids undergo a methacrylation step followed by peptide coupling or a selective deprotection and subsequent peptide coupling. The initially planned orthogonal protection using Boc groups for the N-termini was well tolerated throughout the reaction schemes, but protection of the C-termini proved more difficult. Eventually, tert-butyl esters (t-Bu) were selected for protecting the C-termini, and t-Bu protecting groups were removed under acidic conditions. This approach is illustrated below by Schemes 3 and 4.

Scheme 3 - Amino Acid (Lysine) $NH_2$ and $CO_2H$ Coupling Partners

Boc-L-Lysine 20

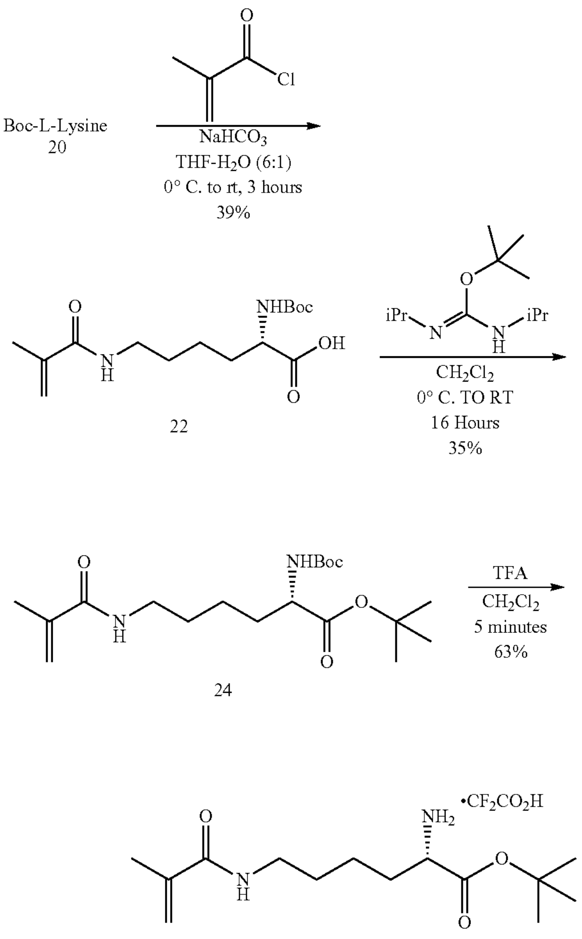

22

24

26

With reference to Scheme 3, the lysine C-terminus coupling agent 22 was obtained in 39% yield from N-Boc-L-lysine 20 by treatment with $NaHCO_3$ and methacryloyl chloride in a 6:1 THF—$H_2O$ solution. Acid 22 was then protected with a tert-butyl group by treatment with tert-butyl N,N'-diisopropylcarbamimidate in $CH_2Cl_2$ to afford 24. Rapid deprotection of the Boc group through treatment with TFA in $CH_2Cl_2$ provided coupling partner 26 as its TFA salt in 63% yield. Peptide coupling was the used to produce N-Lys-Lys-C dimethacrylamide. Additionally, serine derivatives, made previously, could also be coupled to produce mixed methacrylate/methacrylamide dipeptides. Briefly, as shown below in Scheme 4, to prepare 30, N-Boc-L-Serine 28 was protected with a tert-butyl group by treatment with tert-butyl N,N'-diisopropylcarbamimidate in $CH_2Cl_2$. The Boc protecting groups on the N-termini could then be selectively removed by treatment with 1:1 TFA/$CH_2Cl^2$ within minutes or by treatment with 1 M HCl in 1,4-dioxane, while the tert-butyl ester groups on the C-termini remained intact, affording the amine coupling component 26. Methacrylation of 28 under Steglich esterification conditions produced 32.

Scheme 4

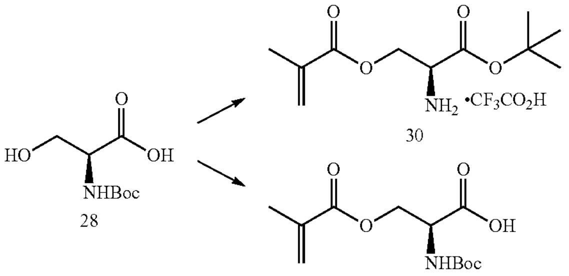

28

30

32

With coupling partners in hand, the peptide-formation reactions were accomplished using HBTU in DMF with DIPEA as a base at room temperature, obtaining the products in variable yields from 47 to 55%, as shown below in Scheme 5.

Scheme 5

22 + 26

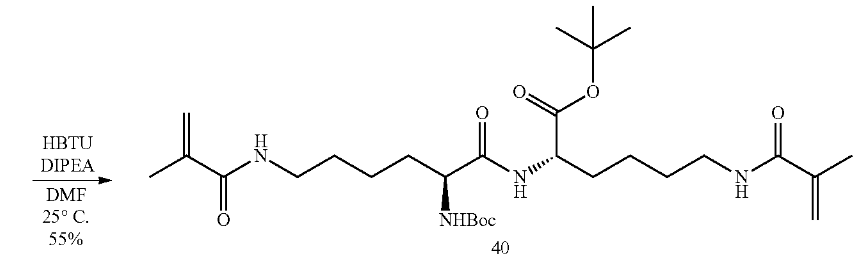

40

N-Lys-Lys-C 46•$CF_3CO_2H$

-continued

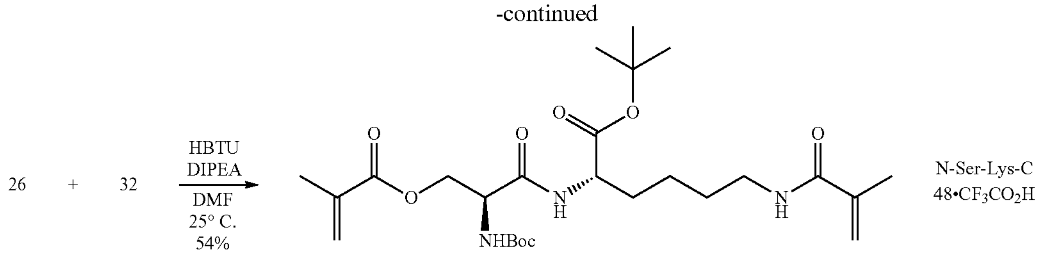

42

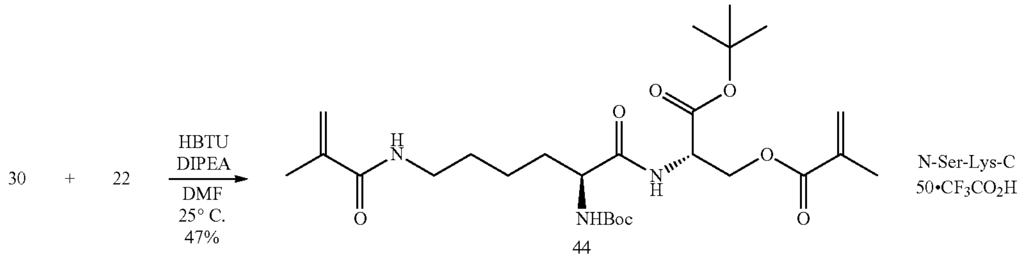

44

The final zwitterionic crosslinker dipeptide products 46, 48 and 50 were prepared by global deprotection of 40, 42 and 44, respectively, by treatment with TFA in chloroform and were isolated as their TFA salts (Scheme 5). These reactions were easily monitored by NMR using TFA-$d^1$ and $CDCl_3$ as solvents. Crosslinker 46 contains a dimethacrylamide species that may be more resistant to hydrolysis compared to dimethacrylates, while providing a longer length (14 atoms between polymerizable units) than that of the N-Ser-Ser-C dimethacrylate crosslinker 1 above and a comparable length to that of a carboxybetaine (e.g., N-(methacryloxyethyl)-N, N-dimethyl-N-(2-methylcarboxyl)ammonium betaine) crosslinker 52, shown below.

52

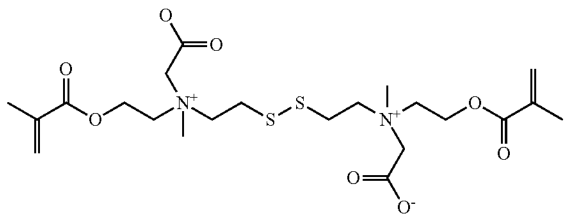

Compounds 48 and 50 provide an equal length (11 atoms) between polymerizable units, but place the zwitterionic components on either the serine or lysine side, respectively, to provide structural differences to affect the hydration layer and/or degradation rate.

To complement the outside-in strategy and to highlight its utility, a glycine spacer has been added between two lysine methacrylamide coupling partners, creating the N-Lys-Gly-Lys-C dimethacrylamide crosslinker 58, and between two serine coupling partners to create the N-Ser-Gly-Ser-C dimethacrylate 62, as shown by Scheme 6, below.

Scheme 6

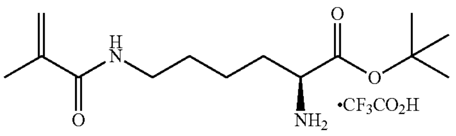

N-Boc-glycine
HBTU, DIPEA
DMF
47%

26

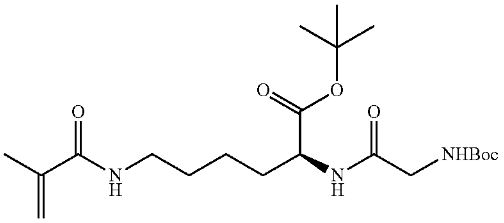

1. TFA, $CH_2Cl_2$
5 minutes
2. 22 PyBOP, DIPEA
DMF, 40%

54

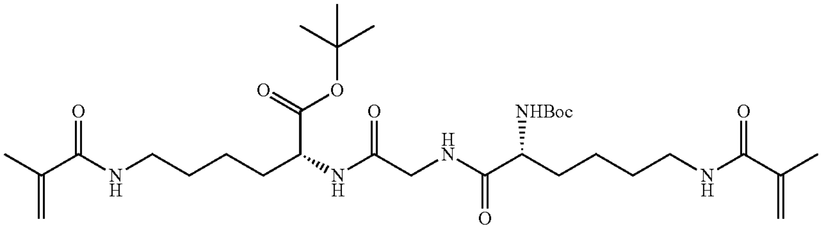

TFA, $CH_2Cl_2$
86%

56

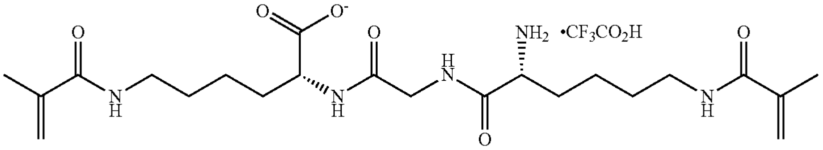

58•$CF_3CO_2H$
N-Lys-Gly-Lys-C

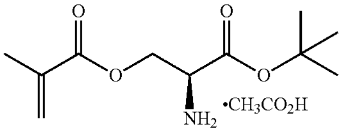

30

N-Boc-glycine
HBTU, DIPEA
DMF
56%

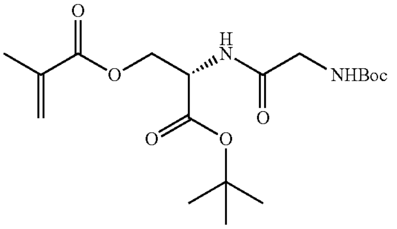

60

1. TFA, $CH_2Cl_2$
5 minutes
2. 32, HBTU DIPEA
DMF
3. TFA, $CH_2Cl_2$
39% for 3 steps

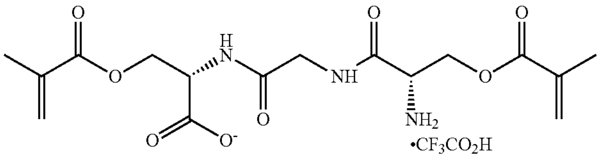

62•$CF_3CO_2H$
N-Ser-Gly-Ser-C

In these compounds, the zwitterionic units are separated by seven atoms, as the distance between charges; the length of the crosslinker, and type of crosslinker type are all important variables for determining the properties of the hydrogel. Under HBTU conditions, 26 was coupled with commercially available N-Boc-glycine to afford the Boc-protected dipeptide 54 in 47% yield. Rapid TFA deprotection and subsequent (1H-1,2,3-benzotriazol-1-yloxy)(tripyrrolidin-1-yl)phosphonium hexafluorophosphate (PyBOP) coupling with 22 gave the fully protected tripeptide 56. In this case, the phosphonium coupling agent gave a slightly higher yield than HBTU. A final global TFA deprotection step produced crosslinker 58 as its TFA salt in 86% yield. The Ser-Gly-Ser dimethacrylate was synthesized in a similar manner starting from 30 with coupling to N-Boc-glycine using HBTU to give 60. Sequential Boc deprotection, coupling of 32, and global deprotection gave the tripeptide dimethacrylate 62.

IV. Discussion of Disclosed Embodiments

The present invention provides a method for synthesizing amino-acid or peptide-based zwitterionic crosslinkers and the integration of such crosslinkers into polyampholyte hydrogels. As an example, an N-Ser-Ser-C dimethacrylate (S—S) crosslinker was incorporated into a polyampholyte hydrogel composed of an equimolar mixture of [2-acryloyloxy ethyl] trimethyl ammonium chloride (TMA) and 2-carboxyethyl acrylate (CAA). The TMA:CAA formulation has previously been demonstrated to be resistant to nonspecific protein adsorption, while also being capable of facilitating cell recruitment and attachment through covalently attached proteins like fibrinogen, albeit when synthesized with a triethylene glycol dimethacrylate crosslinker. S—S crosslinked TMA:CAA hydrogels were evaluated to determine their physical, nonfouling, and biocompatibility characteristics. The performance of the S—S crosslinked hydrogel was directly compared to a TMA:CAA hydrogel formed with a diethylene glycol dimethacrylate (DEG) crosslinker due to similarities in the overall crosslinker lengths (10 versus 9 backbone atoms, respectively). Representative hydrogel formulations demonstrating the similarity in the overall crosslinker length can be seen in FIG. 1. The physical characteristics of the two hydrogels showed no significant differences, and the S—S crosslinked hydrogel exhibited identical nonfouling performance, while demonstrating greater biocompatibility when compared to DEG crosslinked hydrogels. These results suggest that our convergent coupling strategy is a promising approach for developing a broad family of peptide-based zwitterionic crosslinkers to directly address the shortcomings of using ethylene glycol based crosslinkers for in vivo applications.

First, the physical properties of hydrogels formed with each crosslinker species were compared. Following hydrogel formation, samples were measured and then were allowed to soak for 24 hours in PBS to determine their extent of swelling. The DEG crosslinked hydrogels swelled ~70% larger than their initial size while the S—S crosslinked samples swelled ~73%, as summarized in Table 2, below.

TABLE 2

| Measured Property | DEG Hydrogel | S-S Hydrogel |
|---|---|---|
| Swelling (%) | 70.86 ± 3.70 | 73.46 ± 4.11 |
| Percent Hydration (%) | 96.71 ± 0.19 | 97.09 ± 0.51 |
| Shore 00 Hardness | 22.43 ± 2.88 | 18.85 ± 4.91 |

Hydrogels reach swelling equilibrium after 24 hours, as verified for hydrogels crosslinked with both species. No significant additional swelling occurred in either crosslinked system following the initial 24 hours.

Water content is an important consideration when evaluating the biocompatibility of hydrogels, so the percent hydration was determined for both sets of hydrogels. Following full hydration (48 hours in DI water) and dehydration in a desiccator, hydrogels formed with both the DEG and the S—S crosslinkers exhibited percent hydration values of ~97% (Table 2).

The cellular response to implanted biomaterials can be influenced by the mechanical properties of the material. Accordingly, the surface hardnesses for both hydrogel systems were measured using a Shore 00 hardness durometer after samples had reached their equilibrium swollen state (24 hours of soaking in pH 7.4 PBS). As before, both hydrogels demonstrated similar properties, with the DEG and S—S crosslinked hydrogels measuring ~22 and ~19 Shore 00, respectively (Table 2).

Most importantly, all three physical assessments for the DEG and S—S crosslinked hydrogels demonstrated no statistical differences in the results. This establishes that differences established between the two hydrogels in the subsequent protein adsorption and cellular adhesion work are directly attributable to differences in the underlying chemistry.

Figure 2:
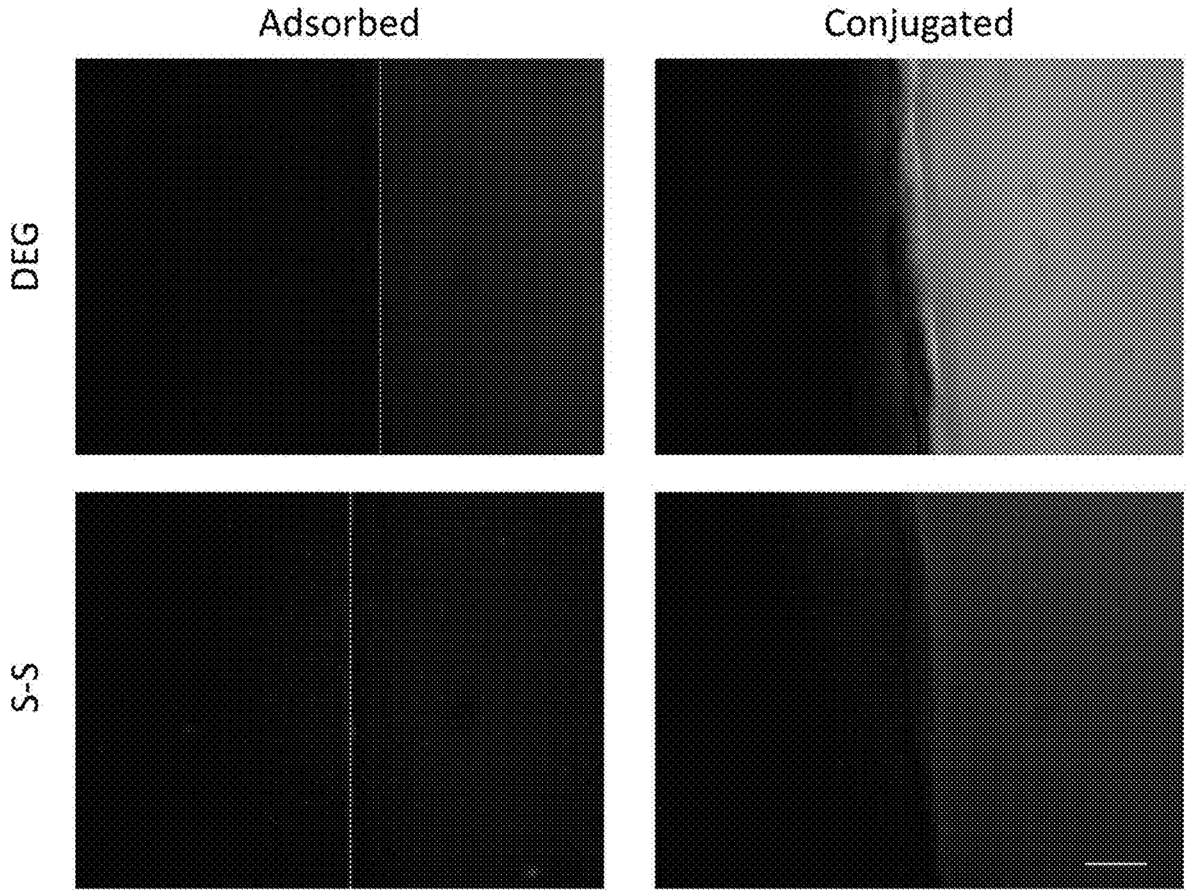
FIG. 2 provides fluorescent microscopy images of diethylene glycol dimethacrylate (DEG) and N-Ser-Ser-C dimethacrylate (S—S) hydrogels when bovine serum albumin-fluorescein isothiocyanate conjugate (FITC BSA) is adsorbed or conjugated to the surface, further including a blank control hydrogel on the left-hand side in every image that was used for background subtraction, and where the scale bar represents 200 μm that applies to all images presented by FIG. 2.

One aspect of the present invention is that zwitterionic crosslinkers enhance the nonfouling performance of polyampholyte hydrogels. An initial assessment of nonfouling was completed using FITC BSA as this has been accepted in the art as a basis to demonstrate nonfouling properties of polyampholyte systems. See, for example, S. L. Haag and M. T. Bernards, Enhanced Biocompatibility of Polyampholyte Hydrogels, Langmuir, 2020, 36(13), 3292-3299; and E. Mariner, S. L. Haag and M. T. Bernards, Impacts of crosslinker chain length on the physical properties of polyampholyte hydrogels, Biointerphases, 2019, 14, 031002. Following exposure to FITC BSA, hydrogel samples formed with both crosslinkers were evaluated using fluorescent microscopy and representative images are shown in FIG. 2. To account for any background fluorescence, the left-hand side of each image is a corresponding control hydrogel that has not been exposed to FITC BSA, and this side of the image was used for background subtraction. The right-hand side is a hydrogel exposed to FITC BSA (the hydrogel intersection is marked with a white line for clarity) and any nonspecifically adsorbed protein is visualized with a green FITC emission. FIG. 2 establishes that there were no quantifiable differences in the nonfouling performance of hydrogels formed with either crosslinker species.

In addition to nonfouling, the ability to deliver biomolecules from a nonfouling platform is also important for initiating targeted cellular interactions. Polyampholyte hydrogels have previously been shown to have this ability, without impacting the underlying nonfouling properties of the hydrogels. However, subtle differences in the synthesis procedures have also been shown to influence the conjugation levels, making it important to verify that crosslinkers according to the present invention, such as the S—S crosslinker, does not impact this property.

Accordingly, FITC BSA was conjugated to the surface of hydrogels crosslinked with either DEG or S—S using EDC/NHS conjugation chemistry. Representative fluorescent microscopy images following conjugation are shown in FIG. 2. As before, a blank hydrogel was again used as a control for background subtraction as shown on the left-hand side of each image. FIG. 2 establishes that both DEG and S—S hydrogels show a dramatic increase in fluorescence, indicating the successful conjugation of FITC BSA. However, DEG crosslinked hydrogels demonstrated markedly more fluorescence than S—S crosslinked hydrogels, indicating a greater level of protein conjugation to the DEG crosslinked hydrogel compared to the S—S crosslinked hydrogel.

The qualitative assessment of the nonfouling performance (FIG. 2) indicated there were no significant differences in the behavior of the hydrogels crosslinked with either the DEG or S—S species. However, previous hydrogels have demonstrated resistance to nonspecific protein adsorption from single proteins in buffer only to fail in more complex environments. Therefore, hydrogels crosslinked by both options were also evaluated for their ability to prevent MC3T3-E1 cell adhesion even when in the presence of 10% fetal bovine serum (FBS). The inclusion of 10% FBS mimics the conditions used for standard cell culture, as this level of complex protein solution is sufficient to facilitate significant cell attachment and growth to tissue culture polystyrene (TCPS). Following hydrogel exposure to cells in supplemented alpha minimum essential medium (α-MEM) for 2 hours, the cells were stained with a live-dead viability kit. The alive cells stained green with calcein AM indicating intracellular esterase activity whereas the dead cells stained red with ethidium homodimer driven by compromised cellular membranes. The representative confocal microscopy images shown in FIG. 3 indicate the presence of very few cells on both the DEG and S—S crosslinked systems. These results further confirm that both hydrogel formulations demonstrate nonfouling properties even upon exposure to more complex systems.

Figure 3:
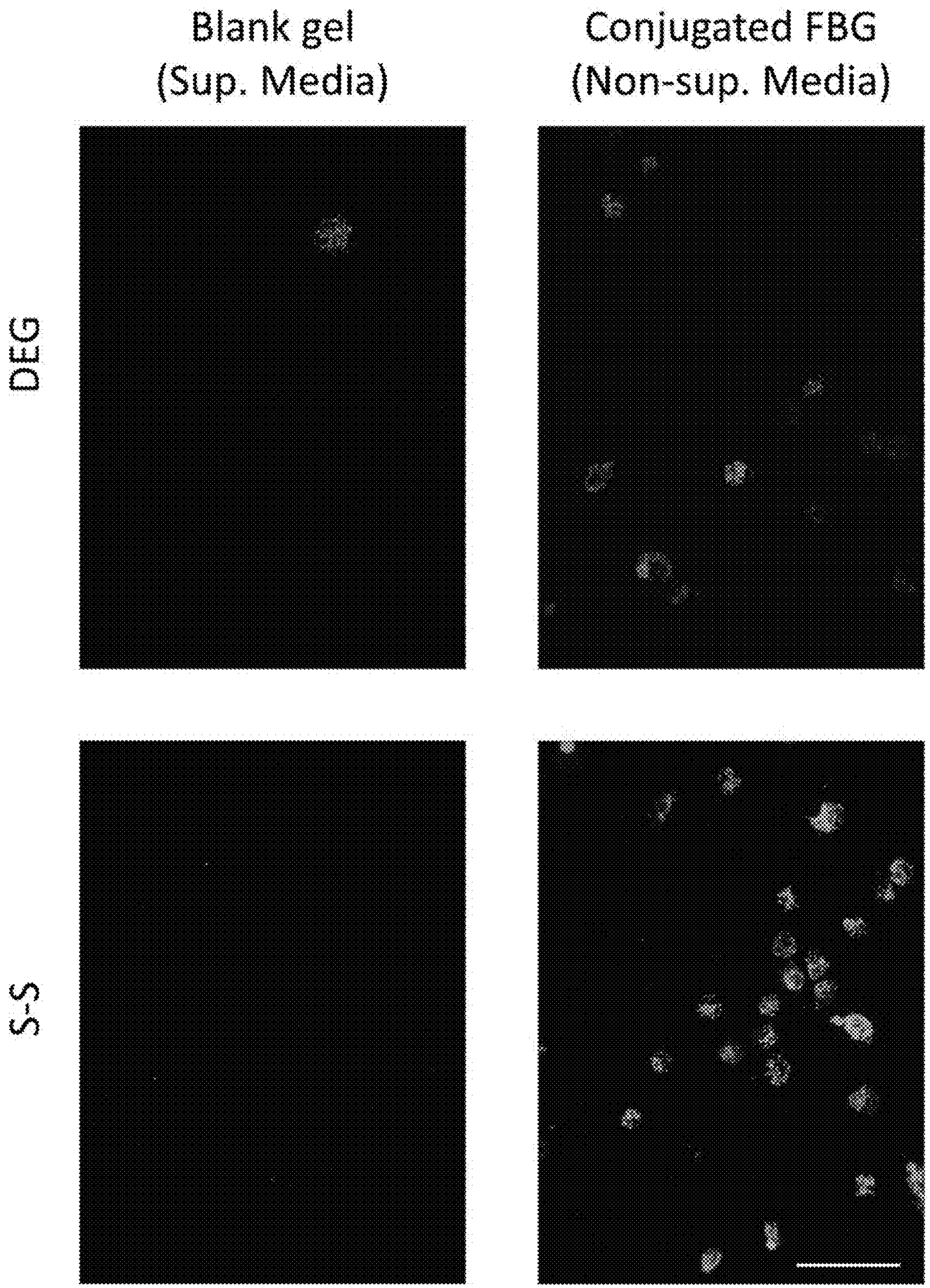
FIG. 3 provides confocal microscopy images of MC3T3-E1 cell adhesion to polyampholyte hydrogels in the presence of supplemented media (left) and MC3T3-E1 cell adhesion to hydrogels with conjugated fibrinogen from human plasma (FBG) (non-supplemented media, right), where cells were stained with a live-dead viability stain with live cells dyed green and dead cells dyed red, and where the scale bar represents 100 μm that applies for all images presented by FIG. 3.
Figure 4A:
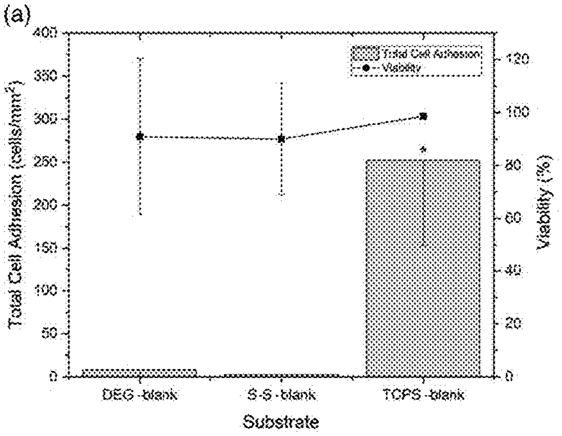
FIGS. 4A and 4B are graphs of total cell adhesion (cells/$mm^2$) versus viability (%) and illustrating mean±standard deviation of MC3T3-E1 cell adhesion to polyampholyte hydrogels with (a) supplemented media, or (b) conjugated fibrinogen from human plasma (FBG) (non-supplemented media), where * indicates a statistically significant difference from all other groups at a 95% confidence level ($p<0.05$).

Quantitative evaluation of multiple images from replicate samples confirms the representative confocal microscopy images as summarized in FIG. 4A. MC3T3-E1 cell adhesion to the positive TCPS control surface was extremely high (~250 cells per $mm^2$), as expected, and the cells also demonstrated excellent viability. In contrast, cell adhesion to both polyampholyte hydrogel systems was essentially nonexistent, with cell adhesion levels of ~8 cells per $mm^2$ and ~2 cells per $mm^2$ for DEG and S—S crosslinked hydrogels, respectively. These cells were still viable, but these extremely low adhesion numbers clearly demonstrate the nonfouling properties of the polyampholyte hydrogels in this complex environment. The qualitative assessment of protein conjugation established that greater levels of conjugated protein were present on the DEG crosslinked hydrogels (FIG. 2) when compared to the S—S crosslinked hydrogels. However, it is equally important to evaluate the bioactivity of the biomolecule being delivered from each platform. This was assessed by conjugating fibrinogen (FBG), a well-known cell adhesion promoting protein, to both hydrogels, followed by exposure to MC3T3-E1 cells in non-supplemented media. No FBS was included in this evaluation to specifically isolate the cell adhesion bioactivity of the conjugated FBG. Representative confocal microscopy images of cell attachment to both hydrogel systems are shown in FIG. 3. Cells are present on both hydrogels with similar rounded morphologies. However, the S—S hydrogel appears to have higher initial cell adhesion levels.

Figure 4B:
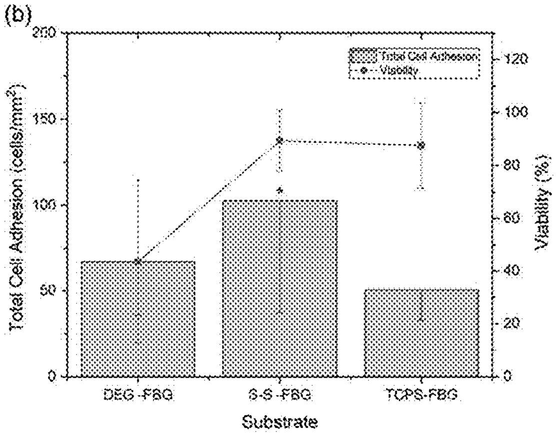

Cell adhesion levels to polyampholyte hydrogels with conjugated FBG was quantified over multiple samples and images and the results are summarized in FIG. 4B. A positive control surface of FBG adsorbed to TCPS was included as a baseline for cell adhesion. Both DEG and S—S crosslinked polyampholyte hydrogels exhibit higher cell adhesion levels than that seen on the TCPS-FBG control surface. Further, the level of cell adhesion to the S—S crosslinked hydrogels (~103 cells per $mm^2$) is statistically greater than that seen for the other two groups. Additionally, the viability of cells attached to the S—S crosslinked hydrogels is ~90%, while the viability of cells attached to the DEG crosslinked system is significantly lower at ~44%. When the viability results are coupled with the cell attachment levels, it is clear that the S—S crosslinked polyampholyte hydrogel demonstrates significantly better biocompatibility. Further, despite having lower protein conjugation levels (FIG. 2), the S—S crosslinked polyampholyte hydrogel also promotes the most bioactive presentation of FBG. This may be due to a more favorable conformation being imparted to FBG when bound to the S—S crosslinked hydrogel or better cell accessibility to the bioactive RGD domain of FBG due to the lower surface coverage of conjugated protein.

Based on these results, zwitterionic crosslinkers according to the present invention demonstrate significant promise for use in nonfouling polymer scaffolds. The swelling behavior, percent hydration, and surface hardness of the S—S crosslinked hydrogel are all comparable to DEG crosslinked hydrogels. Additionally, nonfouling performance for hydrogels comprising crosslinkers according to the present invention was demonstrated in both simple and complex environments, with no discernable differences from the DEG control. Although a decrease was seen in the level of conjugated protein, targeted cell adhesion through conjugated proteins was greater on the S—S crosslinked hydrogels relative to the DEG crosslinked hydrogels and positive controls. Together these results demonstrate the efficacy of crosslinkers and polyampholyte hydrogels according to the present invention for tissue engineering applications.

V. Hydrogel Applications

Polymer hydrogels are widely utilized in a number of fields, including biomedical applications. As a result, hydrogels according to the present invention can be used to make contact lenses, drug delivery vehicles, tissue engineering and regeneration platforms, catheters, coatings for implants and implantable sensors, such as glucose sensors.

VI. Examples

The following examples are provided to illustrate features of certain disclosed embodiments. A person of ordinary skill in the art will appreciate that the scope of the invention is not limited to the particular features of these examples.

Materials

Boc-L-Serine, tert-butyl N,N'-diisopropylcarbamimidate, trifluoroacetic acid (TFA), and 2-(1H-benzotriazol-1-yl)-1,1,3,3-tetramethyluronium hexafluorophosphate (HBTU), were purchased from AK Scientific (Union City, CA). N,N'-Diisopropylethylamine (DIPEA) and methacryloyl chloride were purchased from Acros Organics (Fair Lawn, NJ). Methacrylic acid was purchased from Alfa Aesar (Tewksbury, MA). Triethylamine was purchased from EMD Millipore (Burlington, MA). Ethyl acetate (EtOAc), hexanes, dichloromethane (DCM), N,N'-dimethylformamide (DMF), and concentrated hydrochloric acid (HCl) were purchased from Thermo Fisher (Waltham, MA). Deuterated solvents, chloroform ($CDCl_3$), and methanol-d4 ($CD_3OD$) were purchased from Cambridge Isotopes (Tewksbury, MA). Fibrinogen from human plasma (FBG), ethylene glycol, phosphate buffered saline (PBS), DEG, TMA, CAA, ammonium persulfate (APS), sodium metabisulfite (SMS), N-(3-dimethylaminopropyl)-N'-ethylcarbodiimide hydrochloride (EDC), N-hydroxysuccinimide (NHS), bovine serum albumin-fluorescein isothiocyanate conjugate (FITC BSA), and sodium hydroxide (NaOH) were purchased from Sigma-Aldrich (St. Louis, MO). Alpha-minimum essential medium (α-MEM) with nucleosides, fetal bovine serum (FBS), sodium chloride (NaCl), and a live/dead cytotoxicity kit for mammalian cells were purchased from Thermo Fisher Scientific (Hampton, NH). Penicillin-streptomycin, tris hydrochloride, trypan blue, trypsin (0.25%) ethylenediaminetetraacetic acid (EDTA) (1×), trypsin soybean inhibitor, and paraformaldehyde were purchased from VWR (Radnor, PA). Ethanol was purchased from Greenfield Global (Toronto, Canada). MC3T3-E1 subclone 14 cells (batch number 61723894) were purchased from the American Type Culture Collection (ATCC; CRL-2594) (Manassas, VA).

All reaction products were fully characterized using $^1H$ and $^{13}C$ NMR on either a Bruker AVANCE 300 or AVANCE 500 MHz instrument and results were obtained in $CDCl_3$ (referenced to 7.26 ppm for $^1H$ and 77.16 ppm for $^{13}C$) or methanol-d4 (referenced to 3.31 ppm for $^1H$ and 49.15 ppm for $^{13}C$). Coupling constants (J) are provided in Hz. The multiplicities of the signals are described using the following abbreviations: s=singlet, br s=broad singlet, d=doublet, t=triplet, q=quartet, dd=doublet of doublets, dq=doublet of quartets, dsep=doublet of septets; tt=triplet of triplets, m=multiplet, app=apparent. Reaction progress was monitored by thin-layer chromatography on silica gel plates (60-F254), observed under UV light. Column chromatography was performed using silica gel (particle size 40-63 μm). High resolution mass spectrometry (HRMS) was performed on a Waters Q-Tof Premier Quadrupole-Time of Flight Mass Spectrometer.

Example 1

This example concerns synthesis of exemplary cross-linkers according to the present disclosure.

A. tert-butyl (tert-butoxycarbonyl)-L-serine (15):

A solution of commercially available Boc-L-serine (4) (1.00 g, 6.2 mmol) in dichloromethane (100 mL) was added to tert-butyl N, N'-diisopropylcarbamimidate (2.48 g, 12.4 mmol). The mixture was stirred in an ice bath for 30 minutes, and then allowed to warm to room temperature (RT) overnight with continual stirring. Hexanes (10 mL) were added and the reaction was stirred for 15 minutes. The suspension was filtered through a pad of celite to remove the diisopropylurea byproduct, and the filtrate was concentrated in vacuo. The resulting residue was purified by column chromatography (4:1 EtOAc/hexanes) and concentrated in vacuo to yield 700 mg (55%). 1H NMR (500 MHz, Methanol-d4) δ 4.08 (t, J=4.6 Hz, 1H), 3.81 (dd, J=11.2, 5.0 Hz, 1H), 3.76 (dd, J=11.1, 4.1 Hz, 1H), 1.48 (s, 9H), 1.45 (s, 9H). 13C NMR (500 MHz, d3-MeOD) δ 171.782, 158.045, 83.048, 80.802, 63.378, 58.174, 28.846, 28.440.

B. (S)-3-(tert-butoxy)-2-((tert-butoxycarbonyl)amino)-3-oxopropyl methacrylate (16)

Triethylamine (209.12 mg, 2.06 mmol) was added to a solution of tert-Butyl (tert-butoxycarbonyl)-L-serine (180 mg, 0.68 mmol) in dichloromethane (5 mL), followed by dropwise addition of methacryloyl chloride (215.97 mg, 2.06 mmol) at 0° C. The reaction mixture was slowly warmed to room temperature and stirred until TLC analysis (80% EtOAc/hexanes) indicated complete consumption of the starting material. Saturated aqueous $NaHCO_3$ was added to the crude mixture and the aqueous phase was extracted with EtOAc (3×10 mL). The combined organic phases were washed with brine (10 mL), dried using $MgSO_4$, filtered, and concentrated in vacuo. The resulting residue was purified by column chromatography to yield 172 mg (93%). 1H NMR (300 MHz, Methanol-d4) δ 6.15-6.08 (m, 55H), 5.64 (q, J=1.7 Hz, 1H), 4.44-4.36 (m, 4H), 1.92 (t, J=1.4 Hz, 3H), 1.47-1.44 (m, 19H). 13C NMR (300 MHz, $CDCl_3$) δ 174.627, 169.930, 82.661, 64.079, 28.434, 28.128.

C. (S)-2-amino-3-(tert-butoxy)-3-oxopropyl methacrylate•TFA (13)

tert-Butyl (tert-butoxycarbonyl)-L-serine methacrylate (16) (57.33 mg, 0.214 mmol) was dissolved in 1 mL dichloromethane and 150 μl trifluoroacetic acid TFA were added at room temperature and stirred for 3 hours. The solvent was removed in vacuo and the material was used for the next step without any further purification. Yield: 44.13 mg of 3•TFA (60%). $^{1}H$ NMR (300 MHz, Chloroform-d) δ 6.12 (s, 1H), 5.58 (d, J=6.1 Hz, 1H), 4.62 (s, 1H), 4.30 (s, 1H), 1.87 (d, J=5.8 Hz, 3H), 1.45 (s, 9H). $^{13}C$ NMR (126 MHz, Chloroform-d) δ 167.306, 166.761, 165.750, 161.852, 135.127, 135.053, 127.556, 116.62 (q, J=, 85.450, 62.164, 53.272, 27.969, 27.763, 27.700, 18.014, 17.941.

D. (tert-butoxycarbonyl)-L-serine methacrylate (12)

A solution of methacrylic acid (258.27 mg, 3.0 mmol) in DMF (10 mL) was cooled to 0° C. to which HBTU (912.55 mg, 2.4 mmol) was added. The reaction mixture was warmed to room temperature and stirred for an additional 1 hour. Boc-L-serine (14) (500 mg, 2.4 mmol) was then added to the reaction mixture followed by DIPEA (801.35 mg, 6.2 mmol) and the mixture was stirred until TLC indicated complete disappearance of the starting material. The reaction mixture was added to water and extracted with ethyl acetate (10 mL×5), dried over MgSO4 and purified using column chromatography to give 140 mg (21% yield). $^{1}H$ NMR (300 MHz, Methanol-d4) δ 6.12 (s, 1H), 5.63 (dt, J=3.3, 1.6 Hz, 1H), 4.48 (d, J=8.5 Hz, 2H), 4.42-4.33 (m, 1H), 1.96-1.89 (m, 5H), 1.45 (d, J=2.8 Hz, 9H). $^{13}C$ NMR (126 MHz, Methanol-d4) δ 172.671, 168.268, 157.667, 137.295, 126.700, 80.797, 65.951, 65.255, 61.490, 54.142, 38.889, 28.665, 20.870, 18.297, 14.459.

E. (S)-3-(tert-butoxy)-2-((tert-butoxycarbonyl)amino)-3-oxopropyl methacrylate (17): (tert-butoxycarbonyl)-L-serine methacrylate (71.45 mg, 0.261 mmol) was dissolved in DMF to which HBTU (99.50 mg, 0.261 mmol) was added in one portion. The reaction mixture was stirred for an hour before adding (S)-2-amino-3-(tert-butoxy)-3-oxopropyl methacrylate TFA (50 mg, 0.218 mmol) and DIPEA (87.36 mg, 0.676 mmol). The mixture was stirred for an additional three hours and the solvent was removed under in vacuo, dissolved in water, and extracted with ethyl acetate (5×10 mL). The crude was then subjected to column chromatography for further purification. Yield: 40 mg (48%). $^{1}H$ NMR (500 MHz, Methanol-d4) δ 6.12 (tq, J=2.0, 0.9 Hz, 2H), 5.65 (p, J=1.6 Hz, 1H), 5.62-5.61 (m, 1H), 4.68 (dd, J=5.1, 3.9 Hz, 1H), 4.51 (d, J=5.8 Hz, 0H), 4.46 (dd, J=11.4, 5.2 Hz, 1H), 4.44-4.37 (m, 2H), 4.31 (dd, J=11.2, 6.9 Hz, 1H), 1.92 (dd, J=1.6, 1.0 Hz, 3H), 1.92 (dd, J=1.6, 1.0 Hz, 4H), 1.46 (s, 9H), 1.45 (s, 9H). $^{13}C$ NMR (126 MHz, Methanol-d4) δ 171.673, 169.271, 168.315, 168.092, 137.285, 137.230, 126.977, 126.850, 83.804, 81.040, 65.328, 65.025, 54.967, 53.908, 28.664, 28.187, 18.362.

F. O-methacryloyl-N-(0-methacryloyl-L-seryl)-L-serine HCl (1):

(S)-3-(tert-butoxy)-2-((tert-butoxycarbonyl)amino)-3-oxopropyl methacrylate (40 mg, 0.08 mmol) was dissolved in 4 mL of a 1:1 dichloromethane:trifluoroacetic acid solution and stirred at room temperature until all the starting material was consumed (24 hours). The solvent was removed in vacuo and the final compound was isolated as a TFA-salt. Yield: 19 mg (70%). $^{1}H$ NMR (500 MHz, Methanol-d4) δ 6.22-6.18 (m, 2H), 6.12 (s, 1H), 5.67 (s, 1H), 5.64 (s, 1H), 4.81 (t, J=4.4 Hz, 1H), 4.57 (d, J=4.6 Hz, 2H), 4.50 (d, J=4.5 Hz, 2H), 4.37 (t, J=4.5 Hz, 1H), 1.92 (d, J=6.5 Hz, 6H). $^{13}C$ NMR (126 MHz, Methanol-d4) δ 171.48, 168.33, 167.92, 167.44, 162.20 (br s), 137.12, 136.67, 127.74, 127.04, 118.65 (q, J=286 Hz), 116.48, 64.83, 63.82, 53.46, 18.23.

The TFA salt (60 mg, 0.135 mmol) was suspended in 25 mL of 25 mM HCl and lyophilized for 16 hours two times to reveal 31 mg of the HCl salt (1) as a white solid (63% yield). $^{13}C$ NMR (126 MHz, Methanol-d4) δ 171.31, 168.22, 167.21, 137.22, 136.73, 127.74, 126.98, 64.83, 63.77, 53.51, 18.28. HRMS-ESI (m/z): [M+H]+ calculated for $CH_{14}H_{20}N_2O_7$ 329.13; found 329.135.

Example 2

This example concerns synthesis of an exemplary DEG hydrogel according to the present disclosure.

Two different hydrogels were synthesized and will be referenced by which crosslinker species was used in the hydrogel (DEG or S—S; FIG. 1). The DEG hydrogels were synthesized by mixing 4 mmol of TMA and 4 mmol of CAA monomers on a stir plate. Then 2 mL of a buffer solution comprising ethanol, ethylene glycol, and 6.7 M NaOH in a 1:1.5:1.5 ratio, respectively, was added to the monomer mixture. Next, 0.152 mmol of DEG crosslinker was added, resulting in a monomer to crosslinker ratio of 52.6 to 1. The solution was mixed well and then degassed with a vacuum pump for 30 seconds. Following degas, 32 μL of 40% (w/w) APS and 32 μL of 15% (w/w) SMS were added to initiate the polymerization reaction. The solution was gently mixed and then pipetted into a mold consisting of a ⅛" polytetrafluorethylene spacer clamped between two microscope slides. The reaction proceeded for one hour at 60° C. Following polymerization, the gel was removed from the mold and used in subsequent tests.

Example 3

This example concerns synthesis of an exemplary S-S hydrogel according to the present disclosure. A stock solution was created by mixing 8 mmol of TMA, 8 mmol of CAA, 4 mL of buffer solution (ethanol:ethylene glycol:6.7M NaOH in a 1:1.5:1.5 ratio) and 0.304 mmol of the S—S crosslinker. Again, the final monomer to crosslinker ratio was 52.6 to 1. The stock solution was continuously stirred on a stir plate until aliquots were removed for polymerization. For each hydrogel, ⅙ of the stock solution was mixed with 10.7 μL of 40% (w/w) APS and 10.7 μL of 15% (w/w) SMS to polymerize. The solution was mixed gently, then pipetted into the same hydrogel mold as described for Example 2, and the polymerization reaction proceeded for one hour at 60° C. Following polymerization, the gel was removed from the mold and used in subsequent tests.

Example 4

This example concerns characterization of an S-S hydrogel according to the present disclosure.

Swelling: Immediately following polymerization, the length and width measurements of the hydrogels were determined using a caliper. All of the gels were then placed in petri dishes with pH 7.4 PBS for 24 hours. The hydrogels were remeasured after 24 hours of soaking. One set of samples continued to soak in pH 7.4 PBS for an additional 48 hours with additional measurements collected every 24 hours. Following data collection, the gels were used for the surface hardness and percent water weight experiments described below. Each experiment was completed in duplicate at a minimum and the experiment was repeated thrice for a total n=11.

Surface Hardness: After the hydrogels had soaked for 24 hours in pH 7.4, the gels were removed and 00 shore hardness measurements were taken for each gel with a durometer. A minimum of two replicate samples were evaluated in each experiment and the experiment was repeated thrice (n=7).

Percent Weight: Following 24 hours soaking in pH 7.4 phosphate buffered saline, hydrogels were then soaked in deionized water for an additional 48 hours. Afterwards, the gels were removed, patted dry, and weighed. The samples were then placed into a desiccator and monitored until they were no longer visibly shrinking. At this point, samples were weighed daily until their weight remained consistent. The wet and dry weights were then used to calculate the weight percent of water in the hydrogels. A minimum of two replicate samples were evaluated in each experiment and the experiment was repeated four times (n=9).

BSA Non fouling and Conjugation: After the hydrogels soaked in pH 7.4 phosphate buffered saline for 24 hours as described above, they were punched into 8 mm disks with a biopsy punch and each punch was placed into a single well of a 24-well plate. For the protein non-fouling assessment, the hydrogel samples were exposed to a 30 μL droplet of 1 mg/mL bovine serum albumin-fluorescein isothiocyanate conjugate for 15 minutes. The samples were then rinsed 5 times with pH 7.4 PBS, followed by imaging with a Nikon Eclipse Ti-U light and fluorescent microscope with a 10× objective and NIS Elements BR 3.1 software.

Additional 8 mm samples were used for protein conjugation evaluation in a 24-well plate. Hydrogels were first exposed to 1 mL of pH 4.5 phosphate buffered saline for 15 minutes. After 15 minutes, the pH 4.5 phosphate buffered saline was removed and 1 mL of 0.05 M N-(3-dimethylaminopropyl)-N'-ethylcarbodiimide hydrochloride (EDC) and 0.2 M N-hydroxysuccinimide (NHS) was added to each well for 7 minutes. Following removal of the EDC/NHS solution, a 30 μL droplet of 1 mg/mL FITC BSA was placed on the top of each hydrogel for 15 minutes. Afterwards, each well received 1 mL of pH 8.9 phosphate buffered saline for 30 minutes followed by 1 mL of pH 7.4 phosphate buffered saline for 40 minutes. The resulting hydrogels were then imaged as described above. Three samples were run in each experiment and tests were run in triplicate for both the non-fouling and conjugation studies, giving an n=9.

Example 5

This example concerns MC3T3-E1 Cell Studies:

Adhesion: MC3T3-E1 cells were cultured using passages 5-10. S—S and DEG hydrogels were synthesized and soaked in pH 7.4 phosphate buffered saline for 24 hours, as described above. Then 8 mm disks were punched using a biopsy punch and each sample was placed into a single well of a 24 well plate. One set of hydrogels underwent conjugation with fibrinogen from human plasma, using the procedures described above with 1 mL of 1 mg/mL fibrinogen from human plasma in place of the 30 μL droplet of 1 mg/mL bovine serum albumin-fluorescein isothiocyanate conjugate.

As the conjugation procedure was occurring, three wells of tissue culture polystyrene were exposed to 1 mg/mL fibrinogen from human plasma for 30 minutes as a positive control surface. In addition, cells were prepared for seeding Briefly, confluent cells were rinsed twice with 10 mL tris buffer and then detached from the surface with 2 mL trypsin ethylenediaminetetraacetic acid. The trypsin ethylenediaminetetraacetic acid was then gently removed and the cells were suspended in 5 mL of 5 mg/mL soybean trypsin inhibitor in phosphate buffered saline. The cell suspension was then centrifuged for 5 minutes at 1,000 rpm. Next, the cells were washed twice with 8 mL of 1 mg/mL bovine serum albumin in non-supplemented alpha-minimum essential medium, and then resuspended in 5 mL of non-supplemented alpha-minimum essential medium. Cells were counted with a hemocytometer and then diluted into two suspensions of $1\times10^5$ cells/mL: one with non-supplemented alpha-minimum essential medium, and the other in media supplemented with 10% fetal bovine serum.

Following conjugation and fibrinogen from human plasma adsorption, all of the hydrogels and fibrinogen from human plasma adsorbed tissue culture polystyrene surfaces were rinsed trice with tris buffer. One mL of non-supplemented media with $1\times10^5$ cells/mL was seeded into wells with fibrinogen from human plasma containing samples (conjugated and adsorbed). One mL of supplemented media (10% FBS) with $1\times10^5$ cells/mL was seeded into wells with blank hydrogels (no prior protein) and onto blank TCPS surfaces (control). The well plate was placed in an incubator for 2 hours after which the cell solution was removed and the cells were stained and imaged as described below.

Fluorescent Staining/Imaging: After 2 hours of incubation, the Alpha-minimum essential medium was removed from all of the wells. The cells were then stained with a fluorescent live-dead stain by adding 100 μL of 0.5 μM ethidium homodimer-1 and 1.5 μM calcein AM in phosphate buffered saline to each well. The well plate was returned to the incubator for 20 minutes, after which the samples were removed. Paraformaldehyde (4%; 0.5 mL) was added to each of the TCPS control conditions to fix the cells in those wells. The hydrogel samples were immediately imaged on a Nikon Spinning Disk Confocal Microscope with a 20× objective. After the hydrogels were imaged, the tissue culture polystyrene conditions were imaged on a Nikon Eclipse Ti-U light and fluorescent microscope with a 10× objective and NIS Elements BR 3.1 software. A minimum of 3 images were taken for each well, 3 samples were evaluated in each experiment, and the experiments were repeated in triplicate leading to n=27.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A crosslinker, having a Formula I (Polymerizing Group 1)$_s$-(Amino Acid)$_u$-(Polymerizing Group 2)$_y$ Formula I, where:

polymerizing group 1 and polymerizing group 2 independently are provided by reaction with an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, any combination thereof; and u is 2 to 100.

2. The crosslinker according to claim 1, wherein the crosslinker is zwitterionic between a pH of from 2.5 to 10.

3. The crosslinker according to claim 1, wherein each amino acid is a naturally occurring amino acid selected to provide zwitterionic functional groups at a pH of from 2.5 to 10.

4. The crosslinker according to claim 1, wherein s and y are 1 and u is 2 to 10.

5. The crosslinker according to claim 1, wherein polymerizing group 1 and polymerizing group 2 independently are provided by reaction with an alkyl acrylate, alkyl acrylamide, alkyl acrylonitrile, or (hydroxyalkyl) acrylate.

6. The crosslinker according to claim 1, wherein polymerizing group 1 and polymerizing group 2 independently are provided by reaction with a methacrylate, ethylacrylate, propylacrylate, methacrylamide, ethylacrylamide, propylacrylamide, methacrylonitrile, ethylacrylonitrile, propylacrolynitrile, or (hydroxyethyl) methacrylate.

7. The crosslinker according to claim 1, where u is 2 to 10, and each amino acid independently is selected from serine, lysine, aspartic acid, glutamic acid, arginine, histidine, cysteine, threonine, or tyrosine.

8. The crosslinker according to claim 1, having a Formula II

[(Polymerizing Group 1)$_s$-(Amino Acid 1)$_u$-(Internal Spacer)$_v$-(Amino Acid 2)$_w$-(Polymerizing Group 2)$_y$] Formula II where:

polymerizing group 1 and polymerizing group 2 are independently provided by an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, for any combination thereof;

u and w sum to at least 2, and are independently 0 to 100;

each internal spacer independently is selected from an amino acid, a peptide, an aliphatic spacer, a heteroaliphatic spacer, a cyclic spacer, a heterocyclic spacer, an aryl spacer, a heteroaryl spacer, or any combination thereof, wherein each internal spacer independently for each occurrence comprises 1 to 20 atoms; and v is 0 to 20.

9. The crosslinker according to claim 8, comprising at least one internal spacer selected from an amino acid, peptide, methylene ($-CH_2-$), ethyl ($-CH_2CH_2-$), propyl ($-CH_2CH_2CH_2-$), butyl ($-CH_2CH_2CH_2CH_2-$), pentyl ($-CH_2CH_2CH_2CH_2CH_2-$), hexyl ($-CH_2CH_2CH_2CH_2CH_2CH_2-$),

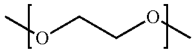, 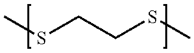,
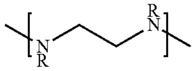, 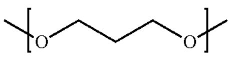,
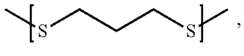, 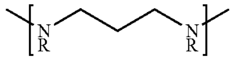,
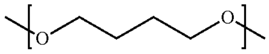,
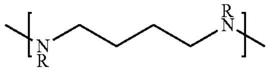,
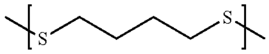,
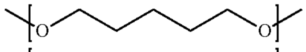,
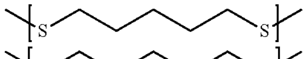,
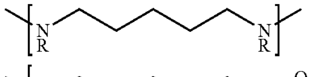,
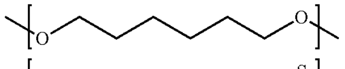,
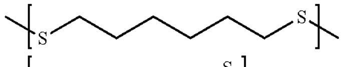,
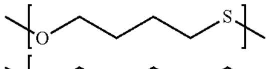,
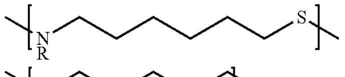,
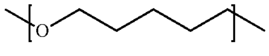, -continued

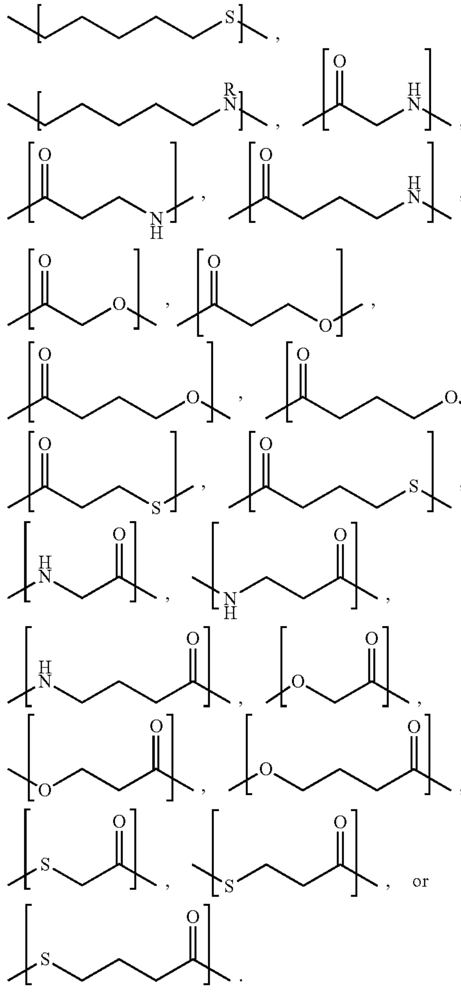

10. The crosslinker according to claim 1, having a Formula III

[(Polymerizing Group 1)$_s$-[(External Spacer 1)$_t$-(Amino Acid)$_u$-(External Spacer 2)$_x$]-(Polymerizing Group 2)$_y$] Formula III, where:

polymerizing group 1 and polymerizing group 2 independently are provided by reaction with an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, or any combination thereof;

u is 2 to 100;

external spacer 1 and external spacer 2 independently are selected from an amino acid, a peptide, an aliphatic spacer, a heteroaliphatic spacer, a cyclic spacer, a heterocyclic spacer, an aryl spacer, a heteroaryl spacer, or any combination thereof, wherein each external spacer 1 and external spacer 2 independently for each occurrence comprises 1 to 20 atoms; and t and x are 0 to 20.

11. The crosslinker according to claim 1 having a Formula IV,

[(Polymerizing Group 1)$_s$-(Spacer 1)$_t$-(Amino Acid 1)$_u$-(Spacer 2)$_v$-(Amino Acid 2)$_w$-(Spacer 3)$_x$-(Polymerizing Group 2)$_y$] Formula IV, where:

polymerizing group 1 and polymerizing group 2 independently are provided by reaction with an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, or any combination thereof;

u and w sum to at least 2, and independently are 0 to 100;

spacer 1, spacer 2 and spacer 3 independently are selected from an amino acid, a peptide, an aliphatic spacer, a heteroaliphatic spacer, a cyclic spacer, a heterocyclic spacer, an aryl spacer, a heteroaryl spacer, and any and all combinations thereof, wherein each spacer 1, spacer 2, and spacer 3 independently comprises 1 to 20 atoms; and t, v and x independently are 0 to 20.

12. The crosslinker according to claim 1 having a Formula V

Formula V

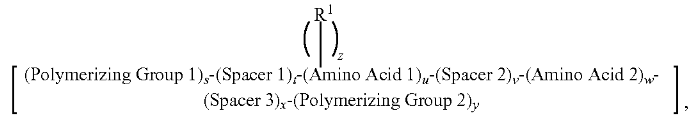

where:

polymerizing group 1 and polymerizing group 2 independently are provided by reaction with an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, or any combination thereof;

u and w sum to at least 2, and are independently 0 to 100;

spacer 1, spacer 2 and spacer 3 independently are selected from an amino acid, a peptide, an aliphatic spacer, a heteroaliphatic spacer, a cyclic spacer, a heterocyclic spacer, an aryl spacer, a heteroaryl spacer, or any combination thereof, wherein each spacer 1, spacer 2, and spacer 3 independently for each occurrence comprises 1 to 20 atoms;

t, v and x are independently 0 to 20;

$R^1$ is a $C_1$-$C_{10}$ amine, $C_1$-$C_{10}$ carboxylic acid, $C_1$-$C_{10}$ alkene, $C_1$-$C_{10}$ alkyne, $C_1$-$C_{10}$ nitrile, $C_1$-$C_{10}$ alcohol, $C_1$-$C_{10}$ thiol, $C_1$-$C_{10}$ phenol, $C_4$-$C_{10}$ aryl, or $C_5$-$C_{10}$ heteroaryl; and z is 0 to 10.

13. The crosslinker according to claim 12, where $R^1$ is $C_1$-$C_{10}NR^2R^3$ or $C_1$-$C_{10}CO_2R^4$, and where $R^2$, $R^3$, and $R^4$ independently are selected from hydrogen or lower alkyl.

14. The crosslinker according to claim 12, where $R^1$ is a $C_1$-$C_6$-alkyl amine, $C_1$-$C_6$-alkyl ammonium, $C_1$-$C_6$—COOH, or $C_1$-$C_6$—$COO^-$.

15. The crosslinker according to claim 1 having a Formula VI

Formula VI

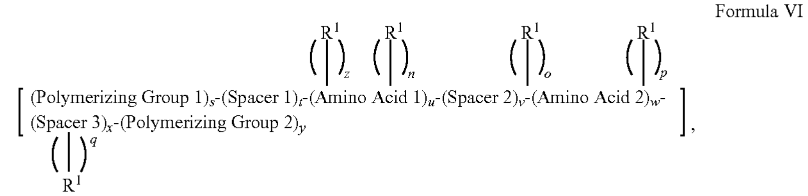

where:

polymerizing group 1 and polymerizing group 2 independently are provided by reaction with an acrylate, alkyl acrylate, acrylamide, alkyl acrylamide, acrylonitrile, alkyl acrylonitrile, or a (hydroxyalkyl) acrylate;

each of s and y independently are from 1 to 10;

each amino acid independently is any naturally occurring amino acid, any non-naturally occurring amino acid, or any combination thereof;

u and w sum to at least 2, and independently are 0 to 100;

spacer 1, spacer 2 and spacer 3 are independently selected from an amino acid, a peptide, an aliphatic spacer, a heteroaliphatic spacer, a cyclic spacer, a heterocyclic spacer, an aryl spacer, or a heteroaryl spacer, wherein each spacer 1, spacer 2, and spacer 3 independently for each occurrence comprises 1 to 20 atoms;

t, v and x independently are 0 to 20;

each $R^1$ independently is a $C_1$-$C_{10}$ amine, $C_1$-$C_{10}$ carboxylic acid, $C_1$-$C_{10}$ alkene, $C_2$-$C_{10}$ alkyne, $C_1$-$C_{10}$ nitrile, $C_1$-$C_{10}$ alcohol, $C_1$-$C_{10}$ thiol, $C_6$-$C_{10}$ phenol, $C_6$-$C_{10}$ aryl, or $C_5$-$C_{10}$ heteroaryl; and z, n, o, p and q independently are 0 to 10.

16. The crosslinker according to claim 1, selected from

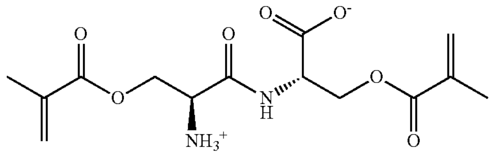
,
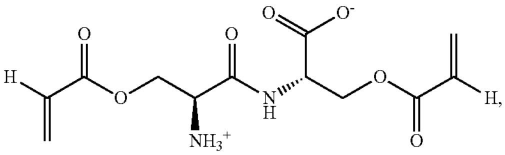
,
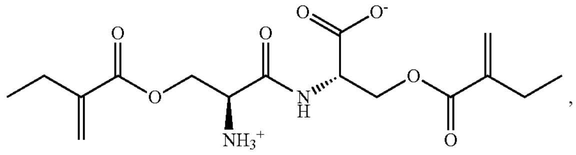
,
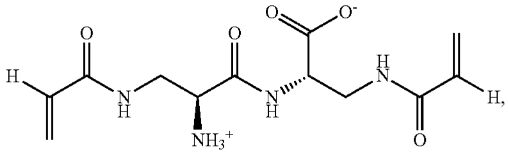
,
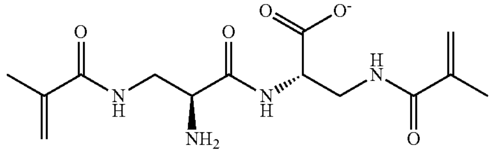
,
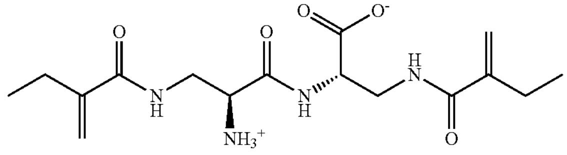
, -continued

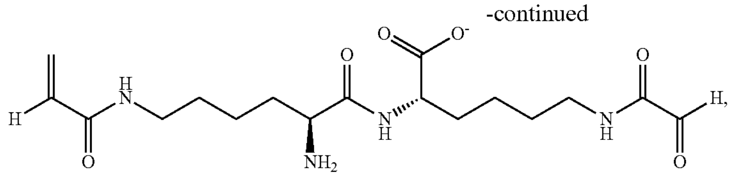
,

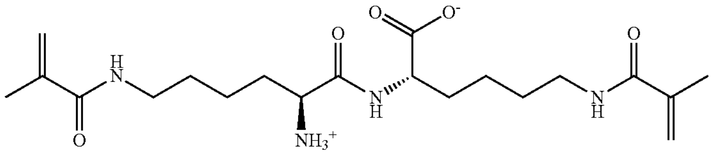
,

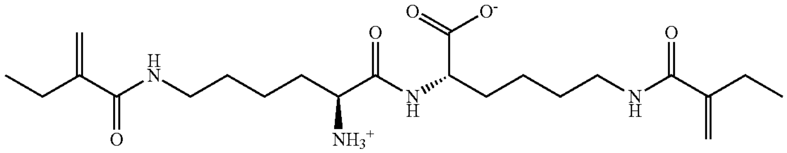
,

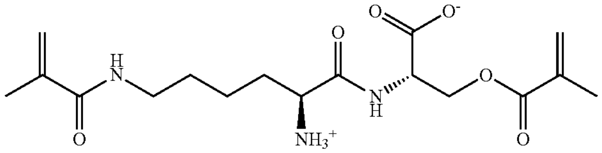
,

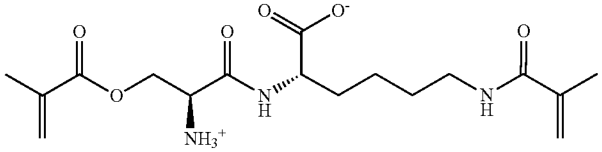
,

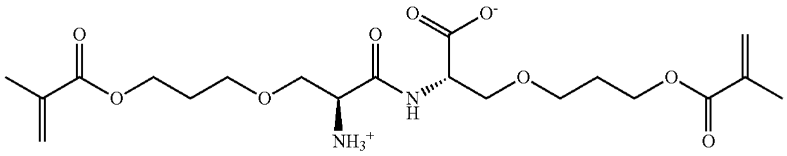
, or

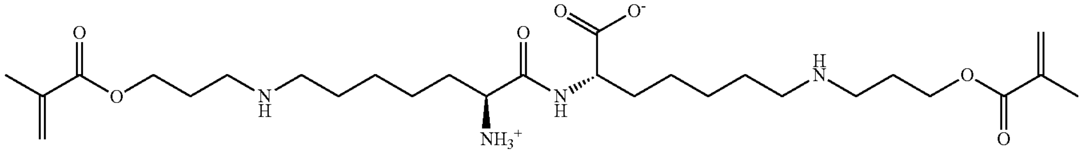
.

17. A hydrogel, having a Formula VII $$(\text{Monomer } 1)_k\text{-(Crosslinker } 1)_l\text{-(Monomer } 2)_m \qquad \text{Formula VII}$$

where:

each monomer 1 and monomer 2 independently is provided by reaction with an acrylate, alkyl acrylate, acrylamide, alkyl acrylamide, acrylonitrile, alkyl acrylonitrile, or a (hydroxyalkyl) acrylate;

k and m independently are 0 to 1000;

crosslinker 1 is the crosslinker according to claim 1; and l is 1 to 100.

18. The hydrogel according to claim 17, wherein monomer 1 and monomer 2 comprise a charged monomer.

19. The hydrogel according to claim 17, wherein monomer 1 and monomer 2 independently are selected from 2-carboxyethyl acrylate, [2-(acryloyloxy) ethyl] trimethyl ammonium chloride, 3-sulfopropyl methacrylate, [2-(methacryloyloxy) ethyl] trimethyl ammonium chloride, N-(methacryloxyethyl)-N,N-dimethyl-N-(2-methylcarboxyl)ammonium betaine, N-(methacryloxyethyl)-N,N-dimethyl-N-3-sulfopropyl)ammonium betaine, or 2-methacryloyloxyethyl phosphorylcholine.

20. The hydrogel according to claim 17, selected from:
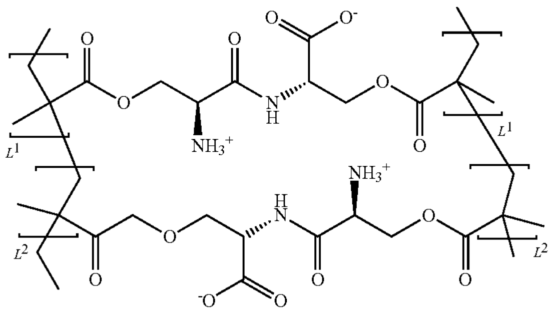
,
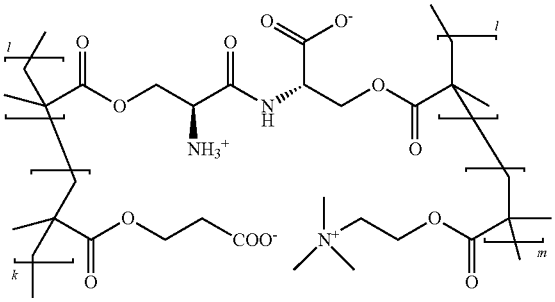
,
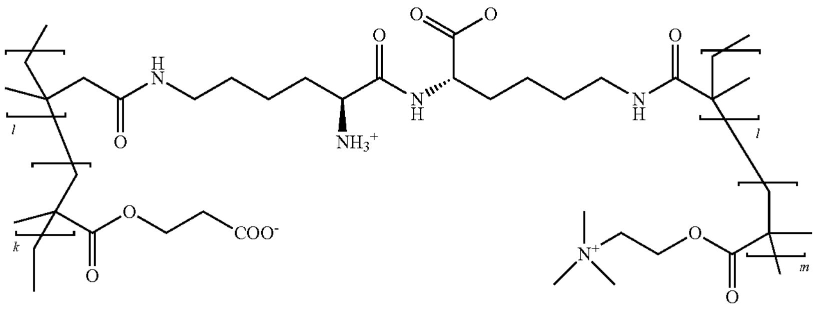
,
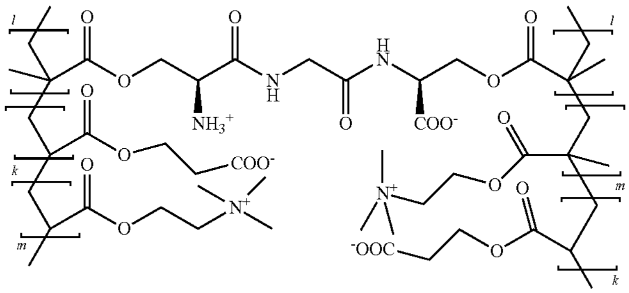
,
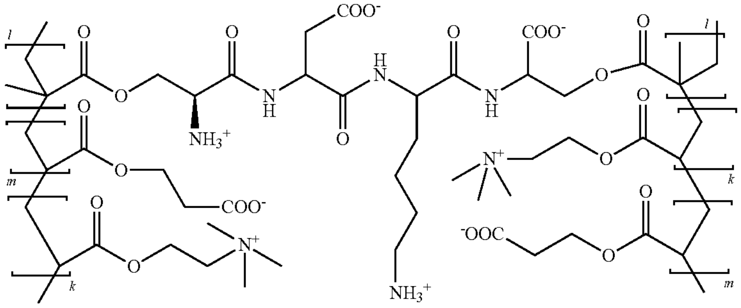
,
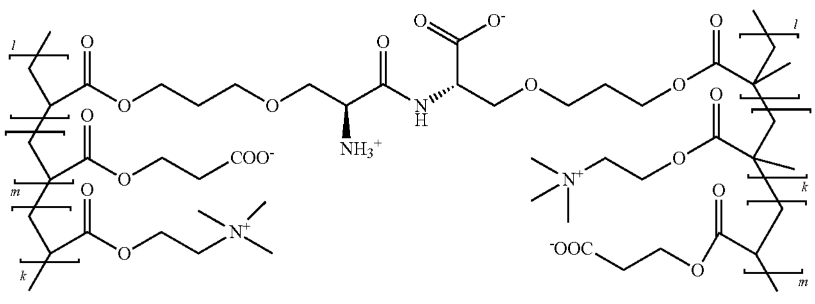
, -continued
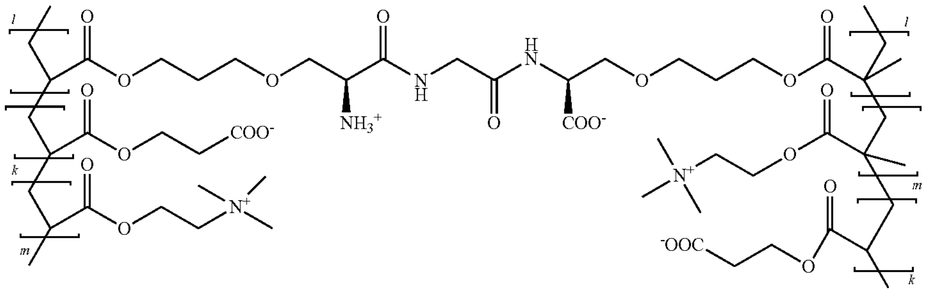
,
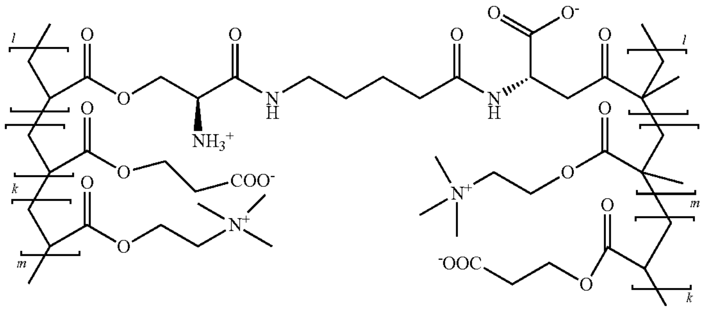
,
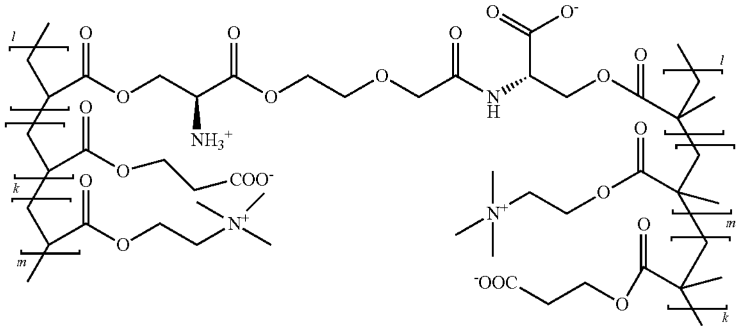
,
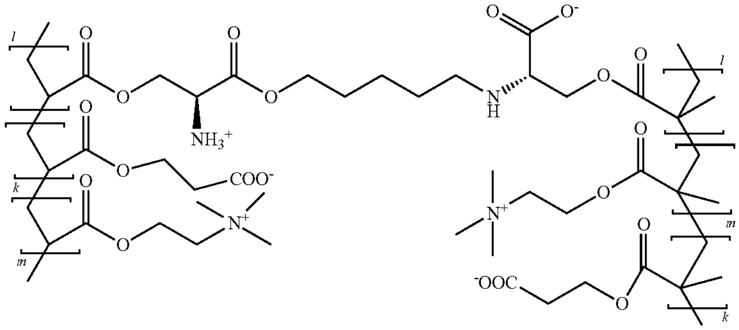
,
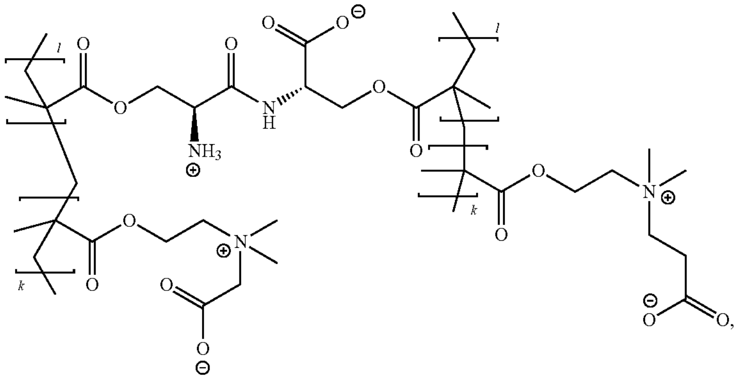
, or -continued

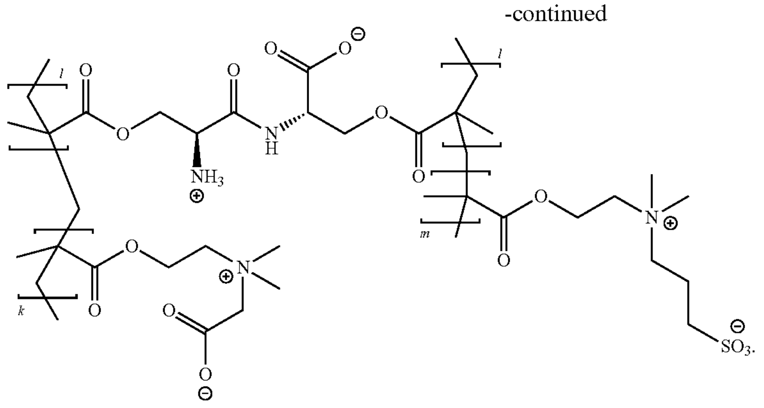

21. A method, comprising:

providing a crosslinker according to claim 1; and forming a hydrogel comprising the crosslinker.

22. The method according to claim 21, further comprising using the hydrogel to form a product selected from contact lenses, drug delivery vehicles, tissue engineering platforms, tissue regeneration platforms, catheters, implants, or sensors, wherein the product comprises the hydrogel.

23. A method for making a crosslinker according to claim 1, the method comprising:

providing a first protected amino acid comprising a Boc-protected amine, a t-butylester-protected carboxylic acid functional group, and a reactive functional group capable of reacting with a first polymerizing group;

reacting the first protected amino acid with a first polymerizing group selected from an acrylate, alkyl acrylate, acrylamide, alkyl acrylamide, acrylonitrile, alkyl acrylonitrile, or a (hydroxyalkyl) acrylate to provide a first coupled protected amino acid coupled through the reactive functional group to the first polymerizing group;

selectively removing the Boc protecting group from the first protected amino acid coupled using trifluoracetic acid to provide a first coupled amino acid;

providing a second protected amino acid comprising a Boc-protected amine, an unprotected carboxylic acid, and a reactive functional group capable of reacting with a second polymerizing group;

reacting the second protected amino acid with a second polymerizing group selected from an acrylate, alkyl acrylate, acrylamide, alkyl acrylamide, acrylonitrile, alkyl acrylonitrile, or a (hydroxyalkyl) acrylate to provide a second coupled protected amino acid coupled through the reactive functional group to the second polymerizing group;

forming a peptide bond between (i) the first coupled amino acid and (ii) the second coupled protected amino acid; and removing remaining protecting groups to form a crosslinker that is zwitterionic between a pH of 2 to 10.

24. The method according to claim 23, further comprising forming a crosslinker comprising at least one spacer group.

25. A method for making a crosslinker according to claim 1, the method comprising:

providing a first protected amino acid comprising a Boc-protected amine, an unprotected carboxylic acid functional group, and a reactive functional group capable of reacting with a first polymerizing group;

reacting the first protected amino acid with a first polymerizing group selected from an acrylate, alkyl acrylate, acrylamide, alkyl acrylamide, acrylonitrile, alkyl acrylonitrile, or a (hydroxyalkyl) acrylate to provide a first coupled protected amino acid coupled through the reactive functional group to the first polymerizing group;

protecting the unprotected carboxylic acid functional group as a t-butyl ester;

selectively removing the protecting group from the first coupled protected amino acid using trifluoracetic acid to provide an unprotected amine functional group;

providing a second protected amino acid comprising a Boc-protected amine, an unprotected carboxylic acid, and a reactive functional group capable of reacting with a second polymerizing group;

reacting the second protected amino acid with a second polymerizing group selected from acrylate, alkyl acrylate, acrylamide, alkyl acrylamide, acrylonitrile, alkyl acrylonitrile or a (hydroxyalkyl) acrylate to provide a second amine protected amino acid coupled through the reactive functional group to the second polymerizing group;

forming a peptide bond between the first protected amino acid and the second protected amino acid; and removing remaining protecting groups to form a crosslinker that is zwitterionic between a pH of from 2 to 10.

26. The method according to claim 25, further comprising forming a crosslinker comprising at least one spacer group.

27. A method for forming a crosslinked hydrogel, the method comprising:

providing a crosslinker according to claim 1; and reacting the crosslinker with a first monomer and a second monomer to form the crosslinked hydrogel.

* * * * *